US011498957B2

(12) United States Patent
Lee et al.

(10) Patent No.: US 11,498,957 B2
(45) Date of Patent: Nov. 15, 2022

(54) COMPOSITION AND METHOD FOR INHIBITING AMYLOID β ACCUMULATION AND/OR AGGREGATION

(71) Applicant: INNOPEUTICS CORPORATION, Seoul (KR)

(72) Inventors: Sang Hun Lee, Seoul (KR); Jae Jin Song, Seoul (KR); Yun Seon Yang, Seoul (KR); Tae Gyun Kim, Seoul (KR)

(73) Assignee: INNOPEUTICS CORPORATION, Seoul (KR)

( * ) Notice: Subject to any disclaimer, the term of this patent is extended or adjusted under 35 U.S.C. 154(b) by 220 days.

(21) Appl. No.: 16/898,187

(22) Filed: Jun. 10, 2020

(65) Prior Publication Data

US 2021/0017251 A1   Jan. 21, 2021

Related U.S. Application Data

(63) Continuation of application No. PCT/KR2020/003439, filed on Mar. 12, 2020.

(30) Foreign Application Priority Data

May 23, 2019  (KR) .................. 10-2019-0060883
Jan. 17, 2020  (KR) .................. 10-2020-0006861

(51) Int. Cl.
| A61K 48/00 | (2006.01) |
| C07K 14/705 | (2006.01) |
| A61P 25/28 | (2006.01) |
| C07K 14/47 | (2006.01) |
| C12N 15/86 | (2006.01) |
| A61K 9/00 | (2006.01) |
| A61K 38/00 | (2006.01) |

(52) U.S. Cl.
CPC ...... *C07K 14/70567* (2013.01); *A61K 48/005* (2013.01); *A61P 25/28* (2018.01); *C07K 14/47* (2013.01); *C12N 15/86* (2013.01); *A61K 9/0019* (2013.01); *A61K 9/0085* (2013.01); *A61K 38/00* (2013.01)

(58) Field of Classification Search
None
See application file for complete search history.

(56) References Cited

U.S. PATENT DOCUMENTS

| 2013/0052268 A1* | 2/2013 | Chung ................. A61K 48/005 514/17.7 |
| 2017/0354688 A1 | 12/2017 | Lee |
| 2018/0339000 A1 | 11/2018 | Kern |
| 2019/0185812 A1* | 6/2019 | Park ................. C12N 15/85 |

FOREIGN PATENT DOCUMENTS

| KR | 10-2012-0003098 A | 1/2012 |
| KR | 10-2019-0051837 A | 5/2019 |
| WO | WO 2018/185260 A1 | 10/2018 |

OTHER PUBLICATIONS

Bhat et al., Astrocyte Senescence as a Component of Alzheimer's Disease, PLoS One, vol. 7, No. 9, 2012.
Blasi et al., Immortalization of Murine Microglial Cells by a V-Raf/V-Myc Carrying Retrovirus, Journal of Neuroimmunology, vol. 27, pp. 229-237, 1990.
Bussian et al., Clearance of Senescent Glial Cells Prevents Tau-Dependent Pathology and Cognitive Decline, Nature, vol. 562, No. 7728, pp. 578-582, 2018.
Chinta et al., Cellular Senescence is Induced by the Environmental Neurotoxin Paraquat and Contributes to Neuropathology Linked to Parkinson's Disease, Cell Report, vol. 22, No. 4, pp. 930-994, 2018.
Czirr et al., Microglial Complement Receptor 3 Regulates Brain Abeta Levels Through Secreted Proteolytic Activity, The Journal of Experimental Medicine, vol. 214, No. 4, pp. 1081-1092, 2017.
Heinrich et al., Generation of Subtype-Specific Neurons from Postnatal Astroglia of the Mouse Cerebral Cortex, Nature Protocols, vol. 6, pp. 214-228, 2011.
Heneka et al., NLRP3 is Activated in Alzheimer's Disease and Contributes to Pathology in APP/PS1 Mice. Nature, vol. 493, No. 7434, pp. 674-678, 2013.
Hong et al., Complement and Microglia Mediate Early Synapse Loss in Alzheimer Mouse Models, Science, vol. 352, No. 6286, pp. 712-716, 2016.
Kang et al., Microglial Translational Profiling Reveals a Convergent APOE Pathway from Aging, Amyloid, and Tau, Journal of Experimental Medicine, vol. 215, No. 9, pp. 2235-2245, 2018.
Ries et al., Mechanisms of Abeta Clearance and Degradation by Glial Cells, Frontiers in Aging Neuroscience, vol. 8, No. 160, 2016.
Saura et al. Microglial Cells in Astroglial Cultures: A Cautionary Note. Journal of Neuroinflammation, vol. 4, No. 26, 2007.
Shi et al., Complement C3 Deficiency Protects Against Neurodegeneration in Aged Plaque-Rich APP/PS1 Mice, Science Translational Medicine, vol. 9, No. eaaf6295, 2017.
Venegas et al., Microglia-Derived ASC Specks Cross-Seed Amyloid-Beta in Alzheimer's Disease, Nature, vol. 552, No. 7685, pp. 355-361, 2017.
Yang et al., Differential Protective Effects of Connective Tissue Growth Factor Against Abeta Neurotoxicity on Neurons and Glia, Human Molecular Genetics, vol. 26, No. 20, pp. 3909-3921, 2017.

(Continued)

*Primary Examiner* — Sean McGarry
(74) *Attorney, Agent, or Firm* — Knobbe, Martens, Olson & Bear LLP

(57) ABSTRACT

Disclosed herein is an amyloid β accumulation and/or aggregation inhibitor. A technique for inhibiting amyloid β accumulation and/or aggregation by concurrently introducing Nurr1 and Foxa2 genes and introducing the co-expression of the genes is also provided. When used, the composition can be applied to the prevention or treatment of a neurodegenerative disease caused by amyloid β accumulation and/or aggregation, such as Alzheimer's disease.

32 Claims, 34 Drawing Sheets

Specification includes a Sequence Listing.

(56) References Cited

OTHER PUBLICATIONS

Yi et al., Foxa2 acts as a Co-Activator Potentiating Expression of the Nurr1-Induced DA Phenotype Via Epigenetic Regulation, Stem Cells and Regeneration, vol. 141, pp. 761-772, 2014.
International Search Report, dated Jun. 29, 2020 in International Application No. PCT/KR2020/003439.
Written Opinion, dated Jun. 29, 2020 in International Application No. PCT/KR2020/003439.

\* cited by examiner

| Fold change | N+F/Cont |
|---|---|
| Mmp14 | 1.553 |
| MME | 2.951 |
| MMP2 | 2.693 |
| FOLH1 | 1.501 |
| ECE1 | 1.705 |
| ACE | 1.810 |

FIG. 11a

| | N+F/Cont |
|---|---|
| Ccl3 | 0.175 |
| Ccl4 | 0.096 |

FIG. 14

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: GAPDH (F)

<400> SEQUENCE: 1
ttcagctctg ggatgaccTT                                              20

<210> SEQ ID NO 2
<211> LENGTH: 20
<212> TYPE: DNA
<213> ORGANISM: Artificial Sequence
<220> FEATURE:
<223> OTHER INFORMATION: GAPDH (R)

<400> SEQUENCE: 2
ctcatgacca cagtccatgc                                              20

<210> SEQ ID NO 3
<211> LENGTH: 21
<212> TYPE: DNA
<213> ORGANISM: Artificial Sequence
<220> FEATURE:
<223> OTHER INFORMATION: BDNF (F)

<400> SEQUENCE: 3
gtgacagtat tagcgagtgg g                                            21

<210> SEQ ID NO 4
<211> LENGTH: 17
<212> TYPE: DNA
<213> ORGANISM: Artificial Sequence
<220> FEATURE:
<223> OTHER INFORMATION: BDNF (R)
```

```
<400> SEQUENCE: 4
gggtagttcg gcattgc                                                        17

<210> SEQ ID NO 5
<211> LENGTH: 20
<212> TYPE: DNA
<213> ORGANISM: Artificial Sequence
<220> FEATURE:
<223> OTHER INFORMATION: GDNF (F)

<400> SEQUENCE: 5
aacatgcctg gcctactttg                                                     20

<210> SEQ ID NO 6
<211> LENGTH: 20
<212> TYPE: DNA
<213> ORGANISM: Artificial Sequence
<220> FEATURE:
<223> OTHER INFORMATION: GDNF (R)

<400> SEQUENCE: 6
gacttgggtt tgggctatga                                                     20

<210> SEQ ID NO 7
<211> LENGTH: 23
<212> TYPE: DNA
<213> ORGANISM: Artificial Sequence
<220> FEATURE:
<223> OTHER INFORMATION: SHH (F)

<400> SEQUENCE: 7
ggatgcgagc tttggattca tag                                                 23

<210> SEQ ID NO 8
<211> LENGTH: 21
<212> TYPE: DNA
<213> ORGANISM: Artificial Sequence
<220> FEATURE:
<223> OTHER INFORMATION: SHH (R)

<400> SEQUENCE: 8
ggaagatcac aaactccgaa c                                                   21

<210> SEQ ID NO 9
<211> LENGTH: 20
<212> TYPE: DNA
<213> ORGANISM: Artificial Sequence
<220> FEATURE:
<223> OTHER INFORMATION: ARG-1 (F)

<400> SEQUENCE: 9
tatcggagcg cctttctcta                                                     20

<210> SEQ ID NO 10
<211> LENGTH: 20
<212> TYPE: DNA
<213> ORGANISM: Artificial Sequence
<220> FEATURE:
<223> OTHER INFORMATION: ARG-1 (R)

<400> SEQUENCE: 10
acagaccgtg ggttcttcac                                                     20

<210> SEQ ID NO 11
```

<211> LENGTH: 20
<212> TYPE: DNA
<213> ORGANISM: Artificial Sequence
<220> FEATURE:
<223> OTHER INFORMATION: MME (F)

<400> SEQUENCE: 11
ctaccggcca gagtatgcag                                           20

<210> SEQ ID NO 12
<211> LENGTH: 20
<212> TYPE: DNA
<213> ORGANISM: Artificial Sequence
<220> FEATURE:
<223> OTHER INFORMATION: MME (R)

<400> SEQUENCE: 12
ttcttgcggc aatgaaaggc                                           20

<210> SEQ ID NO 13
<211> LENGTH: 20
<212> TYPE: DNA
<213> ORGANISM: Artificial Sequence
<220> FEATURE:
<223> OTHER INFORMATION: MMP14 (F)

<400> SEQUENCE: 13
aggaggagac ggaggtgatc                                           20

<210> SEQ ID NO 14
<211> LENGTH: 20
<212> TYPE: DNA
<213> ORGANISM: Artificial Sequence
<220> FEATURE:
<223> OTHER INFORMATION: MMP14 (R)

<400> SEQUENCE: 14
gtcccatggc gtctgaagaa                                           20

<210> SEQ ID NO 15
<211> LENGTH: 20
<212> TYPE: DNA
<213> ORGANISM: Artificial Sequence
<220> FEATURE:
<223> OTHER INFORMATION: IDE (F)

<400> SEQUENCE: 15
gctgatgact gaagtggcct                                           20

<210> SEQ ID NO 16
<211> LENGTH: 20
<212> TYPE: DNA
<213> ORGANISM: Artificial Sequence
<220> FEATURE:
<223> OTHER INFORMATION: IDE (R)

<400> SEQUENCE: 16
caatatgcag ccgtgacagc                                           20

<210> SEQ ID NO 17
<211> LENGTH: 20
<212> TYPE: DNA
<213> ORGANISM: Artificial Sequence
<220> FEATURE:
<223> OTHER INFORMATION: ECE2 (F)

<400> SEQUENCE: 17
agacttcctt cggcacttcg                                               20

<210> SEQ ID NO 18
<211> LENGTH: 20
<212> TYPE: DNA
<213> ORGANISM: Artificial Sequence
<220> FEATURE:
<223> OTHER INFORMATION: ECE2 (R)

<400> SEQUENCE: 18
accacacctc acatagctgc                                               20

<210> SEQ ID NO 19
<211> LENGTH: 20
<212> TYPE: DNA
<213> ORGANISM: Artificial Sequence
<220> FEATURE:
<223> OTHER INFORMATION: TNFa (F)

<400> SEQUENCE: 19
agatgtggaa ctggcagagg                                               20

<210> SEQ ID NO 20
<211> LENGTH: 20
<212> TYPE: DNA
<213> ORGANISM: Artificial Sequence
<220> FEATURE:
<223> OTHER INFORMATION: TNFa (R)

<400> SEQUENCE: 20
cccatttggg aacttctcct                                               20

<210> SEQ ID NO 21
<211> LENGTH: 19
<212> TYPE: DNA
<213> ORGANISM: Artificial Sequence
<220> FEATURE:
<223> OTHER INFORMATION: IL-1b (F)

<400> SEQUENCE: 21
tgttgatgtg ctgctgcga                                                19

<210> SEQ ID NO 22
<211> LENGTH: 22
<212> TYPE: DNA
<213> ORGANISM: Artificial Sequence
<220> FEATURE:
<223> OTHER INFORMATION: IL-1b (R)

<400> SEQUENCE: 22
aagttgacgg accccaaaat at                                            22

<210> SEQ ID NO 23
<211> LENGTH: 22
<212> TYPE: DNA
<213> ORGANISM: Artificial Sequence
<220> FEATURE:
<223> OTHER INFORMATION: INOS (F)

<400> SEQUENCE: 23
cgtaccggat gagctgtgaa tt                                            22

<210> SEQ ID NO 24
<211> LENGTH: 19
<212> TYPE: DNA

```
<213> ORGANISM: Artificial Sequence
<220> FEATURE:
<223> OTHER INFORMATION: INOS (R)

<400> SEQUENCE: 24
gccaccaaca atggcaaca                                                  19

<210> SEQ ID NO 25
<211> LENGTH: 21
<212> TYPE: DNA
<213> ORGANISM: Artificial Sequence
<220> FEATURE:
<223> OTHER INFORMATION: IL-6 (F)

<400> SEQUENCE: 25
tgaaggactc tggctttgtc t                                               21

<210> SEQ ID NO 26
<211> LENGTH: 21
<212> TYPE: DNA
<213> ORGANISM: Artificial Sequence
<220> FEATURE:
<223> OTHER INFORMATION: IL-6 (R)

<400> SEQUENCE: 26
atggatgcta ccaaactgga t                                               21

<210> SEQ ID NO 27
<211> LENGTH: 20
<212> TYPE: DNA
<213> ORGANISM: Artificial Sequence
<220> FEATURE:
<223> OTHER INFORMATION: ASC (F)

<400> SEQUENCE: 27
caccagccaa gacaagatga                                                 20

<210> SEQ ID NO 28
<211> LENGTH: 20
<212> TYPE: DNA
<213> ORGANISM: Artificial Sequence
<220> FEATURE:
<223> OTHER INFORMATION: ASC (R)

<400> SEQUENCE: 28
ctccaggtcc atcaccaagt                                                 20

<210> SEQ ID NO 29
<211> LENGTH: 20
<212> TYPE: DNA
<213> ORGANISM: Artificial Sequence
<220> FEATURE:
<223> OTHER INFORMATION: NLRP3 (F)

<400> SEQUENCE: 29
atgctgcttc gacatctcct                                                 20

<210> SEQ ID NO 30
<211> LENGTH: 20
<212> TYPE: DNA
<213> ORGANISM: Artificial Sequence
<220> FEATURE:
<223> OTHER INFORMATION: NLRP3 (R)

<400> SEQUENCE: 30
gtttctggag gttgcagagc                                                 20
```

```
<210> SEQ ID NO 31
<211> LENGTH: 20
<212> TYPE: DNA
<213> ORGANISM: Artificial Sequence
<220> FEATURE:
<223> OTHER INFORMATION: Casp1 (F)

<400> SEQUENCE: 31
cacagctctg gagatggtga                                                    20

<210> SEQ ID NO 32
<211> LENGTH: 20
<212> TYPE: DNA
<213> ORGANISM: Artificial Sequence
<220> FEATURE:
<223> OTHER INFORMATION: Casp1 (R)

<400> SEQUENCE: 32
ggtcccacat attccctcct                                                    20

<210> SEQ ID NO 33
<211> LENGTH: 20
<212> TYPE: DNA
<213> ORGANISM: Artificial Sequence
<220> FEATURE:
<223> OTHER INFORMATION: Nurr1 (F)

<400> SEQUENCE: 33
catggacctc accaacactg                                                    20

<210> SEQ ID NO 34
<211> LENGTH: 20
<212> TYPE: DNA
<213> ORGANISM: Artificial Sequence
<220> FEATURE:
<223> OTHER INFORMATION: Nurr1 (R)

<400> SEQUENCE: 34
acaggggcat ttggtacaag                                                    20

<210> SEQ ID NO 35
<211> LENGTH: 20
<212> TYPE: DNA
<213> ORGANISM: Artificial Sequence
<220> FEATURE:
<223> OTHER INFORMATION: rFoxa2 (F)

<400> SEQUENCE: 35
gctccctacg ccaatatcaa                                                    20

<210> SEQ ID NO 36
<211> LENGTH: 20
<212> TYPE: DNA
<213> ORGANISM: Artificial Sequence
<220> FEATURE:
<223> OTHER INFORMATION: rFoxa2 (R)

<400> SEQUENCE: 36
ccggtagaaa gggaagaggt                                                    20
```

COMPOSITION AND METHOD FOR INHIBITING AMYLOID β ACCUMULATION AND/OR AGGREGATION

PRIORITY AND CROSS REFERENCE TO RELATED APPLICATIONS

This application is a Continuation Application of International Application No. PCT/KR2020/003439, filed Mar. 12, 2020, designating the U.S., which claims the benefit of Korean Application No. KR 10-2019-0060883, filed May 23, 2019, and Korean Application No. KR 10-2020-0006861, filed Jan. 17, 2020, which are hereby incorporated by reference in their entireties.

SEQUENCE LISTING IN ELECTRONIC FORMAT

The present application is being filed along with an Electronic Sequence Listing as an ASCII text file via EFS-Web. The Electronic Sequence Listing is provided as a file entitled ZNTH001001C1SEQLIST.txt, created and last saved on Jun. 10, 2020, which is 7,372 bytes in size. The information in the Electronic Sequence Listing is incorporated herein by reference in its entirety.

TECHNICAL FIELD

The present disclosure relates to an inhibitor against amyloid β accumulation and/or aggregation and, more particularly, to compositions and methods for inhibiting amyloid β accumulation and/or aggregation by concurrently introducing Nurr1 and Foxa2 genes to a mammal.

BACKGROUND OF THE INVENTION

Alzheimer's disease is a chronic neurodegenerative disease having symptoms most commonly including memory loss, difficulties with language, cognitive impairment, etc.

Alzheimer's disease is neuropathologically characterized by the presence of plaques in brain cells, nervous tissues, and vessels, neurofibrillary tangles (NFTs), the presence of amyloid β responsible for the formation of amyloid plaques, the loss of synapses, etc. The cause for most Alzheimer's cases still remains unknown. Further, there has been no cure for Alzheimer's disease, thus far. Alzheimer's disease accounts for the most common cases of dementia, acting as a main cause of death, like cardiovascular diseases and cancer. The frequency of Alzheimer's disease is predicted to increase with the average lifespan of humans.

In addition, an enormous expense is required for managing and treating Alzheimer's disease, with the patients suffering from considerable mental anguish. Therefore, there is a need for effective method for preventing and treating Alzheimer's disease.

SUMMARY OF THE INVENTION

Leading to the present disclosure, the research conducted by the present inventors resulted in the experimental finding that introduction and expression of Nurr1 and Foxa2 genes in brain cells inhibits the accumulation and/or aggregation of amyloid β. Particularly, when a Nurr1 gene was expressed together with a Foxa2 gene rather than alone, the two genes were found to have a potent synergistic effect of inhibiting amyloid β accumulation and/or aggregation.

Therefore, one embodiment of the present disclosure provides an amyloid β accumulation and/or aggregation inhibitor comprising a vector carrying both a Nurr1 gene and a Foxa2 gene.

Another embodiment of the present disclosure provides an amyloid β accumulation and/or aggregation inhibitor comprising neurons, neuronal stem cells or neuronal precursor cells, or glia, which all have both a Nurr1 gene and a Foxa2 gene introduced thereinto.

Still another embodiment of the present disclosure provides an inhibitor against the expression of inflammasomes, complements, chemokines (CCL3 and CCL4), inflammatory cytokines (IL-1β and TNF-α), apolipoprotein E (ApoE), nuclear factor kappa-light-chain-enhancer of activated B cells (NFκB), or asparaginyl endopeptidase (AEP), the inhibitor comprising a vector carrying both a Nurr1 gene and a Foxa2 gene.

Yet another embodiment of the present disclosure provides an inhibitor against the expression of inflammasomes, complements, chemokines (CCL3 and CCL4), inflammatory cytokines (IL-1β and TNF-α), apolipoprotein E (ApoE), nuclear factor kappa-light-chain-enhancer of activated B cells (NFκB), or asparaginyl endopeptidase (AEP), the inhibitor comprising neurons, neuronal stem cells or neuronal precursor cells, or glia, which all have both a Nurr1 gene and a Foxa2 gene introduced thereinto.

Still a further embodiment of the present disclosure provides a composition for preventing or treating a disease caused due to amyloid β accumulation and/or aggregation, the composition comprising a vector carrying both a Nurr1 gene and a Foxa2 gene.

Another embodiment of the present disclosure provides a composition for preventing or treating a disease caused due to amyloid β accumulation and/or aggregation, the composition comprising neurons, neuronal stem cells or neuronal precursor cells, or glia, which all have both a Nurr1 gene and a Foxa2 gene introduced thereinto.

One other embodiment of the present disclosure provides a composition for inhibiting cellular senescence caused due to amyloid β accumulation and/or aggregation, the composition comprising a vector carrying both a Nurr1 gene and a Foxa2 gene.

Another embodiment of the present disclosure is a method of treating a patient suffering from Alzheimer's disease, comprising administering to the patient a therapeutically effective dose of a composition comprising a vector carrying both a Nurr1 gene and a Foxa2 gene.

Another embodiment of the present disclosure is a method of treating a patient suffering from Alzheimer's disease, comprising administering to the patient a therapeutically effective dose of a composition comprising a vector carrying a Nurr1 gene and a second vector carrying a Foxa2 gene.

BRIEF DESCRIPTION OF THE DRAWINGS

The above and other aspects, features and advantages of the present disclosure will be more apparent from the following detailed description taken in conjunction with the accompanying drawings, in which:

FIG. 11a shows ratios of gene expression levels of enzymes associated with the disaggregation of amyloid β in Nurr1+Foxa2-expressed glia to those in control glia after co-expression of Nurr1+Foxa2 genes in murine primary astrocytes, as measured by RNA-Seq analysis:

FIG. 14 shows levels of CCL3 and CCL4 in glia after co-expression of Nurr1+Foxa2 genes therein, as analyzed by RNA-Seq:

DETAILED DESCRIPTION OF THE INVENTION

Figure 1:
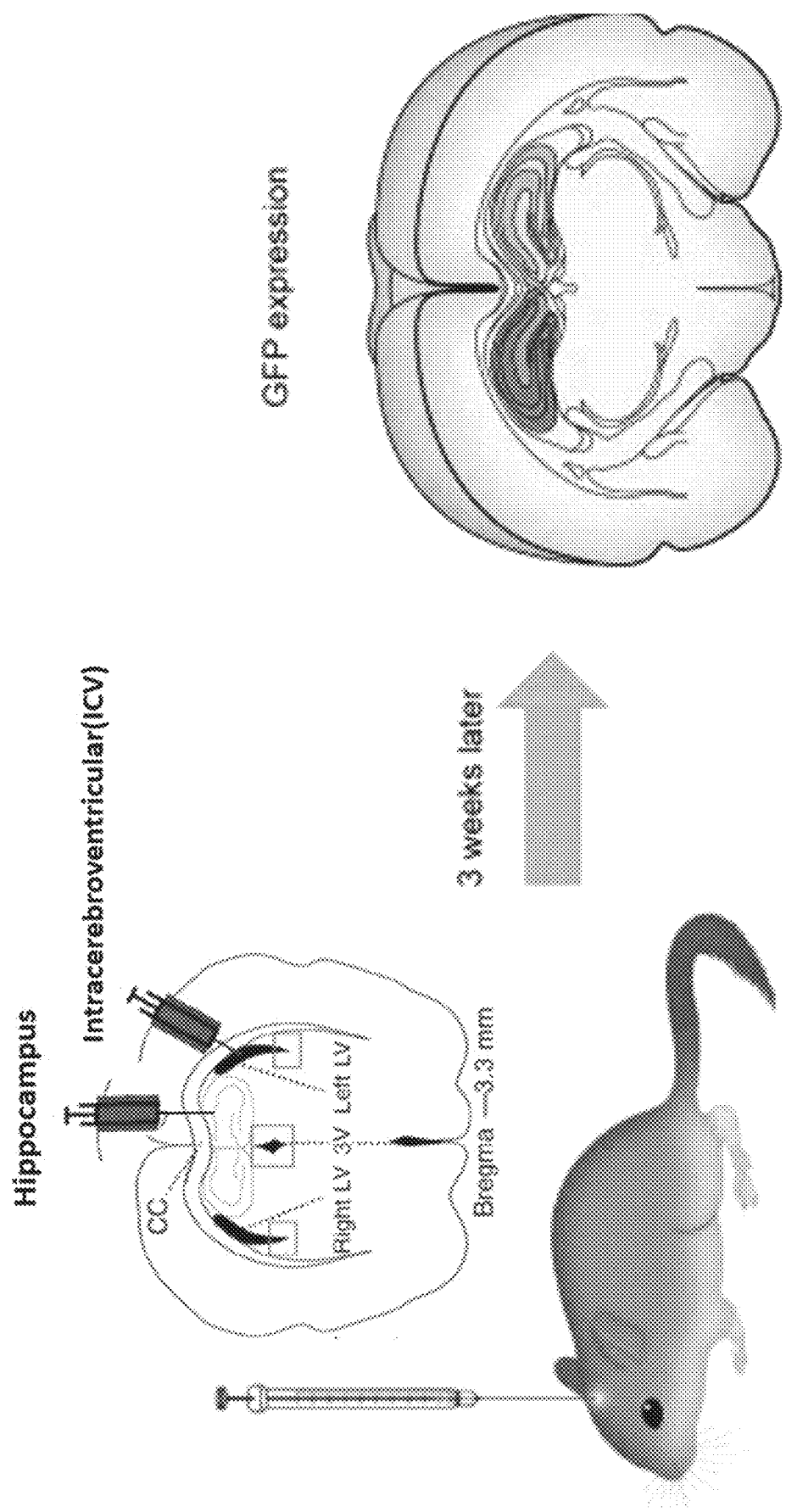
FIG. 1 illustrates gene delivery test processes using AAV9 virus.

Nuclear receptor-related factor 1 (Nurr1, also known as NR4A2) is an orphan nuclear receptor initially characterized as a transcription factor important for mDA neuron development, including the generation, maturation, and axonal pathfinding of midbrain dopamine (mDA) neurons. Nurr1 continues to be expressed in adult mDA neurons, and adult-onset deletion of the protein leads to progressive loss of mDA neurons. In heterozygous Nurr1 mice, mDA neurons are more vulnerable to dopaminergic neurotoxins. The Nurr1 level in mDA neurons decreases in the elderly and Alzheimer's disease patients. These findings support the conception that Nurr1 exerts a protective effect on adult mDA neurons in a cell-autonomous manner.

Indeed, several intrinsic mechanisms implicated in Nurr1-mediated cell survival have been identified. Particularly, glia in nervous tissues include astrocytes and microglia, acting as an auxiliary cell to aid the functions and survival of neurons.

Intensive and thorough research, conducted by the present inventors, into an approach of inhibiting the accumulation and/or aggregation of amyloid $\beta$, which is known as one of leading causes of Alzheimer's disease, culminated in the finding that concurrent expression of Nurr1 and Foxa2 genes was found to exhibit inhibitory effects on the accumulation and/or aggregation of amyloid $\beta$, the expression of inflammasomes complements, chemokines (CCL3 and CCL4), inflammatory cytokines (IL-1$\beta$ and TNF-$\alpha$), apolipoprotein E (ApoE), or asparaginyl endopeptidase (AEP), and the cellular senescence-induced amyloid $\beta$ accumulation.

Provided according to an aspect of the present disclosure is an amyloid $\beta$ accumulation and/or aggregation inhibitor comprising a vector having both a Nurr1 gene and a Foxa2 gene introduced thereinto.

According to an embodiment of the present disclosure, the vector is a viral vector or a non-viral vector.

According to an embodiment of the present disclosure, the introduction of the genes into a mammal is achieved by gene editing.

Provided according to another aspect of the present disclosure is an amyloid $\beta$ accumulation and/or aggregation inhibitor comprising neurons, neuronal stem cells or neuronal precursor cells, or glia, which all have both a Nurr1 gene and a Foxa2 gene introduced thereinto and expressing the Nurr1 and Foxa2 proteins.

According to an embodiment of the present disclosure, the introduction is achieved using a viral vector, a non-viral vector, or gene editing.

According to an embodiment of the present disclosure, the glia are astrocytes or microglia.

Provided according to another aspect of the present disclosure is an inhibitor against the expression of inflammasomes, complements, chemokines (CCL3 and CCL4), inflammatory cytokines (IL-1$\beta$ and TNF-$\alpha$), apolipoprotein E (ApoE), nuclear factor kappa-light-chain-enhancer of activated B cells (NFκB), or asparaginyl endopeptidase (AEP), the inhibitor comprising a vector carrying both a Nurr1 gene and a Foxa2 gene, and a pharmaceutical composition.

According to an embodiment of the present disclosure, the vector is a viral vector or a non-viral vector.

According to an embodiment of the present disclosure, the introduction of the genes is achieved by gene editing.

Provided according to another aspect of the present disclosure is an inhibitor against the expression of inflammasomes, complements, chemokines (CCL3 and CCL4), inflammatory cytokines (IL-1$\beta$ and TNF-$\alpha$), apolipoprotein E (ApoE), nuclear factor kappa-light-chain-enhancer of activated B cells (NFκB), or asparaginyl endopeptidase (AEP), the inhibitor comprising neurons, neuronal stem cells or neuronal precursor cells, or glia, which all have both a Nurr1 gene and a Foxa2 gene introduced thereinto.

According to an embodiment of the present disclosure, the introduction is achieved using a viral vector, a non-viral vector, or gene editing.

According to an embodiment of the present disclosure, the glia are astrocytes or microglia.

Provided according to another aspect of the present disclosure is a composition for preventing or treating a disease caused due to amyloid $\beta$ accumulation and/or aggregation, the composition comprising a vector carrying both a Nurr1 gene and a Foxa2 gene.

According to an embodiment of the present disclosure, the vector is a viral vector or a non-viral vector.

According to an embodiment of the present disclosure, the introduction of the genes is achieved by gene editing.

Provided according to another aspect of the present disclosure is a pharmaceutical composition for preventing or treating a disease caused due to amyloid $\beta$ accumulation and/or aggregation, the composition comprising neurons, neuronal stem cells or neuronal precursor cells, or glia, which all have both a Nurr1 gene and a Foxa2 gene introduced thereinto.

According to an embodiment of the present disclosure, the introduction is achieved using a viral vector, a non-viral vector, or gene editing.

According to an embodiment of the present disclosure, the glia are astrocytes or microglia.

Provided according to another aspect of the present disclosure is a composition for inhibiting cellular senescence caused due to amyloid $\beta$ accumulation and/or aggregation, the composition comprising a vector carrying both a Nurr1 gene and a Foxa2 gene.

According to an embodiment of the present disclosure, the glia are astrocytes or microglia.

In one embodiment, a Nurr1 gene and a Foxa2 gene are both expressed so that the respective proteins act in synergy with each other to prevent and treat Alzheimer's disease. The expression of Nurr1 and Foxa2 alleviates pathological symptoms of Alzheimer's disease, including and not limited to (1) amyloid $\beta$ accumulation, (2) brain cell aging, and (3) synapse loss. In addition, the expression of Nurr1 and Foxa2 significantly reduces an expression level of inflammasomes, which injure brain cells, and inhibits the accumulation of peripheral immune cells or complements, thereby exerting a preventive and therapeutic effect on Alzheimer's disease. A better preventive and therapeutic effect is brought about on Alzheimer's disease when both of Nurr1 and Foxa2 rather than only one of the two genes are expressed in brain cells because a dramatically synergistic action is induced to alleviate pathological symptoms of Alzheimer's disease.

As used herein, the term "induction (transduction)" in conjunction with Nurr1 and Foxa2 refers to the introduction of the two genes coding for the proteins into brain cells. The two genes may be introduced separately or together. So long as it can introduce genes coding for Nurr1 and Foxa2 into brain cells, any technique known in the art may be used. Examples of the techniques for intracellular introduction of genes include DNA-calcium precipitation, liposomal transfection, polyamine-based transfection, electroporation, retroviral transduction, adenoviral transduction, and adeno-associated viral (AAV) transduction.

For use in introducing Nurr1 and Foxa2 into cells, a viral or non-viral vector may be employed. For the viral vector, adeno-associated virus (AAV), adenovirus, retrovirus, and/or lentivirus may be used while the non-viral vector may be exemplified by RNA molecules, plasmids, liposomal complexes, molecular conjugates, and/or gene editing proteins (CRISPR, e.g., Cas9).

In an embodiment of the present disclosure, accordingly, the introduction of Nurr1 and Foxa2 according to the present disclosure comprises inserting nucleic acids encoding Nurr1 and Foxa2 into respective expression vectors or one vector and introducing the vectors or the vector into brain cells.

The introduction of Nurr1 and Foxa2 may be achieved using gene editing technology. Genome editing technology is a type of genetic engineering in which genetic information of a living organism is edited to elicit a desired genetic trait. Available in genome editing are zinc finger nuclease (ZFN), transcription activator-like effector-based nuclease (TALEN), and clustered regularly interspaced short palindromic repeats/CRISR system (CRISPR/Cas9).

As used herein, the term "RNA-guided nuclease" refers to a nuclease that can recognize and cleave a specific locus on a target genome, particularly with target specificity driven by guide RNA. The RNA-guided nuclease may be a Cas protein in conjunction with CRISPR, which contributes to a prokaryotic immune system. Examples of the RNA-guided nuclease include, but are not limited to, Cas9 (CRISPR-Associated Protein 9) nuclease and derivatives thereof, such as Cas9 nickase.

As used herein, the term "Cas protein" refers to a protein capable of functioning as an activated endonuclease which plays a vital role in the CRISPR/Cas system. The Cas protein forms a complex with the two disparate RNAs crRNA (CRISPR RNA) and tracrRNA (trans-activating crRNA) to exhibit the activity.

Apart from its original function in bacterial immunity, the Cas9 nuclease has been heavily utilized as a genome engineering tool to recognize a specific nucleotide sequence and induce a site-directed double-strand break (DSB) in the genomes of animal and plant cells including human cells. The DSB results in a blunt end or a cohesive end. DSB is effectively repaired by the homologous recombination or non-homologous end-joining (NHEJ) mechanism. Through the mechanism, a desired mutation can be introduced to a target site in many laboratory model organisms. The RNA-guided nuclease may be artificial, or engineered, non-naturally occurring.

The Cas9 nickase includes at least one mutation in one of the catalytic domains of Cas9 nuclease. The at least one mutation is selected from the group consisting of D10A, E762A, and D986A in the RuvC domain or from the group consisting of H840A, N854A, and N863A in the HNH domain. Unlike Cas9 nuclease, the Cas9 nickase generates a single-strand break. Therefore, two guide RNAs are required for the performance of Cas9 nickase and function as a pair. The two guide RNA instruct the CRISPR complex to bind to respective target sequences in sequence specific manner and to break each strand of DNA duplex at a site near each of the target sequences to induce two nicks on the different DNA strands.

Information on Cas proteins or genes can be acquired from well-known database such as the GenBank of NCBI (National Center for Biotechnology Information). In one embodiment, the Cas protein may be a Cas9 protein. Examples of the Cas protein include, but are not limited to, Cas proteins derived from *Staphylococcus* spp., *Streptococcus* spp., *Neisseria* spp., *Pasteurella* spp., *Francisella* spp., and *Campylobacter* spp. In one embodiment, the Cas protein may be a Cas9 protein derived from *Staphylococcus* spp. Examples described here may not limit the scope of the present disclosure. In one embodiment, the Cas protein may be a recombinant protein.

So long as it encodes Nurr1 or Foxa2, any nucleotide sequence well known in the art may be used without limitations thereto. In addition, the nucleotide sequence may code for a functional equivalent to Nurr1 or Foxa2. The functional equivalent refers to a polypeptide having a homology (e.g., identity) of 70% or more, particularly 80% or more, and more particularly 90% or more with the amino acid sequence of either of Nurr1 and Foxa2. Within the scope of the functional equivalent, for example, there are polypeptides that have a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% with the amino acid sequence of either of Nurr1 and Foxa2. The functional equivalent may result from addition, substitution, or deletion of a part of the amino acid sequence. Particularly, the addition, substitution, or deletion occurs in a region that is not responsible for the biological activity of the polypeptide of the present disclosure.

In addition, the nucleic acid coding for Nurr1 or Foxa2 may be prepared using any gene manipulation method known in the art (Sambrook, Fritsch and Maniatis, 'Molecular Cloning, A laboratory Manual, Cold Spring Harbor laboratory press, 1989; Short Protocols in Molecular Biology, John Wiley and Sons, 1992). For example, a nucleic acid can be acquired through PCR, which is designed to amplify a nucleic acid from a genome, chemical synthesis, or cDNA synthesis.

Either or both of Nurr1 and Foxa2 genes may be operably linked to an expression control sequence in an expression vector. As used herein, the term "operably linked" means that genetic elements are joined to each other in such a manner that enables them to carry out their normal functions. The term "expression control sequence" refers to a DNA sequence that regulates the expression of a nucleotide sequence operably linked thereto in a specific host cell. Such regulatory elements include a promotor for initiating transcription, an operator for regulatory transcription, a sequence coding for a suitable mRNA ribosomal binding site, and sequences responsible for terminating transcription and translations. These elements may be collectively expressed as "DNA construct carrying nucleic acids coding for Nurr1 and Foxa2".

The term "expression vector", as used herein, refers to a plasmid, a viral vector, or a mediator that allows a nucleic acid encoding a structural protein to be inserted thereinto and to be expressed in a host cell. So long as it is known in the art, any expression vector may be used in the present disclosure. One preferable vector is a viral vector. Examples of the viral vectors include, but are not limited to, an adenoviral vector, an adeno-associated virus (AAV) vector, a herpes virus vector, an avipoxvirus vector, and a lentivirus vector.

An adeno-associated virus (AAV) vector can be constructed by introducing into specific cells materials capable of producing viruses. For construction of the lentivirus vector, a specific cell line is treated in many stages. For use in gene therapy, an adeno-associated virus (AAV) vector or a lentivirus vector enjoys advantages of efficiency and stability.

An expression vector carrying the nucleic acid according to the present disclosure may be introduced into brain cells by using many methods known in the art. Examples of the methods include, but are not limited to, transient transfection, microinjection, transduction, cell fusion, calcium phosphate precipitation, liposome-mediated transfection, DEAE (dextran-mediated transfection), polybrene-mediated transfection, electroporation, gene gun, and other methods known to introduce a nucleic acid into cells. By way of example, either or both of Nurr1 and Foxa2 genes are inserted into an AAV vector or a lentiviral vector to construct an expression vector that is then transduced into packaging cells. The transduced packaging cells are cultured, followed by filtration to obtain an AAV or lentiviral solution. This lentiviral solution is used to infect brain cells, neurons, and/or neuronal stem cells, whereby Nurr1 and Foxa2 genes can be introduced into brain cells. Thereafter, desired brain cells which concurrently express Nurr1 and Foxa2 can be identified using a selection marker included in the AAV or lentiviral vector.

In an embodiment, brain cells that express Nurr1 and Foxa2 according to the present disclosure can be generated using a method comprising the following steps of:

(a) constructing a recombinant viral vector carrying a DNA construct of nucleic acids coding for Nurr1 and Foxa2, respectively;

(b) infecting a virus producing cell line with the recombinant viral vector to produce a recombinant virus expressing Nurr1 and Foxa2; and (c) infecting brain cells with the recombinant virus expressing Nurr1 and Foxa2.

First, the DNA construct of nucleic acids coding for Nurr1 and Foxa2 is as described above.

The DNA construct is operably liked to an expression control sequence, e.g., a promoter, and then inserted into a viral vector known in the art to construct a recombinant viral vector. Subsequently, the recombinant viral vector carrying nucleic acids coding for Nurr1 and Foxa2 is introduced in a cell line for viral production. The cell line for viral production may be a cell line that produces the virus corresponding to the viral vector used. Thereafter, the recombinant virus expressing Nurr1 and Foxa2, e.g., recombinant AAV or lentivirus, is infected into brain cells. This infection may be carried out using a method known in the art.

The brain cells expressing Nurr1 and Foxa2 according to the present disclosure can be grown and proliferated according to methods known in the art.

In one embodiment, the brain cells of the present disclosure are grown in a culture medium designed to aid the survival or proliferation of target types of cells. Often, a culture medium employing free amino acids, instead of serum, as a nutrition source is preferred. In one embodiment, the culture medium is supplemented with an additive developed for continuously culturing brain cells. For example, the additive may include N2 medium, B27 supplement, and/or bovine serum that are all commercially available from Gibco®. The culture medium may be preferably exchanged with fresh media under the monitoring of states of the culture medium and cells. In this regard, when the brain cells grow and aggregate into neurospheres, the cells may be preferably passaged. Cell passaging may be performed every 7-8 days according to the specific protocols for managing cell growth.

Expression of Nurr1 and Foxa2 in brain cells reduces pathological symptoms of Alzheimer's disease including (1) amyloid β accumulation, (2) brain cell senescence, and (3) synapse loss, and provides the brain cells with neurotrophic factors, thereby helping prevent and treat Alzheimer's disease. Compared to expression of Nurr1 or Foxa2 alone, co-expression of Nurr1 and Foxa2 results in a dramatically synergistic effect of reducing pathological symptoms of Alzheimer's disease, thereby preventing and treating Alzheimer's disease.

Provided according to another aspect of the present disclosure is a use of brain cells having Nurr1 and Foxa2 introduced thereinto in treating Alzheimer's disease.

For example, the cells having Nurr1 and Foxa2 introduced thereinto may be therapeutically used by being directly injected into a midbrain region of a mammal according to the disease or state to be treated. In addition, a therapeutic use of the cells having Nurr1 and Foxa2 introduced thereinto may be accomplished by administering a composition containing a therapeutically effective amount of the brain cells or by transplanting the brain cells. Furthermore, the present disclosure concerns a method for treatment of Alzheimer's disease by introducing cells expressing Nurr1 and Foxa2 into a patient suffering from Alzheimer's disease.

Therefore, contemplated according to another aspect of the present disclosure is a composition, a cell therapy product, or a gene medicine comprising brain cells having Foxa2 and Nurr1 introduced thereinto as an active ingredient for preventing or treating a disease (e.g., Alzheimer's disease, etc.) caused by the accumulation and/or aggregation of amyloid β.

The gene medicine or cell therapy product of the present disclosure functions to prevent the accumulation of amyloid R and to protect brain cells, inclusive of neurons and glia, against damage, thereby resulting in the resultant supplement (regeneration) or reconstruction (restoration) of memory-related neurons.

The cell therapy product of the present disclosure exhibits supplementation (regeneration) or reconstruction (restoration) effects on damaged neurons in the brain. As used herein, the term "regeneration" refers to supplementation of a part in an organ or subject when the part is lost and the term "restoration", interchangeably used with "reconstitution", refers to reconstructing a tissue or organ when the tissue or organ is dissociated.

The composition or cell therapy product of the present disclosure may be formulated into a suitable preparation comprising an acceptable carrier according to administration type. Suitable preparations according to administration types are well known and may typically include an agent that penetrates into the membrane or makes transmembrane passage easy.

In addition, the composition of the present disclosure may be used in a form of a general medicinal preparation. A parenteral preparation may be prepared in a form of a sterile aqueous solution, a non-aqueous solvent, a suspending agent, oil, or a freeze-drying preparation. For oral administration, the composition of the present disclosure may be prepared in a form of a tablet, troche, capsule, elixir, suspension, syrup, or wafer. For injections, the composition may be prepared into a single-dose ampoule or multi-dose container. In addition, the composition for treatment of the present disclosure may be administered together with a pharmaceutically acceptable carrier. For example, for oral administration, a binder, a lubricant, a disintegrator, an excipient, a solubilizer, a dispersing agent, a stabilizer, a suspending agent, a coloring agent, a perfume, or the like may be used. For injections, a buffer, a preservative, an analgesic, a solubilizer, an isotonic agent, a stabilizer, or the like may be used. For topical administration, a base, an excipient, a lubricant, a preservative, or the like may be used.

In addition, a method for treating Alzheimer's disease by using the composition of the present disclosure may include administering to a patient through a general route in which a predetermined material is introduced in a proper manner. The manner of administration may be intracerebral, intracerebroventricular, intraspinal, intraperitoneal, intravenous, intramuscular, subcutaneous, intradermal, oral, topical, intranasal, intrapulmonary, or intrarectal administration, but is not limited thereto. For oral administration, the preparation is preferably formulated to coat the active ingredient or protect the active ingredient from being degraded in the stomach because the cells may be digested.

Furthermore, the pharmaceutical composition may be administered by any device to transmit an active ingredient to target cells. A preferable administration method and type of preparation is an injection, for example, an injection using a stereotactic system, such as a hippocampal injection, an intracerebroventriular injection, a midbrain injection, and an intracerebrospinal injection, an intravenous injection, a subcutaneous injection, an intradermal injection, an intramuscular injection, or a drip infusion. The injection may be prepared using an aqueous solvent such as a physiological saline or a Ringer's solution, or a non-aqueous solvent such as a vegetable oil, a higher fatty acid ester (e.g., ethyl oleate), alcohols (e.g., ethanol, benzyl alcohol, propylene glycol, polyethylene glycol or glycerin), and may include a pharmaceutically acceptable carrier, such as a stabilizer for preventing spoilage (ascorbic acid, sodium hydrogen sulfite, BHA, tocopherol or EDTA), an emulsifier, a buffer for pH adjustment, or a preservative for preventing microbial development (e.g., phenylmercuric nitrate, thimerosal, benzalkonium chloride, phenol, cresol, benzyl alcohol, or the like). The method for treating or preventing Alzheimer's disease by using the composition of the present disclosure includes administering a pharmaceutically effective amount of the composition. The pharmaceutically effective amount may be easily determined by a person skilled in the art according to factors well known in the art, including the kind of disease, age, body weight, health status, sex of a subject (patient), drug sensitivity of a subject (patient), the route of administration, method of administration, number of times of administration, period of treatment, mixing, drug(s) used in combination.

Another aspect of the present disclosure pertains to a method for treatment of a disease caused by amyloid β accumulation and/or aggregation (e.g., Alzheimer's disease and the like), the method comprising directly transplanting to a disease legion a therapeutically effective amount of a composition containing brain cells into which Foxa2 and Nurr1 are introduced. For transplantation and cell culturing, any method known in the art may be employed.

As used herein, a "therapeutically effective amount" of cells is an amount sufficient to arrest or ameliorate the physiological effects in a subject caused by Alzheimer's disease. The therapeutically effective amount of cells used will depend on the needs of the subject (patient), the subject's age, physiological condition, and health, the desired therapeutic effect, the size of the area of tissue that is to be targeted for therapy, the extent of pathology, and the chosen route of delivery. Cells may also be administered to more than one site in a given target tissue, with multiple small grafts of low cell doses. The cells of the present disclosure may be completely dissociated before transplantation, such as to create a suspension of single cells, or nearly completely dissociated before transplantation, such as to create small aggregates of cells. The cells may be administered in a manner that allows them to graft or migrate to the intended tissue site and reconstitute or regenerate a functionally deficient area.

A suitable range of cells that can be administered to achieve a therapeutic effect may be determined according to subjects or patients within a typical knowledge of a person skilled in the art. For example, about 100 to 100,000,000 cells may fall within the suitable range. A low dose may be ineffective while a high dose may incur a side effect. Preferably, 100,000 to 50,000,000 cells may be administered.

However, the dose can be appropriately determined by a physician considering the type of dosage form, administration method, patient's (subject's) age, weight, symptoms, and so on.

A suitable dosage amount of the vaccine composition of the present disclosure may vary depending on pharmaceutical formulation methods, administration methods, the subject's (patient's) age, body weight, sex, pathogenic state, diet, administration time, administration route, an excretion rate and sensitivity for a used pharmaceutical composition. Generally, a skilled physician may determine and prescribe an effective dosage for treatment of interest in an easy manner. Preferably, the pharmaceutical composition of the present disclosure contains a viral vector or viral gene in an amount of $1\times10^5$-$1\times10^{13}$ vg/μl and may be administered one to five times with a daily dose of $1\times10^5$-$1\times10^{16}$ vg/dose. For a persistent effect, administration may be repeated in a similar manner after several months to years.

In the present disclosure, the composition may take a form of the medicinal preparations described above.

As used herein, the term "gene therapy product" refers to a medicine that is designed to deliver a genetic material or a vector carrying a genetic material to the human body for the purpose of treating a disease.

Pharmaceutically acceptable carriers for use in the composition of the present disclosure which can be applied as a gene therapy product are suitably sterile and biocompatible and include saline, sterile water, Ringer's solution, buffered saline, albumin injection solution, dextrose solution, maltodextrin solution, glycerol, ethanol, and a combination thereof. Other conventional additives such as antioxidants, buffers, or bacteriostatic agents may be added as necessary. In addition, a diluent, a dispersing agent, a surfactant, a binder and a lubricant may further be added to the composition of the present disclosure to thereby prepare an injectable formulation such as an aqueous solution, a suspension or an emulsion, or a pill, capsule, granule or tablet formulation. Furthermore, a target organ-specific antibody or ligand bound to the carrier may be used so that the composition can act specifically in the target organ.

The aforementioned content may be applied to the composition employing a vector expressing Nurr1 and Foxa2, but not brain cells expressing Nurr1 and Foxa2, if necessary, with suitable modifications.

Also, the present disclosure provides a method for prevention or treatment of Alzheimer's disease, the method comprising administering to a subject a therapeutically effective amount of a composition containing brain cells having Nurr1 and Foxa2 introduced thereinto.

All the disclosure described above for the composition for prevention or treatment of Alzheimer's disease can be applied to a method for prevention or treatment of Alzheimer's disease without limitations or with modifications if necessary.

Advantageous Effects

Traits and advantages of the present disclosure are summarized as follows:

(a) The present disclosure provides an amyloid β accumulation and/or aggregation inhibitor comprising a vector carrying Nurr1 and Foxa2 genes.

(b) The present disclosure provides an amyloid β accumulation and/or aggregation inhibitor comprising neurons, neuronal stem cells, or glia having Nurr1 and Foxa2 genes introduced thereinto.

(c) The present disclosure provides an inhibitor against the expression of inflammasomes, complements, chemokines (CCL3 and CCL4), inflammatory cytokines (IL-1β and TNF-α), apolipoprotein E (ApoE), nuclear factor kappa-light-chain-enhancer of activated B cells (NFκB), or asparaginyl endopeptidase (AEP), the inhibitor comprising a vector carrying Nurr1 and Foxa2 genes.

(d) The present disclosure provides an inhibitor against the expression of inflammasomes, complements, chemokines (CCL3 and CCL4), inflammatory cytokines (IL-1β and TNF-α), apolipoprotein E (ApoE), nuclear factor kappa-light-chain-enhancer of activated B cells (NFκB), or asparaginyl endopeptidase (AEP), the inhibitor comprising neurons, neuronal stem cells, or glia having Nurr1 and Foxa2 genes introduced thereinto.

(e) The present disclosure provides a composition for prevention or treatment of a disease caused by amyloid β accumulation and/or aggregation, the composition comprising a vector carrying Nurr1 and Foxa2 genes.

(f) The present disclosure provides a composition for prevention or treatment of a disease caused by amyloid β accumulation and/or aggregation, the composition comprising neurons, neuronal stem cells, or glia having Nurr1 and Foxa2 genes introduced thereinto.

(g) The present disclosure provides a composition for inhibition of cellular senescence caused by amyloid β accumulation and/or aggregation, the composition comprising a vector carrying Nurr1 and Foxa2 genes.

(h) When used, the composition of the present disclosure can be applied to the prevention or treatment of a neurodegenerative disease caused by amyloid β accumulation and/or aggregation, such as Alzheimer's disease.

The present disclosure may be variously modified and include various exemplary embodiments in which specific exemplary embodiments will be described in detail hereinbelow. However, it shall be understood that the specific exemplary embodiments are not intended to limit the present disclosure thereto and cover all the modifications, equivalents and substitutions which belong to the idea and technical scope of the present disclosure.

Terms used herein are defined as follows.

The term "brain cells" refers to cells present in the brain and include neurons (nerve cells), neuronal stem cells, and glia.

The term "nerve cells" are cells in the nervous system and may be interchangeably used with "neurons" or "neuronal cells".

The term "glia" accounts for the most abundant among cells present in the brain and includes astrocytes and microglia.

Astrocytes are involved in neuroprotection, nutrient provision, and inflammation and microglia are a cell population responsible for inflammation in the brain and playing an important role in brain disease such as Alzheimer's disease.

The "transduction" is a phenomenon in which a genetic trait is transferred from a cell to another cell via a bacteriophage, thereby introducing the genetic trait to the latter. When a bacteriophage infects a certain type of bacterium, phage DNA binds to host DNA, and as the phage is removed from the bacterium due to bacteriolysis, it may take out a part of the host DNA while losing a part of its own DNA instead. When the phage infects another bacterium, the former host gene is newly introduced into the bacterium, and therefore, the bacterium exhibits a new trait. The term "transduction" used in biological research generally refers to the overexpression of a specific exogenous gene in a target cell using a viral vector.

As used herein, the "inhibiting accumulation and/or aggregation" is intended to encompass inhibiting aggregation by suppressing the production of amyloid β and inhibiting accumulation by degrading already produced amyloid β.

As used herein, the term "subject" may refer to a vertebrate to be tested for treatment, observation or experiments, preferably a mammal, for example, a cow, a pig, a horse, a goat, a dog, a cat, a rat, a mouse, a rabbit, a guinea pig, a human, etc.

"Tissue or cell sample", as used herein, means a collection of similar cells obtained from a tissue of a subject or patient. Sources of tissue or cell samples may include solid tissues from fresh, frozen and/or preserved organ or tissue samples or biopsies or aspirates; blood or any blood component; cells at any time of pregnancy or development in the subject. Tissue samples may also be primary or cultured cells or cell lines.

The "treatment" used herein refers to an approach to obtain a beneficial or a desired clinical result. For purposes of the present disclosure, beneficial or desired clinical results include, but are not limited to, alleviation of symptoms, reduction in the extent of disease, stabilization (i.e., not worsening) of the disease state, delay or deterrence of disease progression, beneficial changes, palliation or transient relief (either in part or entirely) of disease states, whether or not detectable. Also, "treatment" may mean increasing the survival rate compared to the expected survival rate when not receiving treatment. Treatment refers to both therapeutic treatment and prophylactic or preventative measures. Such treatments include treatments required for disorders that have already occurred as well as disorders to be prevented. The term "palliating" disease refers to reducing the extent of a disease state and/or an undesired clinical symptom, and/or extending or prolong the time course of disease progression.

The term "cell therapy product" refers to a medicine (U.S. FDA regulations) used for the purpose of treatment, diagnosis and prophylaxis using cells and tissues prepared through isolation from a human, culturing and special homogenization, that is, a medicine used for the purpose of treatment, diagnosis and prophylaxis through a series of actions of proliferating and selecting living autologous, allogenic or xenogenic cells in vitro to restore the functions of cells or tissues, or changing biological characteristics of cells by another method. Cell therapy products are mainly classified into somatic cell therapy products and stem cell therapy product, depending on a differentiation level of the cells.

"Mammals" for therapeutic purposes refers to any animal classified as mammals, including humans, livestock and farm livestock and zoos, sports or pet animals such as dogs, horses, cats, cattle, monkeys. Preferably the mammal is a human.

As used herein, the term "gene therapy product" refers to a medicine that is designed to deliver a genetic material or a vector carrying a genetic material to the human body for the purpose of treating a disease.

The term "administration" used herein means the introduction of the composition of the present disclosure to a patient by any suitable method, and an administration route of the composition of the present disclosure may vary as long as the composition can reach desired tissue, and it may be any one of various routes including oral and non-oral routes. The composition of the present disclosure may be administered intraperitoneally, intravenously, intramuscularly, subcutaneously, intradermally, orally, locally, intranasally, intrapulmonarily or intrarectally, but the present disclosure is not limited thereto.

The term "effective dose" means an amount necessary to delay or entirely stop the onset or progression of the particular disease to be treated. In the present invention, the composition may be administered in a pharmaceutically effective dose. It will be apparent to those skilled in the art that a suitable total daily dose may be determined by the practitioner within the correct medical judgment.

To determine a therapeutically effective dose for a particular subject or patient, various factors including whether other agents are used, age, body weight, general health status, sex, diet, administration time, administration route, secretion rate of a composition and treatment period and similar factors well known in the medical field are preferably taken into consideration for the purpose of the present disclosure.

All technical terms used in the present disclosure are used in the sense that they are generally understood by those of ordinary skill in the related art of the present disclosure unless otherwise defined. In addition, preferred methods or samples are described in this specification, but similar or equivalent ones are also included in the scope of the present disclosure. The contents of all publications referred to in this specification are incorporated herein by reference in their entirety.

EXAMPLES

Example 1: Materials and Methods (1) Cell Culture
1) Glial Culture

Primary cultures for mixed astrocytes and microglia were derived from the ventral midbrains (VMs) (imprinting control region (ICR)) of mice pups on postnatal day 1, using the protocol previously described (Saura J (2007) Microglia in astroglial cultures: a cautionary note. J Neuroinflammation 4: 26). Briefly, VMs were removed, triturated in Dulbecco's modified Eagle's medium (DMEM; Life Technologies) containing 10% fetal bovine serum (FBS; HyClone, Logan, Utah), and plated in 75-cm² T-flasks. When cell confluence reached 80-90%, the glia were harvested with 0.1% trypsin and prepared for use by plating on culture surfaces.

Pure astrocytes were isolated from mouse VMs on postnatal day 5-7 and cultured in an astro-medium (Heinrich C, Gascon S, Masserdotti G, Lepier A, Sanchez R, Simon-Ebert T, Schroeder T, Gotz M, Berninger B (2011) Generation of subtype-specific neurons from postnatal astroglia of the mouse cerebral cortex. Nat Protoc 6: 214-228). After removing microglia by gently shaking, cells were harvested and re-plated in poly-d-lysine (PDL)-coated dishes. BV2 microglia were cultured in DMEM supplemented with 10% FBS (Blasi E, Barluzzi R, Bocchini V, Mazzolla R, Bistoni F (1990) Immortalization of murine microglia by a v-raf/v-myc carrying retrovirus. J Neuroimmunol 27: 229-237).

2) Neuronal Progenitor Cell (NPC) Culture

NPCs with a neurogenic potential were cultured from the VM (ICR) of mouse embryos on embryonic day 10.5 or Sprague-Dawley rat mouse embryos on embryonic day 12. VM-NPCs were expanded in a serum-free N2 medium supplemented with mitogens basic FGF (bFGF) (20 ng/ml; R&D Systems) and epithelial growth factor (EGF) (20 ng/ml; R&D Systems, only for mouse cells only) to the confluence of 70% or higher (usually for 3-4 days) and then passaged. After additional NPC culturing, the cells were harvested for co-culture and other experiments or directly induced to differentiate by withdrawing the mitogens (in CM treatment experiments).

3) Astrocyte Culture

Astrocytes were isolated from mouse or rat VMs or cortices (Ctx) on postnatal day 5-7 and cultured in an astro-medium. VMs were removed, triturated in DMEM (Life Technologies) containing 10% FBS (HyClone), and plated in 75-cm² T-flasks. When cell confluence reached 80-90%, cells were harvested with 0.1% trypsin and passaged on a poly-D-lysine (PDL)-coated culture surface (MilliporeSigma). Four to six days later, microglia were removed by shaking at 2 g on an orbital shaker. After being grown for 7 days, the astrocytes were harvested for co-culture experiments or further cultured for an additional 8 days in N2 to prepare a conditioned medium (CM). Even after the microglial removal procedure, a small amount of microglia might remain. The astrocyte culture containing the residual microglial population was used in the following experiments. To estimate the effect of contamination by the minor population of microglia, microglia-free astrocyte culture was established by treating the cultures with 0.06% trypsin in DMEM/F12 for 20-30 min after the shaking procedure, and discarding the suspended cells.

4) Co-Culture

VM-NPCs with a neurogenic potential were harvested and mixed with the Ctx-Ast or VM-Ast at a 2:1 ratio (VM-NPCs:astrocytes). The mixed cells were plated and the differentiation of VM-NPCs was directly induced in a serum-free N2 medium.

(2) Virus Production

Lentiviral vectors expressing Nurr1 or Foxa2 under the control of the CMV promoter were generated by inserting the respective cDNAs into the multi-cloning site of pCDH (System Biosciences, Mountain View, Calif.). pGIPZ-shNurr1 and pGIPZ-shFoxa2 lentiviral vectors were purchased from Open Biosystems (Rockford, Ill.). The empty backbone vectors (pCDH or pGIPZ) were used as negative controls. The lentiviruses were produced and used for transducing in vitro cultures as described previously (Yi S H, He X B, Rhee Y H, Park C H, Takizawa T, Nakashima K, Lee S H (2014) Foxa2 acts as a co-activator potentiating expression of the Nurr1-induced DA phenotype via epigenetic regulation. Development 141: 761-772). Titers of the lentiviruses were determined using a QuickTiter™ HIV Lentivirus Quantitation kit (Cell Biolabs, San Diego, Calif.), and 200 µl/well (24-well plates) or 2-ml/6-cm dish with $10^6$ transducing unit (TU)/ml (60-70 ng/ml) were used for each transduction reaction.

For inducing in vivo expression by stereotaxic injection, AAVs expressing Nurr1 or Foxa2 [tagged with hemagglutinin (HA)] under the control of the CMV promoter were generated by subcloning the respective cDNAs into pAAV-MCS vector (Addgene, Cambridge, Mass.). In order to assess the efficiency of transgene expression, GFP-expressing AAVs were generated, as well. Packaging and production of the AAVs (serotype 2) was performed in the Korea Institute of Science and Technology (KIST, Seoul, Korea). AAV titers were determined with a QuickTiter™ AAV Quantitation kit (Cell Biolabs). Co-expression studies were carried out by infecting cells with mixtures of the individual viral preparations (1:1, virus genome copy (gc):virus gc).

(3) Preparation of Glial Conditioned Medium

Primary glia cultures (astrocytes+microglia) expressing Nurr1+Foxa2, Nurr1 alone, Foxa2 alone, or an empty control were prepared by lentiviral transduction.

For use in the co-expression of Nurr1+Foxa2, lentiviruses expressing each transgene separately were mixed 1:1 (v:v) and added to cultures for a control. Total viral volumes and titers in the cultures expressing Nurr1 or Foxa2 alone were adjusted to be the same as those of the co-transduced cultures by adding control viruses. A fresh medium was added 3 days after transduction, and media conditioned in the transduced glia were taken twice at regular intervals of 3 days. The conditioned media (CM) were filtered at 0.45 µm and stored at −80° C. until use.

(4) Immunostaining

Cultured cells and cryosectioned brain slices were stained with the following primary antibodies: Nurr1 (1:500, rabbit, embryonic day 20, Santa Cruz Biotechnology, Dallas, Tex. and 1:1,000, mouse, R&D Systems); Foxa2 (1:500, goat, Santa Cruz); GFP (1:2,000, rabbit, Life Technologies); GFAP (1:200, mouse, MP Biomedicals, Santa Ana, Calif.); Iba-1 (1:200, rabbit, Wako), NeuN (1:100, mouse, EMD Milipore); Amyloid beta (6E10) (1:1000, mouse, Biolegend); Amyloid beta (D54D2) (1:500, rabbit, Cell signaling technology); sox2 (1:500, rabbit, Invitrogen.); UGT1A1 (1:1000, rabbit, Abcam); and Gal C (1:500, rabbit, Abcam).

The cultured cells were fixed with 4% paraformaldehyde (PFA) in PBS and blocked for 40 min with 0.3% Triton X-100 and 1% BSA before being incubated overnight at 4° C. with the primary antibodies. For visualization, a secondary antibody was tagged with Cy3 (1:200, Jackson Immunoresearch Laboratories) or Alexa Fluor 488 (1:200, Life Technologies). The immunostained cells were mounted with VECTASHIELD and DAPI mounting solution (Vector Laboratories) and images of epifluorescence microscopy (Leica) and confocal microscopy (Leica PCS SP5) were obtained.

Staining with thioflavin S (1 mg/mL, Sigma) was performed as follows. First, mice were sacrificed. After being excised from the mice, the brains were mounted on glass slides and completely dried. The slides were washed with 70% ethanol for 1 min and then with 80% ethanol for 1 min. The slide was stained in thioflavin S solution (1% in 80% ethanol) that had been filtered for 15 min (0.2 µm filter). In this regard, the thioflavin S and the stained slide should be protected from light. Then, the slide was washed for 1 min with 80% ethanol and then for 1 min with 70% ethanol before washing with two exchanges of distilled water. A coverslip was mounted on the slide in an aqueous mounting medium and allowed to dry in the dark for at least two hours, followed by sealing the coverslip with clear nail polish. The slide was stored at 4° C. in the dark.

(5) Congo Red Staining

Congo red is used for staining in amyloidosis.

Congo red staining was performed as follows. A deparaffinized brain tissue slice was stained for 30 to 60 min in an aqueous Congo red solution. The slice was washed with distilled water and slightly dipped two or three times in an alkaline alcohol solution. Washing in tap water was followed by counterstaining with hematoxylin. The slice was washed again in tap water and macerated for 30 sec in ammonia water (several drops of ammonium hydroxide in tap water). After washing in tap water for 5 min, the slice was dehydrated in alcohol. Observation was made under a microscope.

(6) Messenger RNA Expression Analysis

Total RNA preparation, cDNA synthesis, and RT-PCRs were carried out using conventional methods. For total RNA preparation, a typical RNA isolation protocol using Trizol Reagent (Invitrogen, Carlsbad, Calif., USA) was employed. cDNA was synthesized using Superscript kit (Invitrogen). Real-time PCR was performed on a CFX96™ Real-Time System using iQ™ SYBR green supermix (Bio-Rad, Hercules, Calif.). Gene expression values were normalized to those of GAPDH. Information on primers is given in Table 1, below. High-throughput gene expression profiling for oxidative stress genes was done by a mouse oxidative stress PCR array (cat. 330231 PAMM-065ZA) using an $RT^2$ Profiler™ PCR Array (Qiagen, Gaithersburg, Md.).

TABLE 1

| MOUSE PRIMER | | |
| --- | --- | --- |
| GAPDH (F) | TIC AGC TCT GGG ATG ACC TT | SEQ ID NO. 1 |
| GAPDH (R) | CTC ATG ACC ACA GTC CAT GC | SEQ ID NO. 2 |
| BDNF (F) | GIG ACA GTA TTA GCG AGT GGG | SEQ ID NO. 3 |
| BDNF (R) | GGG TAG TIC GGC ATT GC | SEQ ID NO. 4 |
| GDNF (F) | AAC ATG CCT GGC CTA CTT TG | SEQ ID NO. 5 |
| GDNF (R) | GAC TTG GGT TTG GGC TAT GA | SEQ ID NO. 6 |
| SHH (F) | GGA TGC GAG CTT TGG ATT CAT AG | SEQ ID NO. 7 |
| SHH (R) | GGA AGA TCA CAA ACT CCG AAC | SEQ ID NO. 8 |
| ARG-1 (F) | TAT CGG AGC GCC ITT CTC TA | SEQ ID NO. 9 |
| ARG-1 (R) | ACA GAC CGT GGG TIC TIC AC | SEQ ID NO. 10 |
| MME (F) | CTA CCG GCC AGA GTA TGC AG | SEQ ID NO. 11 |
| MME (R) | TIC TTG CGG CAA TGA AAG GC | SEQ ID NO. 12 |
| MMP14 (F) | AGG AGG AGA CGG AGG TGA TC | SEQ ID NO. 13 |
| MMP14 (R) | GTC CCA TGG CGT CTG AAG AA | SEQ ID NO. 14 |
| IDE (F) | GCT GAT GAC TGA AGT GGC CT | SEQ ID NO. 15 |
| IDE (R) | CAA TAT GCA GCC GIG ACA GC | SEQ ID NO. 16 |
| ECE2 (F) | AGA CTT CCT TCG GCA CTT CG | SEQ ID NO. 17 |
| ECE2 (R) | ACC ACA CCT CAC ATA GCT GC | SEQ ID NO. 18 |
| TNFa (F) | AGA TGT GGA ACT GGC AGA GG | SEQ ID NO. 19 |

TABLE 1-continued

MOUSE PRIMER

| | | | |
|---|---|---|---|
| TNFa (R) | CCC ATT TGG GAA CTT CTC CT | SEQ ID NO. | 20 |
| IL-1b (F) | TGT TGA TGT GCT GCT GCG A | SEQ ID NO. | 21 |
| IL-1b (R) | AAG TTG ACG GAC CCC AAA ATA T | SEQ ID NO. | 22 |
| INOS (F) | CGT ACC GGA TGA GCT GIG AAT T | SEQ ID NO. | 23 |
| INOS (R) | GCC ACC AAC AAT GGC AAC A | SEQ ID NO. | 24 |
| IL-6 (F) | TGA AGG ACT CTG GCT TTG TCT | SEQ ID NO. | 25 |
| IL-6 (R) | ATG GAT GCT ACC AAA CTG GAT | SEQ ID NO. | 26 |
| ASC (F) | CAC CAG CCA AGA CAA GAT GA | SEQ ID NO. | 27 |
| ASC (R) | CTC CAG GTC CAT CAC CAA GT | SEQ ID NO. | 28 |
| NLRP3 (F) | ATG CTG CTT CGA CAT CTC CT | SEQ ID NO. | 29 |
| NLRP3 (R) | GTT TCT GGA GGT TGC AGA GC | SEQ ID NO. | 30 |
| Casp1 (F) | CAC AGC TCT GGA GAT GGT GA | SEQ ID NO. | 31 |
| Casp1 (R) | GGT CCC ACA TAT TCC CTC CT | SEQ ID NO. | 32 |
| Nurr1 (F) | CAT GGA CCT CAC CAA CAC TG | SEQ ID NO. | 33 |
| Nurr1 (R) | ACA GGG GCA TTT GGT ACA AG | SEQ ID NO. | 34 |
| rFoxa2 (F) | GCT CCC TAC GCC AAT ATC AA | SEQ ID NO. | 35 |
| rFoxa2 (R) | CCG GTA GAA AGG GAA GAG GT | SEQ ID NO. | 36 |

(7) Immunoprecipitation (IP) and Western Blot (WB) Analysis

Interaction between Nurr1 and Foxa2 (present in mouse VM tissue at 10 weeks of age) was assayed by IP. Tissues were lysed in IP lysis buffer (Thermo Scientific, Waltham, Mass.) supplemented with protease inhibitors. Lysates were incubated for 18-24 hours at 4° C. with anti-Nurr1 (1:1,000, mouse, R&D Systems) or anti-Foxa2 (1:1,000, goat, Santa Cruz Biotechnology). The mixtures were shaken with magnetic beads (Life Technologies) for 1-2 hours at room temperature. After washing, immunoprecipitated proteins were eluted in sample buffer and subjected to Western blot analysis with anti-Foxa2 (1:1,000, goat, Cell Signaling) or anti-Nurr1 (1:500, mouse, R&D Systems): Caspase-1 (1:1000, mouse, Santa Cruz Biotechnology), ASC (1:1500, mouse, Santa Cruz Biotechnology), β-actin (1:2000, mouse, Invitrogen), p-IKKα/β(1:1000, rabbit, Cell signaling), p-IkBα(1:1500, rabbit, Cell signaling) p-p65 (1:1000, rabbit, Cell signaling) NFκB (1:2000, rabbit, Cell signaling), PSD95 (1:2000, rabbit, Abcam), Syn1 (1:1500, rabbit, Sigma), and SYPT (1:2000, mouse, Invitrogen)

(8) Animal Care and Experiments

All procedures for 3xFAD animal model experiments were approved by the Institutional Animal Care and Use Committee (IACUC) at Hanyang College of Medicine under the approval number 2018-0047A. In addition, all procedures for 3xFAD animal model experiments were performed in accordance with the Hanyang University Guidelines for the Care and Use of Laboratory Animals. Animals were housed in a specific pathogen-free barrier facility with a 12-h light/dark cycle and maintained on standard chow (5053 PicoLab® Rodent Diet 20). Animal sizes for the experiments were determined according to in vitro assays and a pilot test without previous statistical calculation. Experiments were performed in accordance with the NIH guidelines. To minimize bias, behavioral assays have mostly been assessed by two experimenters in a blinded fashion. Alzheimer's disease transgenic (3xTg-AD) mice at 18 months and 15 months of age (Jackson Laboratory, Maine, USA) were used in the experiments.

In addition, all procedure for 5xFAD animal model experiments were approved by the Institutional Animal Care and Use Committee at the Korea Institute of Science and Technology under the approval number KIST-2019-057.

(9) Stereotaxic AAV Injection into Alzheimer's Disease Model Mice

Alzheimer's disease transgenic (3xTg-AD) mice 18 months and 15 months old (Jackson Laboratory, Maine, USA) were injected with Nurr1-AAV9 (1 µl)+Foxa2-AAV9 (1 µl) ((2 µl, $10^{10}$ vg/µl, Nurr1+Foxa2 group) or control-AAV9 (2 µl, $10^{10}$ vg/µl, control only) over 10 min at the hippocampus (1.5 mm posterior to bregma; ±1 mm lateral to midline; −2 mm ventral to dura) and the intracerebroventricle (ICV) (0.9 mm posterior to bregma; ±1.7 mm lateral to midline; −2.2 mm ventral to dura) under anesthesia induced by Zoleti150 (0.1 mg/kg) mixed with Rompum (93.28 µg/kg). The needle (26 gauge) was left at the injection site for 5-10 min after completion of each injection and then removed slowly. When inaccurate injection at the hippocampus and intracerebroventricle (ICV) positions was confirmed, the mice were excluded from analysis.

(10) Behavior Tests

1) Water Maze Task

Water Maze task, also known as the Morris water maze, is widely used to study spatial learning and memory. Animals are placed in a pool of water that is colored opaque with powdered non-fat milk or non-toxic tempera paint, where they must swim to a hidden escape platform. Because they are in opaque water, the animals cannot see the platform, and cannot rely on scent to find the escape route. Instead, they must rely on external or extra-maze cues. As the animals becomes more familiar with the task, they are able to find the platform more quickly. Developed by Richard G. Morris in 1984, this paradigm has become one of the "gold standards" of behavioral neuroscience.

2) Y-Maze Test

The Y-Maze is widely used to assess behavioral task in preclinical research for studying spatial learning and memory. Animals are placed at the end of one of three arms in a Y-shaped maze, where they determine whether they move left or right at the forked road. This test may be repeated for one animal. An observer records a series of choices of the animals (e.g., numbers of entries into specific arms, a total number of entries into the three arms, a number of entries into the arm left to the animal, a number of entries into the arm right to the animal). The use of Y maze tests includes spontaneous alternation test and recognition memory test. In the spontaneous alternation test, an observer monitors and records whether or not the animals tend to explore a new arm of the maze rather than returning to one that was previously visited (e.g., number of spontaneous alternation). These tests have been shown to be sensitive to hippocampal damage, gene manipulations, and amnestic drugs.

3) Passive Avoidance Test

An apparatus for passive avoidance test comprises an electrical shock generator and an avoidance device. The avoidance device is a dark box made of black acryl (30×

30×30 cm) with aluminum rods provided at regular gaps on the bottom thereof. Through the rods, an electrical shock can be delivered to the paw soles of the animals. On the front outer wall of the box is established a balustrade that is so small in size (5×15 cm) that one animal can barely be placed thereon. A halogen lamp (AC12V-50 W) is installed 45 cm above the balustrade. A small door (5×5 cm) is provided between the balustrade and the avoidance box. The electrical shock generator was the scramble shock generator manufactured by Coulbourn.

In a training trial, as soon as the animal was placed on the balustrade so as for the head to direct outward, the door communicating with the box was open. When the door was open, light was illuminated on the animal through the lamp installed 45 cm above the balustrade. In this condition, the animal exhibited an avoidance response. A second trial was carried out with an interval of 10 seconds between trials when the animal entered the box. This trial was repeated three times. In the third trial, an electrical shock (0.4 mA, 5 sec) was delivered through the aluminum rods placed on the bottom at the moment the animal entered the dark box. The animal was regarded to react only when all the four paws stepped into the box. Twenty-four hours after completion of the training trial, the retention test was performed using the same procedure. This test trial was terminated without electrical shock delivery when the animal entered the box. In both the training trial and the test trial, the response latency taken for the animal to enter the dark box from the balustrade, which is an aversion condition, was recorded as a training or memory result. The response latency is a memory score because the animal does not immediately enter the dark place, but stays long in the bright place if it forms the memory of electrical shock experience upon entry into the dark place from the bright place that the animal tends to avoid.

4) Novel Object Recognition (NOR) Task

The Novel Object Recognition (NOR) task is used to evaluate cognition, particularly recognition memory, in rodent models of CNS disorders. This test is based on the spontaneous tendency of rodents to spend more time exploring a novel object than a familiar one. The choice to explore the novel object reflects the use of learning and recognition memory.

The Novel Object Recognition task is conducted in an open field arena with two different kinds of objects. Both objects are generally consistent in height and volume, but are different in shape and appearance. During habituation, the animals are allowed to explore an empty arena. Twenty-four hours after habituation, the animals are exposed to the familiar arena with two identical objects placed at an equal distance. The next day, the mice are allowed to explore the open field in the presence of the familiar object and a novel object to test long-term recognition memory. The time spent exploring each object and the discrimination index percentage were recorded.

This test is useful for assessing impaired cognitive ability in Alzheimer's disease transgenic strains of mice and evaluating novel chemical entities for their effect on cognition.

(11) Cell Counting and Statistical Analysis

Immunostained and DAPI-stained cells were counted in random areas of each culture coverslip using an eyepiece grid at a magnification of 200× or 400×. Data are expressed as the mean±SEM for all values and statistical tests are justified as appropriate. Statistical comparisons were made using Student's t-test (unpaired or paired) or one-way ANOVA followed by Bonferroni post hoc analysis using SPSS® (Statistics 21; IBM Inc. Bentonville, Ark., USA).

The n, P-values, and statistical analysis methods are indicated in the figure legends. 0.05. A P value less than 0.05 was considered significant.

(12) RNA-SEQ Analysis

RNA sequencing was carried out in Macrogen (Seoul, Korea). After trimming reads having a quality score less than 20 with FastQC and checking the mismatch ratio using Bowtie, all RNA-seq data were mapped to the mouse reference genome (GRCm38/mm 10) using STAR. To measure expression levels of all 46,432 annotated genes, 107,631 transcripts, and 76,131 protein-coding (mRNA) records in the mouse genome (based on NCBI RefSeq annotations Release 105: February 2015), reads mapped to the exons of genes were counted using Htseq-count and the Fragments Per Kilobase of exon per Million fragments mapped (FPKM) value were calculated. Quantile normalization was performed to reduce technical global bias of expression between groups. All data have been deposited into GEO database (GEO: 17 GSE106216).

(13) RT-PCR Analysis

Total RNA was prepared by an RNA isolation protocol using Trizol Reagent (Invitrogen, Carlsbad, Calif., USA). cDNA synthesis was performed using a Superscript kit (Invitrogen). Real-time PCR was carried out on a CFX96™ Real-Time System using iQ™ SYBR green supermix (Bio-Rad, Hercules, Calif., USA). Gene expression levels were determined as normalized values to those of GAPDH. Gene expression profiling for 84 oxidative stress genes was done by a mouse oxidative stress PCR array (cat. 330231 PAMM-065ZA) using an $RT^2$ Profiler PCR ArrayR (Qiagen, Gaithersburg, Md.). Primers information is given in Table 1, above.

Example 2: Results (1) AAV-Mediated Nurr1 and Foxa2 Gene Delivery into Astrocyte in Alzheimer's Disease (AD) Mouse Model Because adeno-associated virus (AAV) is very poorly immunogenic in the human body, AAV9 serotype, which tends to mainly infect glia in the brain, was used to construct a Nurr1/Foxa2 gene delivery system specifically targeting glia. For expressing Nurr1 and Foxa2 genes, a CMV or GFAP promoter was employed. Nurr1+Foxa2-AAV9 was injected into the hippocampus and intracerebroventricle (ICV), which are lesion sites of Alzheimer's disease.

Figure 2:
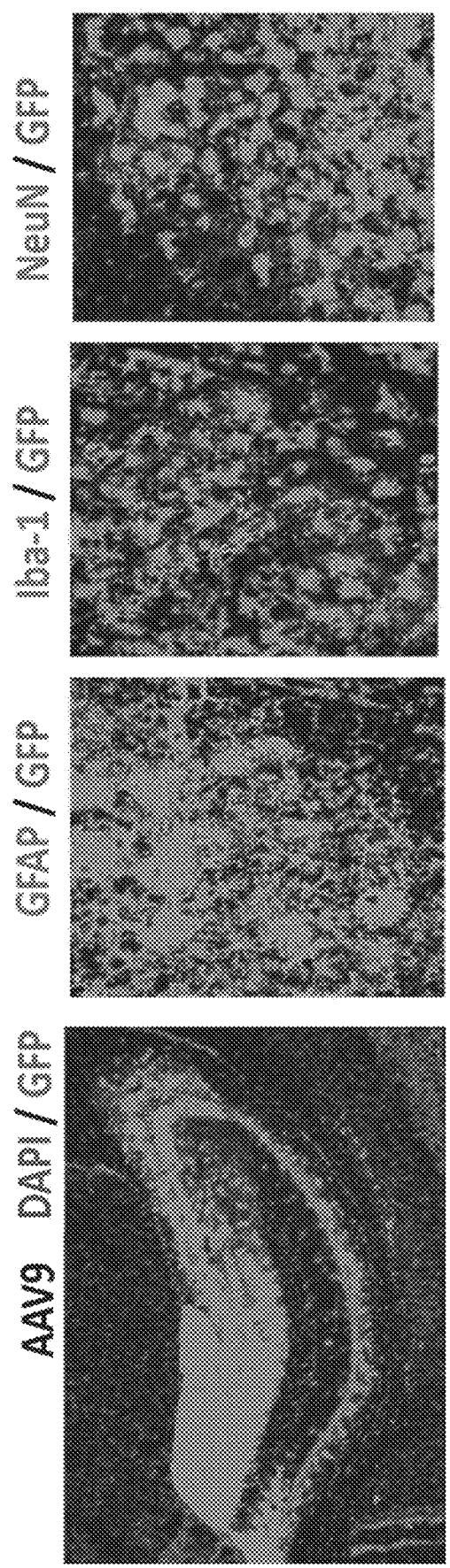
FIG. 2 shows results of a gene delivery test using AAV9 virus (GFP expression levels in the hippocampus and the intracerebroventricle)

Gene delivery using AAV9 was tested. In this regard, the AAV9 that is specific for astrocytes and expresses green fluorescent protein (GFP) under the control of GFAP was injected to both the hippocampus and the intracerebroventricle (ICV) of mice. Three weeks after injection with GFP-AAV9 virus, GFP expression was measured (FIG. 1). As a result of injecting GFP-AAV9 to the hippocampus and the intracerebroventricle (ICV), GFP was expressed across the hippocampus and specifically in GFAP+ astrocytes (FIG. 2). GFAP, NeuN, and Iba1 were used as markers for astrocytes, mature neurons, and microglia, respectively. The co-expression of GFAP and GFP without co-expression of GFP and NeuN or Iba1 indicated that the virus expressed the genes specifically in astrocytes.

(2) Alleviation of Cognitive Impairment (Learning and Memory) by Nurr1/Foxa2 Gene Delivery in Alzheimer's Disease (AD) Mouse Model as Analyzed by Water Maze and Y Maze Behavior Tests Investigation was made to see the effect of glial Nurr1 and Foxa2 expression on the treatment of Alzheimer's disease. In this regard, Nurr1 and Foxa2 were expressed specifically in hippocampal and intracerebroventricular glial cells of 3xFAD mice at 15-18 months of age, which had undergone the onset of Alzheimer's disease by mutagenesis in the three genes APP, PS1, and tau. Mice at 15-18 months of age were considerably old, given that mice live about 24 months on average. Two to three months after delivery of Nurr1 and Foxa2 genes to Alzheimer's disease model mice, the mice were analyzed for cognitive ability.

Alzheimer's disease is a neurodegenerative disease characterized by slow progression of the impairment of memory and cognitive ability. Water Maze and Y Maze tests were carried out as animal tests for Alzheimer's disease. Water Maze and Y Maze tests are both authorized experimental methods representative of efficacy experiments for memory and cognitive ability and used as indicators of behavioral tests for determining the progression of Alzheimer's disease and therapeutic effects on Alzheimer's disease.

Figure 3:
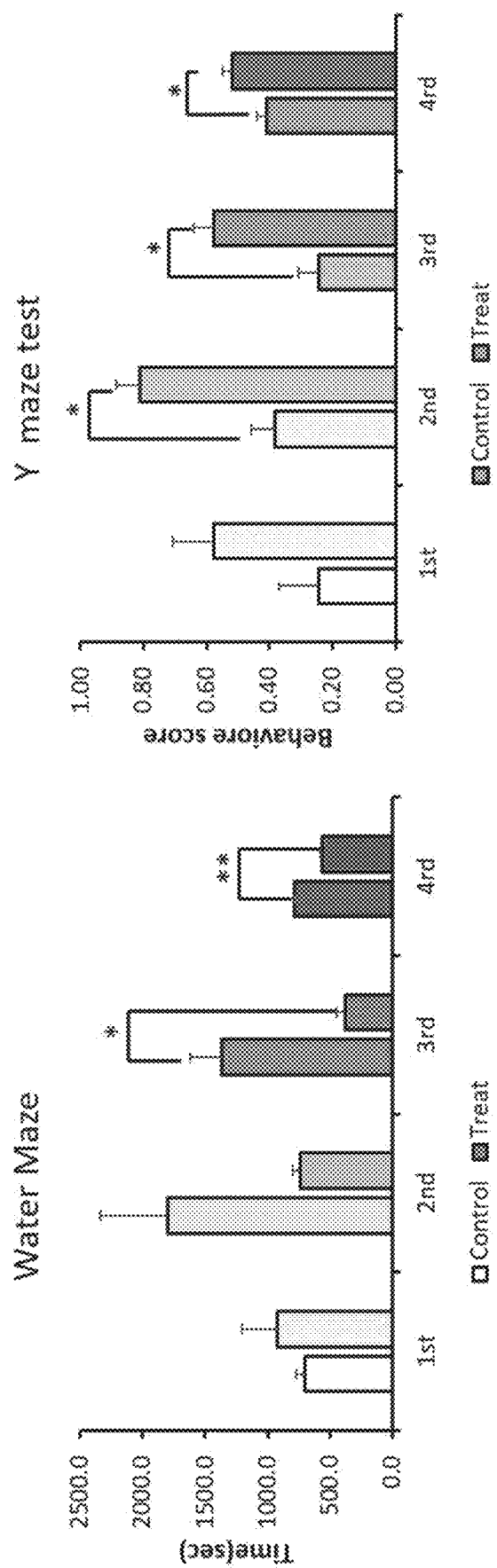
FIG. 3 shows behavior indices of Alzheimer's disease model mice into which Nurr1+Foxa2-AAV9 viruses and control viruses (GFP-AAV9) are introduced, respectively.

About two weeks after injection of Nurr1+Foxa2-AAV9 virus into mice at 15-18 months of age, Water Maze and Y Maze behavioral tests were carried out bi-weekly for two months. Behavioral indices were compared between Alzheimer's disease model mice injected with Nurr1+Foxa2-AAV9 virus and control virus (GFP-AAV9). As a result, the Nurr1+Foxa2-expressed mice exhibited better behavioral indices and faster response speeds, compared to the control mice, indicating that glial expression of Nurr1 and Foxa2 brought about a significant improvement in cognitive activity responsible for learning and memory and thus a therapeutic effect on Alzheimer's disease. That is, the expression of Nurr1 and Foxa2 in brain cells was identified to have a clinical gene therapy effect on Alzheimer's disease (FIG. 3).

(3) Alleviation of Cognitive Impairment (Learning and Memory) by Nurr1/Foxa2 Gene Delivery in Alzheimer's Disease (AD) Mouse Model as Analyzed by Passive Avoidance and Object Recognition Tests Investigation was made to see the effect of glial Nurr1 and Foxa2 expression on the treatment of Alzheimer's disease. In this regard, Nurr1 and Foxa2 were expressed specifically in hippocampal and intracerebroventricular glial cells of 5xFAD mice at 6-8 months of age, which had undergone the onset of Alzheimer's disease by mutagenesis in the three genes APP, PS1, NCT, PEN2, and APH1. One week after delivery of Nurr1 and Foxa2 genes to Alzheimer's disease model mice, the mice were analyzed for cognitive ability.

Alzheimer's disease is a neurodegenerative disease characterized by slow progression of memory and cognitive deficit. Passive avoidance and novel object recognition tests were carried out as animal tests for Alzheimer's disease. Passive avoidance and novel object recognition tests are both authorized experimental methods representative of efficacy experiments for memory and cognitive ability and used as indicators of behavioral tests for determining the progression of Alzheimer's disease and therapeutic effects on Alzheimer's disease.

Figure 4:
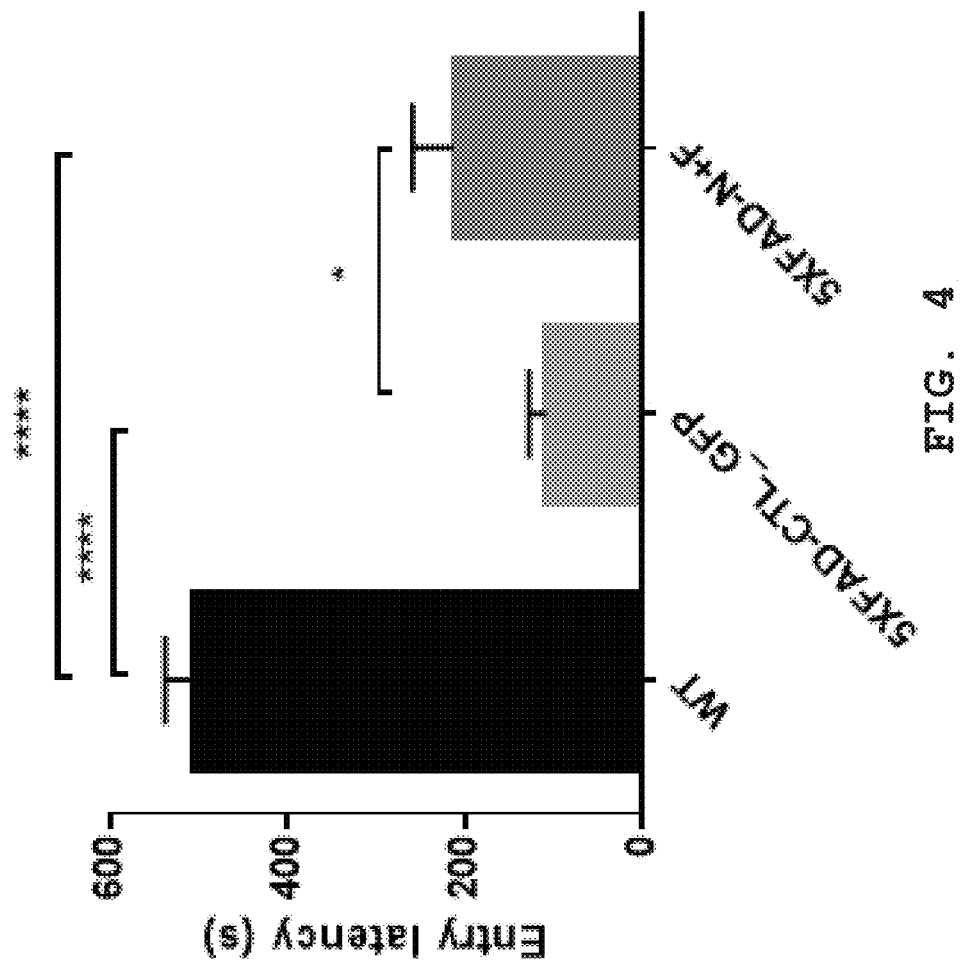
FIG. 4 shows behavior indices of Alzheimer's disease model mice into which Nurr1+Foxa2-AAV9 viruses and control viruses (GFP-AAV9) are introduced, respectively, as analyzed by passive avoidance task.
Figure 5:
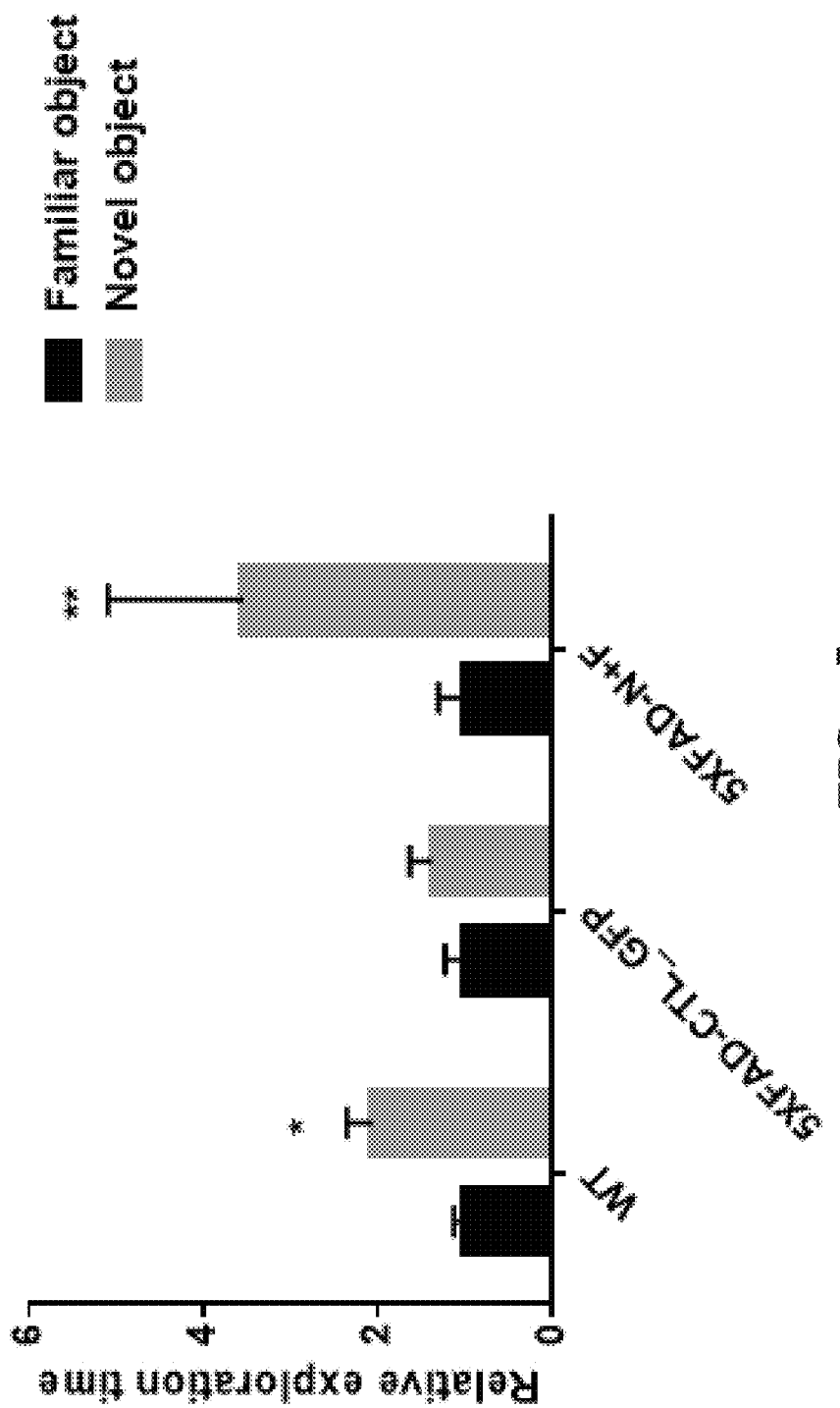
FIG. 5 shows behavior indices of Alzheimer's disease model mice into which Nurr1+Foxa2-AAV9 viruses and control viruses (GFP-AAV9) are introduced, respectively, as analyzed by novel object recognition task.

Novel object recognition test and passive avoidance test were carried out about two weeks and 11 weeks after injection of Nurr1+Foxa2-AAV9 virus into mice at 6-8 months of age, respectively. Behavioral indices were compared between Alzheimer's disease model mice injected with Nurr1+Foxa2-AAV9 virus and control virus (GFP-AAV9). As a result, the Nurr1+Foxa2-expressed mice stayed in the bright place without immediate entry into the dark place in the passive avoidance test and thus exhibited increased entry latency, compared to the control mice (FIG. 4). In addition, the Nurr1+Foxa2-expressed mice restored memory ability, compared to the control mice, in the novel object recognition test (FIG. 5), indicating that glial expression of Nurr1 and Foxa2 brought about a significant improvement in cognitive activity responsible for learning and memory and thus a therapeutic effect on Alzheimer's disease. That is, the expression of Nurr1 and Foxa2 in brain cells was identified to have a clinical gene therapy effect on Alzheimer's disease (FIGS. 4 and 5).

(4) Reduction of Amyloid β Accumulation by Nurr1/Foxa2 Gene Delivery in Alzheimer's Disease (AD) Mouse Model In the brains of patients with Alzheimer's disease, neurofibrillary tangles (NFT) and senile plaques (Aβ plaques) mainly composed of amyloid β (Aβ) peptides are found. Thus, preventing the formation of such NFT and dissociating the aggregates can be used as indices for therapeutic effects on Alzheimer's disease.

Nurr1+Foxa2-AAV9 was used to introduce Nurr1+Foxa2 genes specifically into hippocampal and intracerebroventricular glial cells of 3xFAD mice (in which the onset of Alzheimer's disease was induced by mutagenesis of APP, PS1, and tau) 15 and 18 months of age. Two months after introduction of the genes, fluorescence for amyloid β and protein aggregates (Thioflavin S) was analyzed by immunostaining in the hippocampal region.

Figure 6:
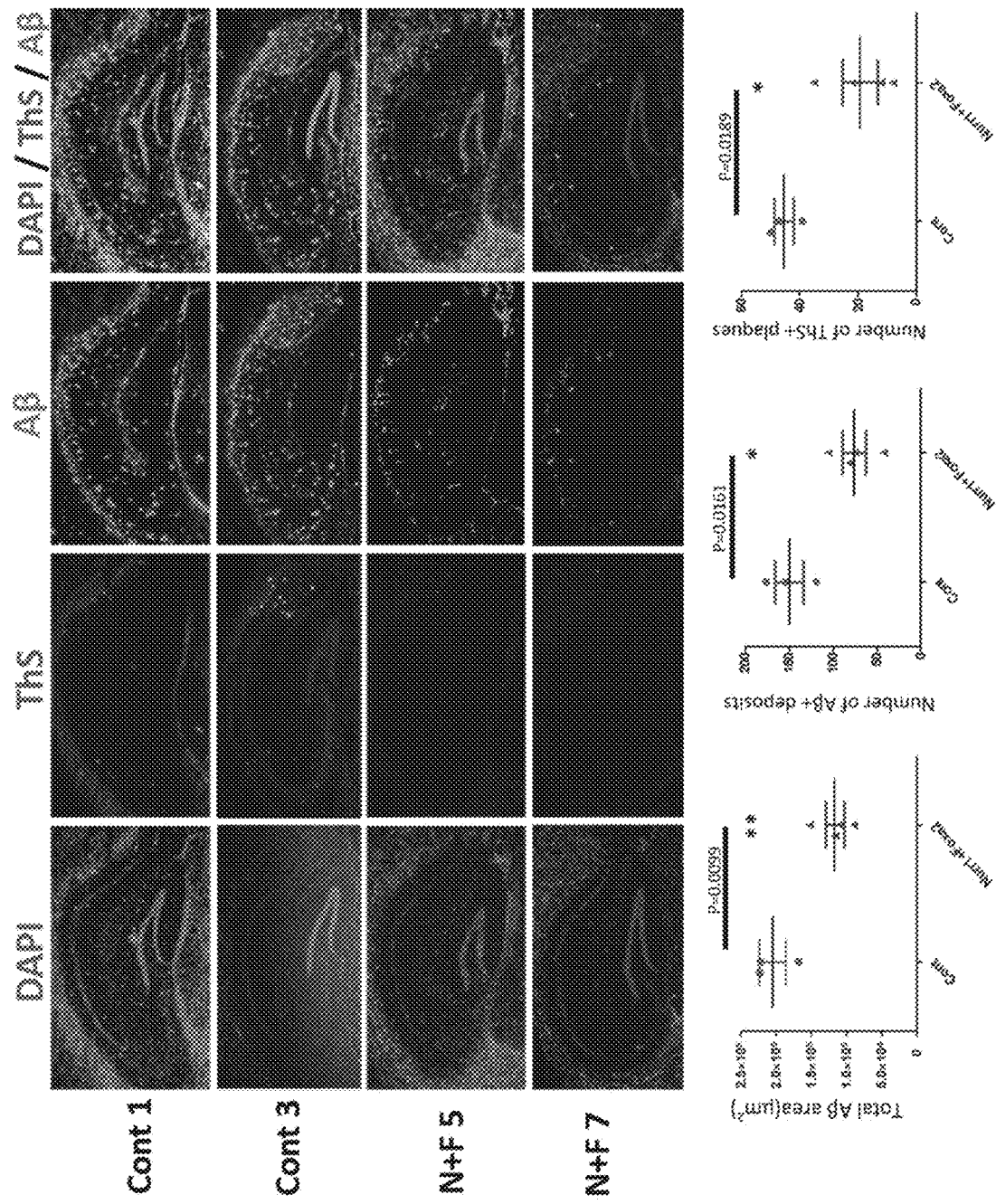
FIG. 6 shows fluorescence of hippocampal amyloid β and protein aggregates (thioflavin S) in Alzheimer's disease model mice into which Nurr1+Foxa2-AAV9 viruses are introduced, as analyzed by immunostaining.

As a result, the markers were detected by immunostaining in the hippocampus of the Nurr1+Foxa2-treated group after about two months. In addition, a significant reduction of amyloid β (Aβ) and neurofibrillary tangles (Thioflavin S) was detected in the Nurr1+Foxa2-treated group as analyzed by immunostaining method (using an amyloid β-specific antibody and Thioflavin S staining) (FIG. 6).

Figure 7:
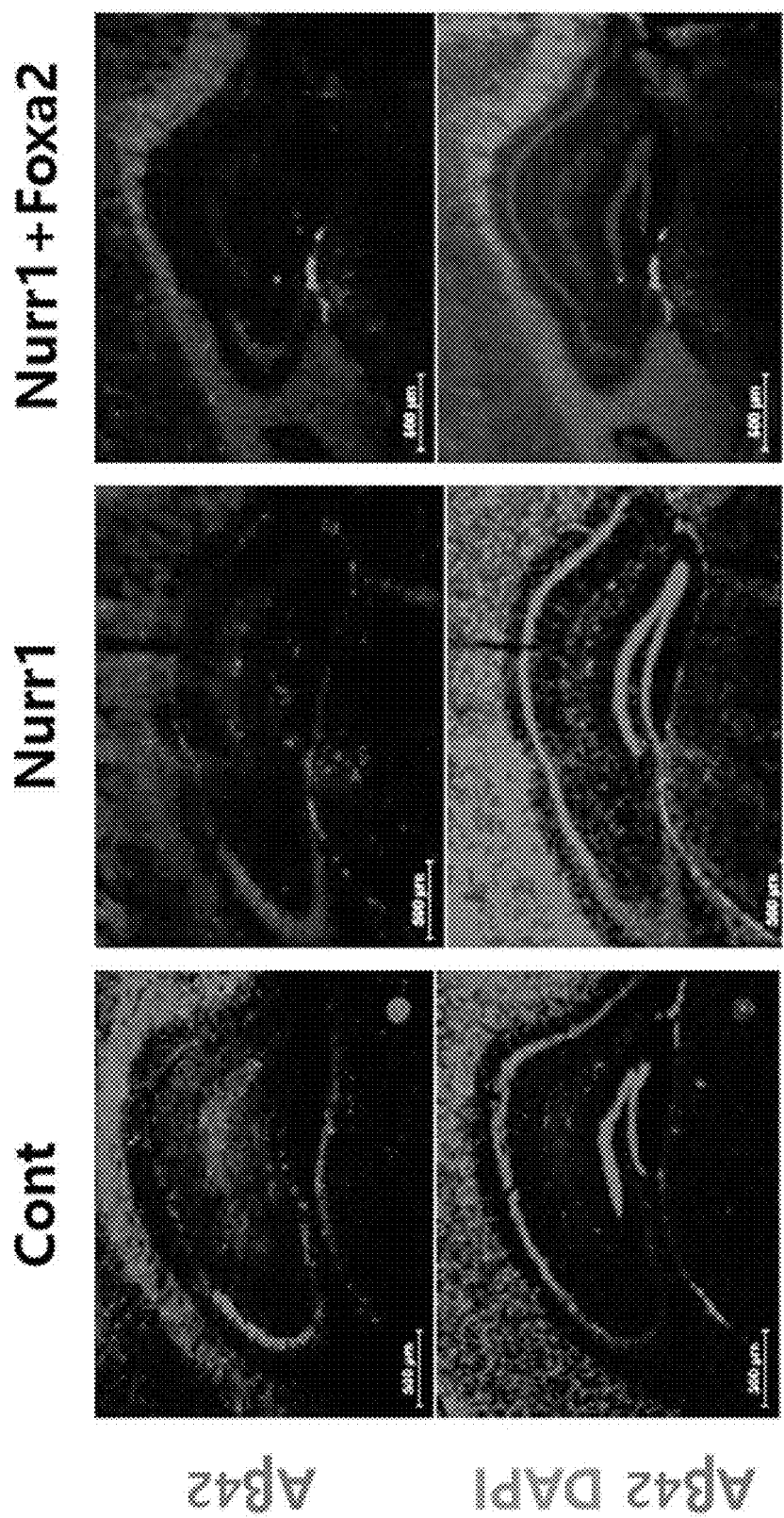
FIG. 7 shows fluorescence of hippocampal amyloid β in Alzheimer's disease model mice into which Nurr1 and Nurr1+Foxa2 genes are introduced, respectively, as analyzed by immunostaining.

Furthermore, the amyloid β (Aβ) accumulation was significantly reduced in the group treated with Nurr1+Foxa2 in combination, compared to the group treated with Nurr1 alone, as analyzed by immunostaining (FIG. 7).

In addition to immunostaining, Congo red staining and Western blot analyses were used to examine the aggregation of amyloid β.

Figure 8:
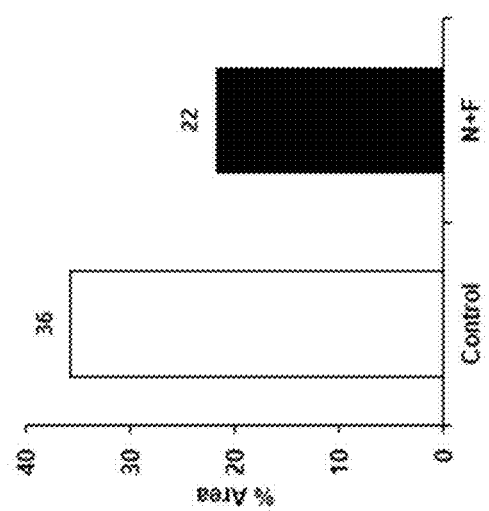
FIG. 8 shows fluorescence of hippocampal amyloid β in Alzheimer's disease model mice into which Nurr1+Foxa2-AAV9 viruses are introduced, as analyzed by Congo red staining.
Figure 8:
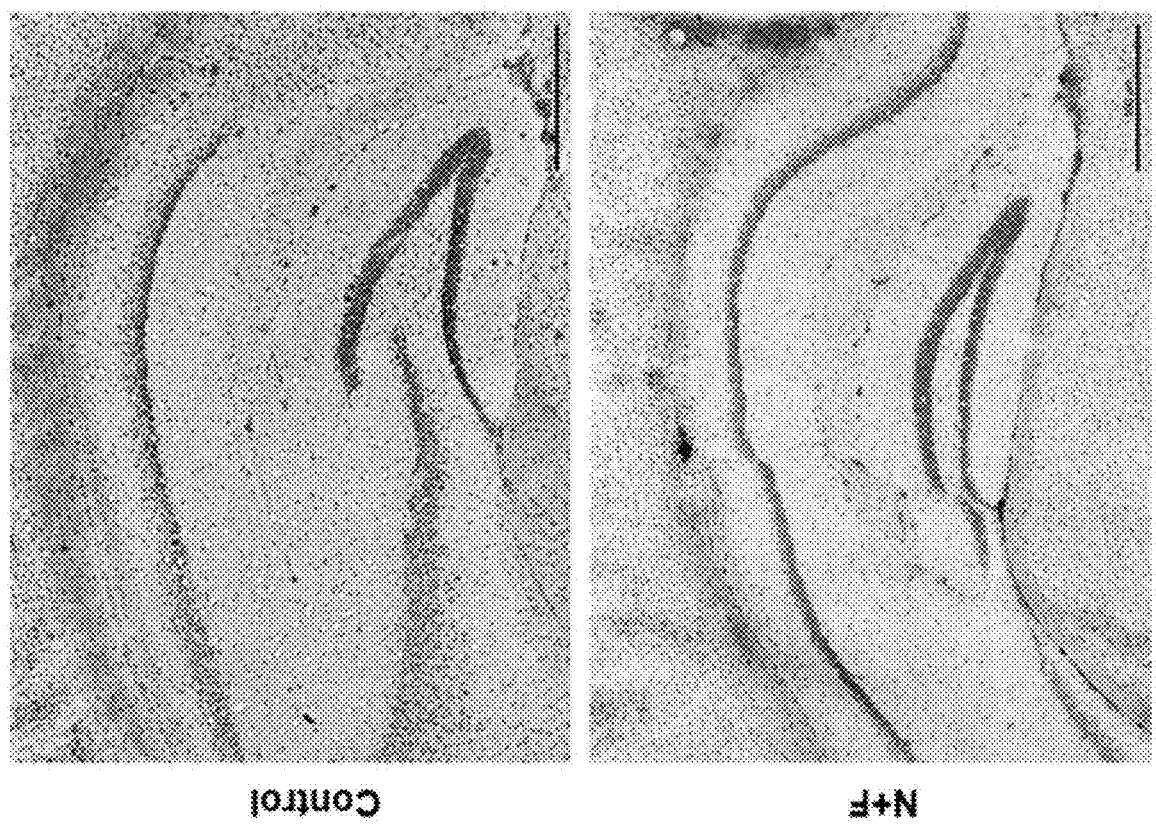

As a result, a significant reduction of amyloid β (Aβ) was observed by Congo red staining in Nurr1+Foxa2-treated group (FIG. 8).

Figure 9:
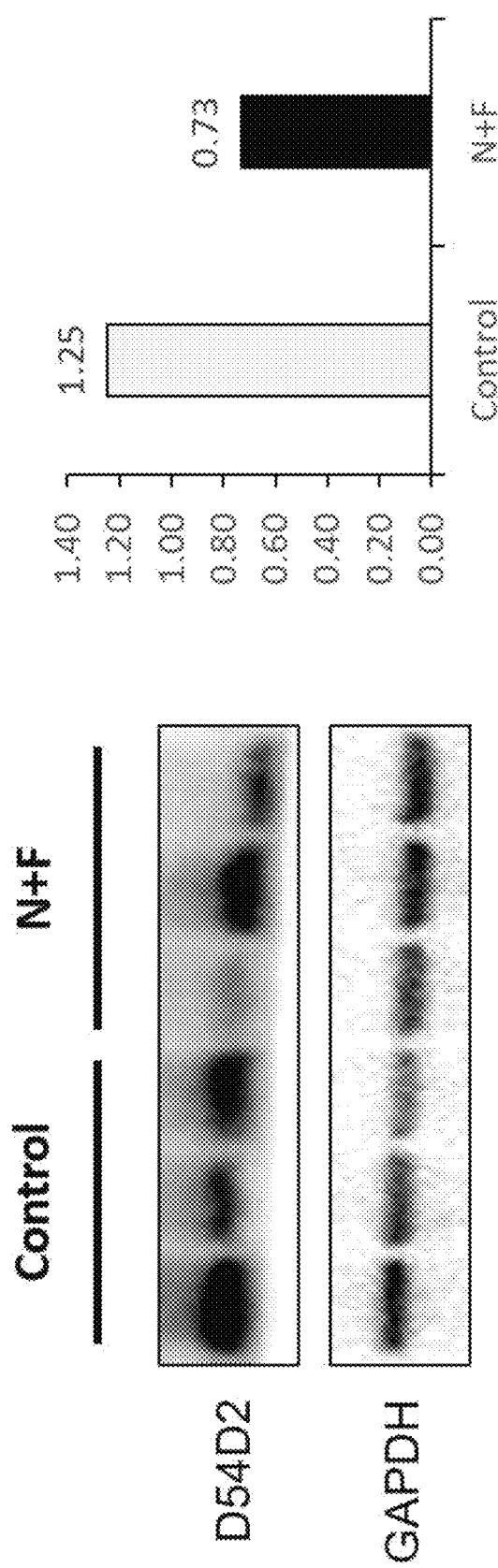
FIG. 9 shows levels of hippocampal amyloid β in Alzheimer's disease model mice into which Nurr1+Foxa2-AAV9 viruses are introduced, as analyzed by western blotting (protein electrophoresis)

Moreover, Western blot analysis (protein electrophoresis) exhibited a significant reduction of amyloid β(D54D2) in the Nurr1+Foxa2-treated group (FIG. 9).

(5) Quantitation of Amyloid β Fibril by Thioflavin T Assay

A thioflavin T assay was carried out to examine whether glial expression of Nurr1+Foxa2 genes promotes disaggregation of amyloid β. For quantitation of amyloid β fibrils, turbidimetry and thioflavin T assays were employed.

Figure 10A:
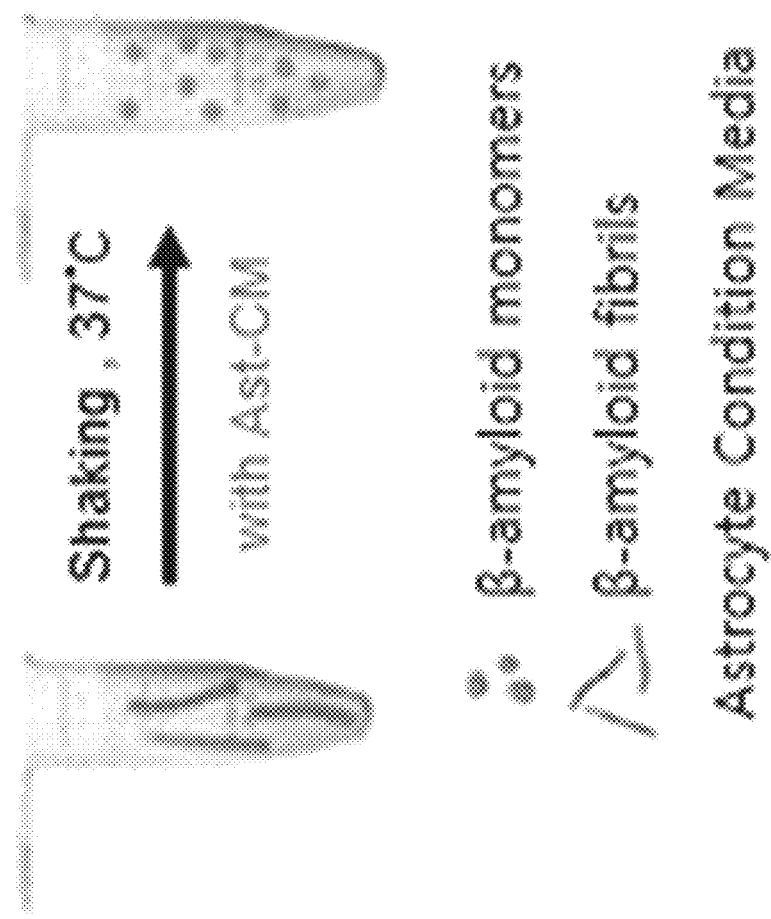
FIG. 10a illustrates a test process for amyloid β disaggregation in which amyloid β fibrils (Aβ fibrils) are quantitated by thioflavin T assay.

FIG. 10a illustrates a test process for amyloid β disaggregation. After a sample was centrifuged at 1000 rpm for 10 min at 37° C., the pellet thus obtained and CM were mixed with amyloid β fibrils so that a part of the amyloid β fibrils degraded into monomers. Thereafter, a ThT assay solution was added so that ThT was attached to the amyloid β fibrils which can be quantitated based on the fluorescence of the attached ThT.

In this regard, a total of 50 μl of a medium where Nurr1+Foxa2-expressed glia had been cultured plus a supernatant of lysate cells (Nurr1+Foxa2), a total of 50 μl of a medium where Nurr1-expressed glia had been cultured plus a supernatant of lysate cells (Nurr1), a total of 50 μl of a medium where control glia had been cultured and a supernatant of lysate cells (Cont), and 50 μl of a medium itself (Media) were each treated by the method above, and then mixed with 200 μl of a ThT assay solution. Here, the ThT assay solution was 25 μM ThT (cat. no. T3516, Sigma- Aldrich) in 10 mM glycine buffer (pH 9.0). Thereafter, amyloid β fibrils were quantitated on the basis of ThT fluorescence (excited at 440 nm) measured by fluorospectrometry at 482 nm.

Figure 10B:
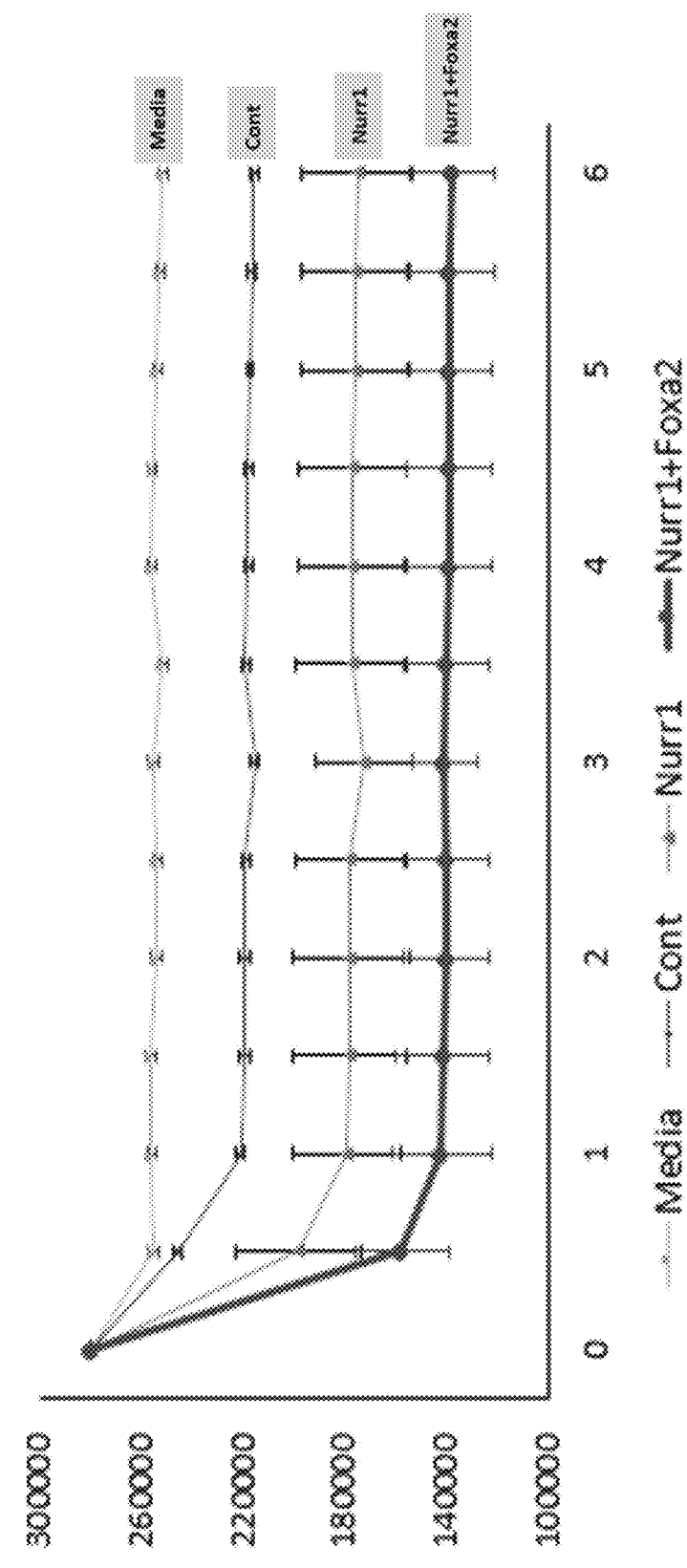
FIG. 10b is a plot of amyloid β fibril (Aβ fibril) levels after experiments for amyloid β disaggregation, illustrating a synergistic effect of the group co-expressing Nurr1 and Foxa2, as measured by thioflavin T assay.
Figure 10C:
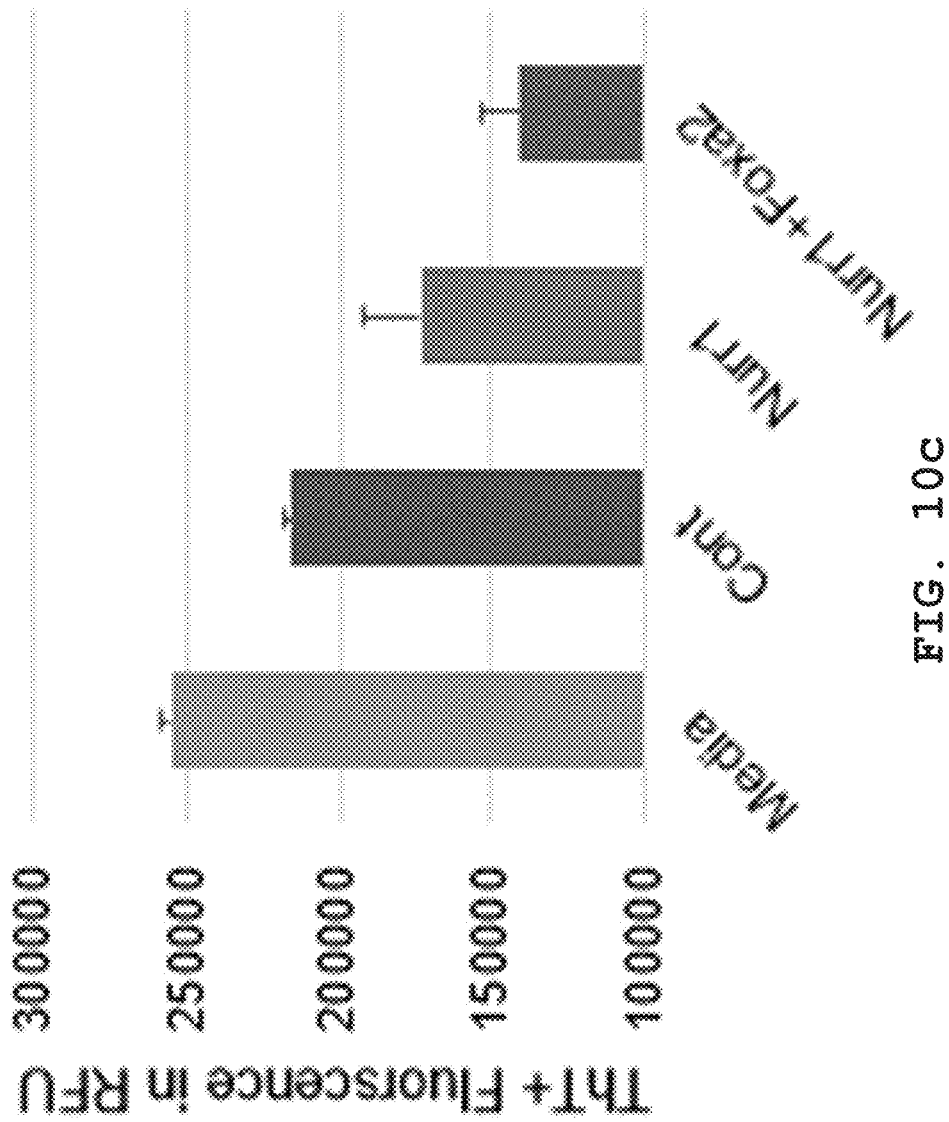
FIG. 10c is a bar graph of amyloid β fibril (Aβ fibril) levels after experiments for amyloid β disaggregation, illustrating a synergistic effect of the group co-expressing Nurr1 and Foxa2, as measured by thioflavin T assay.

An in-vitro amyloid β assay exhibited increased disaggregation of amyloid β in the culture medium sample treated with Nurr1+Foxa2-expressed glia (Nurr1+Foxa2), compared to the other samples (Nurr1-expressed group, Control vector group, Media-treated group) (FIGS. 10b and 10c).

The disaggregation of amyloid β fibrils in the sample treated with a culture of Nurr1+Foxa2-expressed glia was significantly greater than those in the samples treated with the other cultures (Nurr1 solely expressed, Control vector group, Media-treated group). Hence, a culture of Nurr1+Foxa2-expressed glia has a higher effect of promoting amyloid β disaggregation, compared to a culture of the control glia. In light of the effect of the glia expressing Nurr1 solely, the co-expression of Nurr1+Foxa2 was found to have a synergistic effect on amyloid β disaggregation.

(6) Effect of Nurr1+Foxa2 Expression on Amyloid β Disaggregation

After Nurr1+Foxa2 genes were expressed in rodent primary astrocytes with the aid of Lenti virus, mRNA levels of the related genes were measured by RNA-Seq and RT-PCR.

When the glia were cultured to express Nurr1+Foxa2 genes, observation was made of an increase in the expression of enzymes associated with the disaggregation of amyloid β, such as (a) MMp14, (b) MME, (c) MMP2, (d) FOLH1, (e) ECE1, and (f) ACE (Yang, C. N., Wu, M. F., Liu, C. C., Jung, W. H., Chang, Y. C., Lee, W. P., . . . Chan, C. C. (2017). Differential protective effects of connective tissue growth factor against Abeta neurotoxicity on neurons and glia. Hum Mol Genet, 26(20), 3909-3921. doi: 10.1093/hmg/ddx278 and Ries, M., & Sastre, M. (2016). Mechanisms of Abeta Clearance and Degradation by Glia. Front Aging Neurosci, 8, 160. doi: 10.3389/fnagi.2016.00160) (FIGS. 11a and 11b).

Figure 11B:
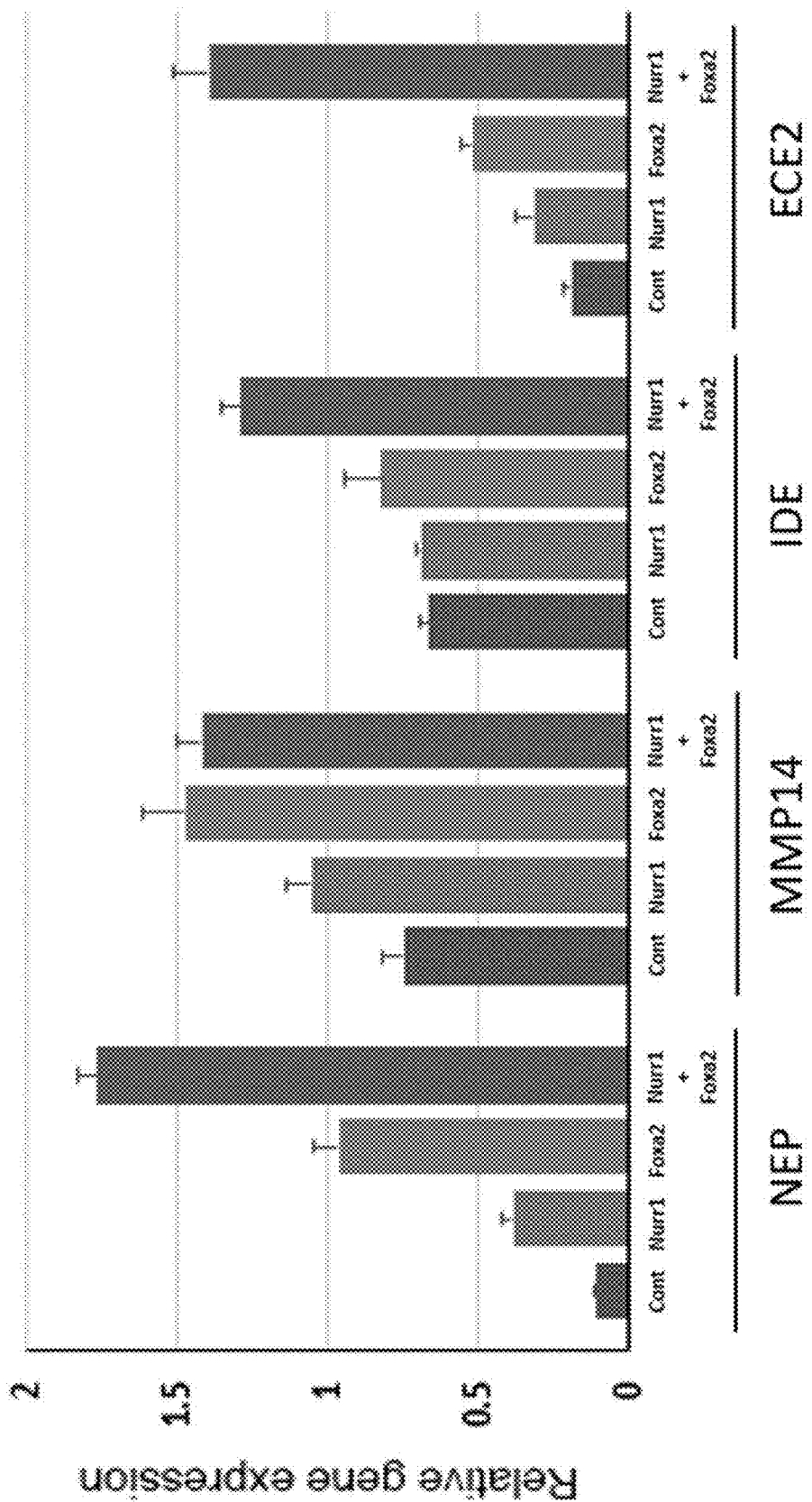
FIG. 11b shows gene expression levels of amyloid β disaggregation enzymes (e.g., NEP, MMP14, IDE, and ECE2) in control glia, glia expressing Nurr1 solely, glia expressing Foxa2 solely, and glia expressing both Nurr1 and Foxa2 after co-expression of Nurr1+Foxa2 genes in murine primary astrocytes, as analyzed by real-time PCR.

FIG. 11a shows ratios of gene expression levels of the enzymes in Nurr1+Foxa2-expressed glia to those in control glia as expressed in RNA-seq data. FIG. 11b shows gene expression levels of amyloid β disaggregation enzymes (e.g., NEP, MMP14, IDE, and ECE2) in control glia, glia expressing Nurr1 solely, glia expressing Foxa2 solely, and glia expressing both Nurr1 and Foxa2, as expressed in real-time PCR data.

Compared to glia expressing Nurr1 or Foxa2 solely, glia expressing both Nurr1 and Foxa2 were found to express greater levels of NEP, MMP14, IDE, and ECE2, which are enzymes involved in the disaggregation of amyloid β aggregates, indicating that co-expression of Nurr1 and Foxa2 genes has a synergistic effect of inhibiting amyloid β aggregation, compared to the expression of the genes individually.

Figure 11C:
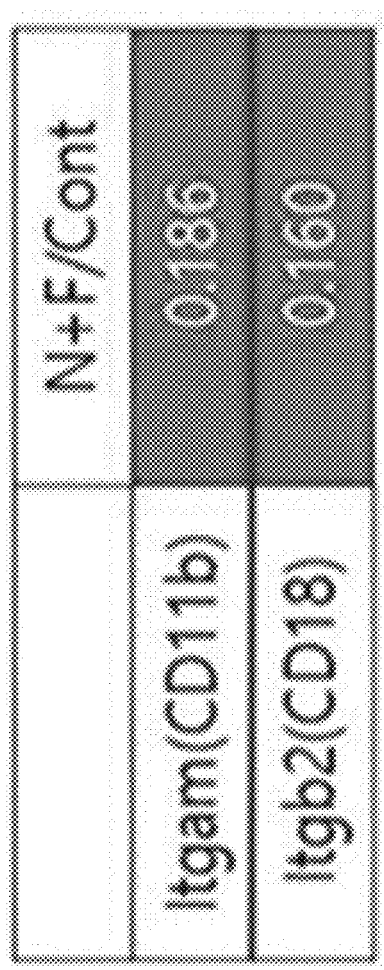
FIG. 11c shows ratios of gene expression level of CD11b and CD18 between Nurr1+Foxa2-expressed glia and control glia after co-expression of Nurr1+Foxa2 genes in murine primary astrocytes, as measured by RNA-Seq analysis for enzymes associated with the disaggregation of amyloid β.

In Nurr1+Foxa2-expressed glia, complement receptor β (CR3, heterodimer of CD11b/CD18) was observed to decrease in expression level (FIG. 11c). FIG. 11c shows ratios of gene expression levels of CD11b and CD18 in Nurr1+Foxa2-expressed glia to those in control glia. CR3 is known to inhibit the production of the aforementioned enzymes involved in amyloid β disaggregation (Czirr, E., et al. (2017). "Microglial complement receptor 3 regulates brain Abeta levels through secreted proteolytic activity." J Exp Med 214(4): 1081-1092). Accordingly, it is considered that the co-expression of Nurr1+Foxa2 genes downregulates CR3 expression, thereby increasing the expression of various enzymes promoting amyloid β disaggregation.

(7) Quantitation of Amyloid β Monomer by Thioflavin T Assay

Figure 12A:
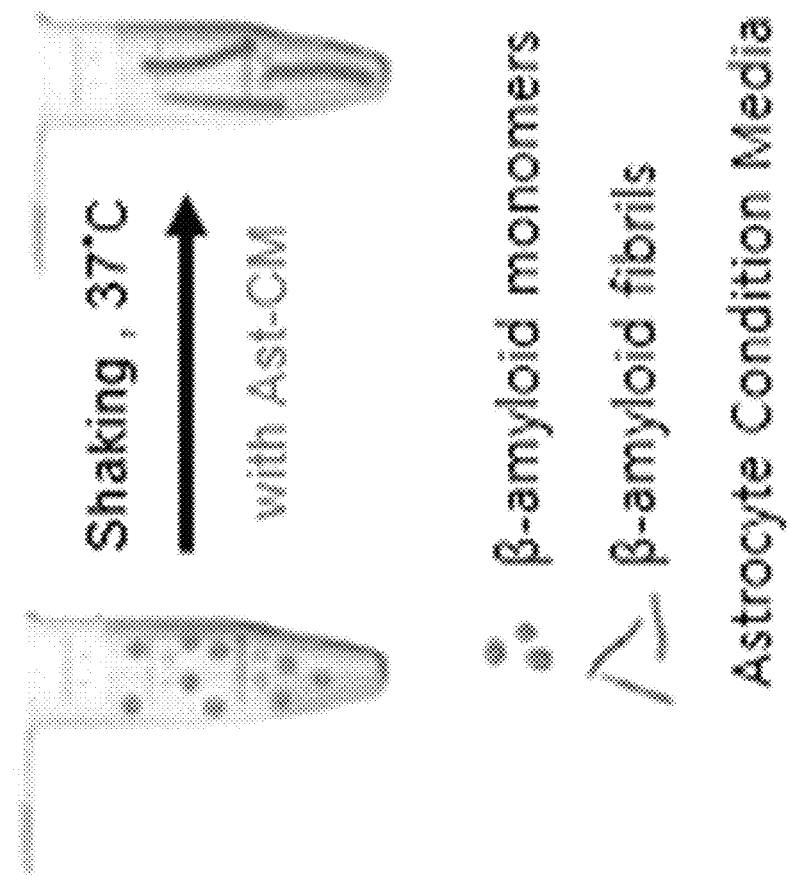
FIG. 12a illustrates an aggregation assay procedure for measuring amyloid β monomer (Aβ monomer) levels through thioflavin T (ThT) assay.

Amyloid β monomers (Aβ monomers) were quantitated by a thioflavin T assay (ThT assay). FIG. 12a illustrates an assay procedure for amyloid β aggregation. After a sample was centrifuged at 1000 rpm for 10 min at 37° C., the pellet thus obtained and CM were mixed with amyloid β monomers to induce fibrillization by which the monomers were allowed to aggregate into amyloid β fibrils (Aβ fibrils). Thereafter, a ThT assay solution was added (that is, a thioflavin T assay was conducted) so that ThT was attached to the amyloid β fibrils which can be quantitated based on the fluorescence of the attached ThT.

In this regard, 50 μl of a medium where Nurr1+Foxa2-expressed glia had been cultured (Nurr1+Foxa2), 50 μl of a medium where Nurr1-expressed glia had been cultured (Nurr1), 50 μl of a medium where control glia had been cultured (Cont), and 50 μl of a medium itself (Media) were each treated by the method above, and then mixed with 200 μl of a ThT assay solution. Here, the ThT assay solution was 25 μM ThT (cat. no. T3516, Sigma-Aldrich) in 10 mM glycine buffer (pH 9.0). Thereafter, amyloid β aggregation was quantitated on the basis of ThT fluorescence (excited at 440 nm) measured by fluorospectrometry at 482 nm.

Figure 12B:
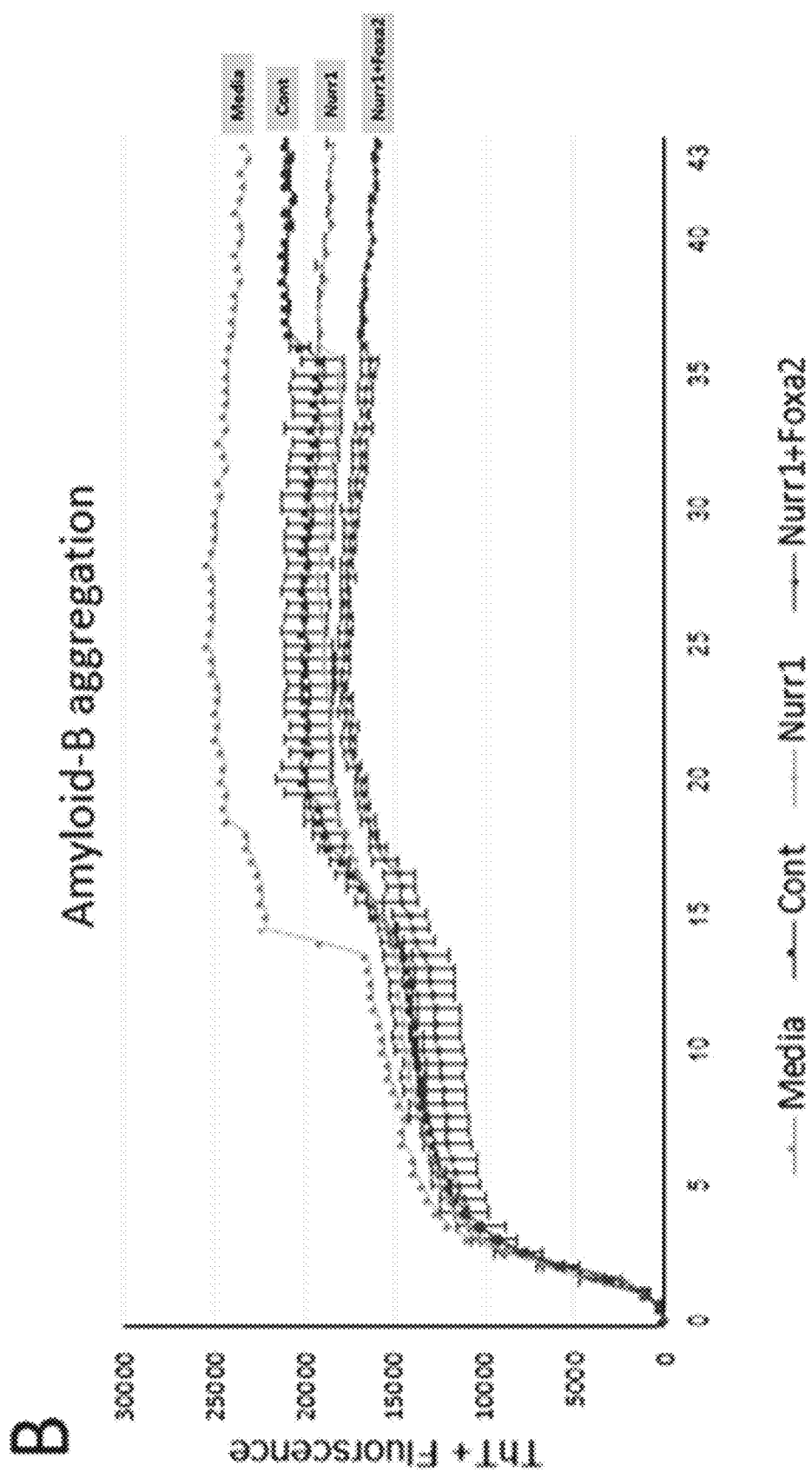
FIG. 12b is a plot of amyloid β monomer (Aβ monomer) levels after experiments for amyloid β aggregation, illustrating a synergistic effect of the group co-expressing Nurr1 and Foxa2, as measured by thioflavin T (ThT) assay.
Figure 12C:
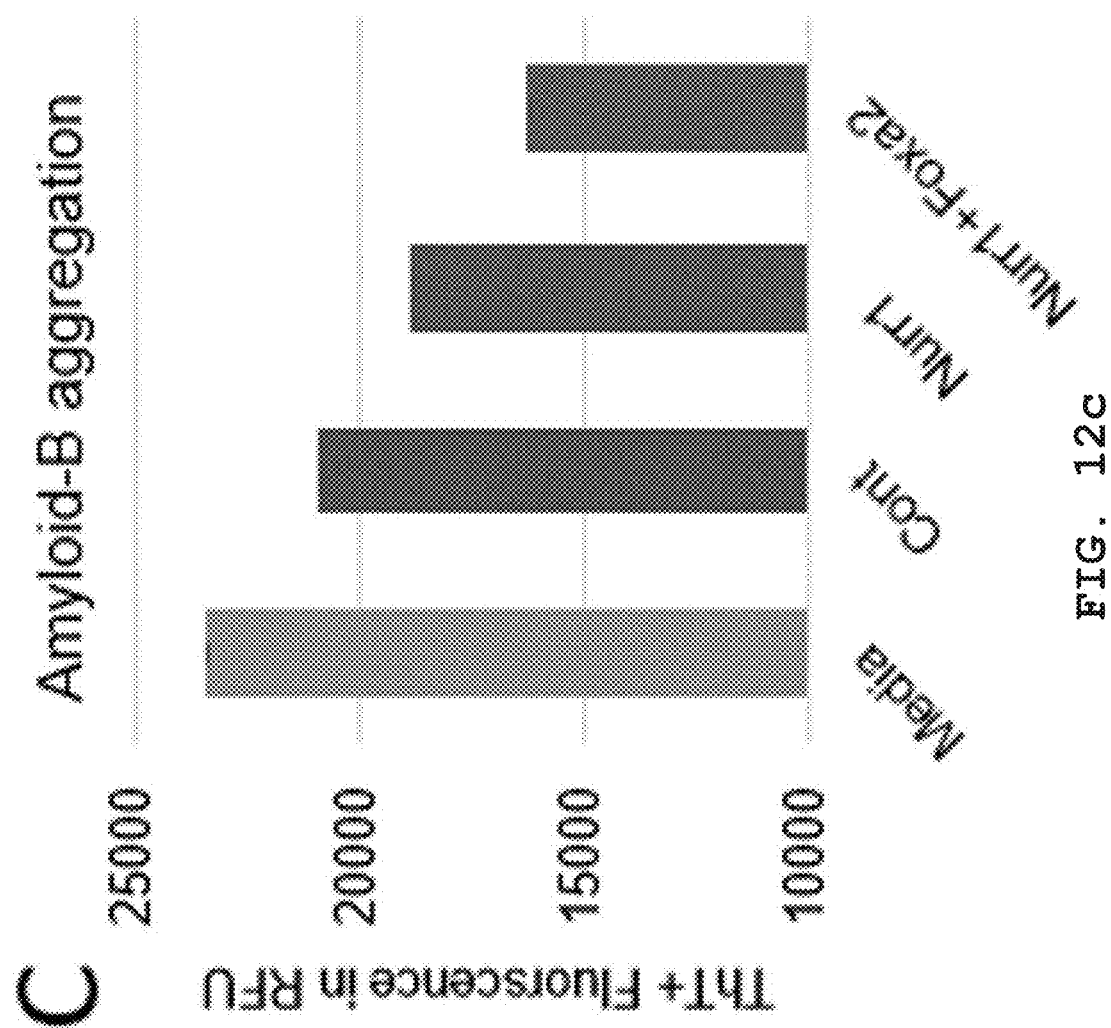
FIG. 12c is a bar graph of amyloid β monomer (Aβ monomer) levels after experiments for amyloid β aggregation, illustrating a synergistic effect of the group co-expressing Nurr1 and Foxa2, as measured by thioflavin T (ThT) assay.

An in-vitro amyloid β aggregation assay exhibited decreased aggregation of amyloid β in the culture medium sample treated with Nurr1+Foxa2-expressed glia (Nurr1+Foxa2), compared to the other samples (Nurr1, Cont, and Media) (FIGS. 12b and 12c).

The aggregation of amyloid β in the sample treated with a culture of Nurr1+Foxa2-expressed glia was significantly lower than those in the samples treated with the other cultures.

In addition, a culture of Nurr1+Foxa2-expressed glia has a higher effect of inhibiting amyloid β aggregation, compared to a culture of the control glia. In light of the effect of the glia expressing Nurr1 solely, the co-expression of Nurr1+Foxa2 was found to have a synergistic inhibitory effect on amyloid β aggregation.

Data obtained from the experiment indicate that a sample treated with a culture of Nurr1+Foxa2-expressed glia has an improved effect of inhibiting amyloid β aggregation, compared to a sample treated with a culture of control glia or glia expressing Nurr1 solely.

(8) Effect of Nurr1+Foxa2 Co-Expression on Expression of C3 and C1q

Complement components C3 and C1q are known to cause synapse loss and cognitive deficit in Alzheimer's disease (Hong, S., et al. (2016). "Complement and microglia mediate early synapse loss in Alzheimer mouse models." Science 352(6286): 712-716) (Shi, Q., et al. (2017). "Complement C3 deficiency protects against neurodegeneration in aged plaque-rich APP/PS1 mice." Sci Transl Med 9 (392)). In order to examine the therapeutic effect of glial co-expression of Nurr1+Foxa2 on Alzheimer's disease, Nurr1+Foxa2 was co-expressed specifically in hippocampal and intracerebroventricular glia of 3xFAD mice at 15 and 18 months of age, which had been induced to undergo Alzheimer's disease by mutagenesis on the three genes APP, PS1, and tau. Two months later, the hippocampus regions were triturated before RT-PCR.

Figure 13:
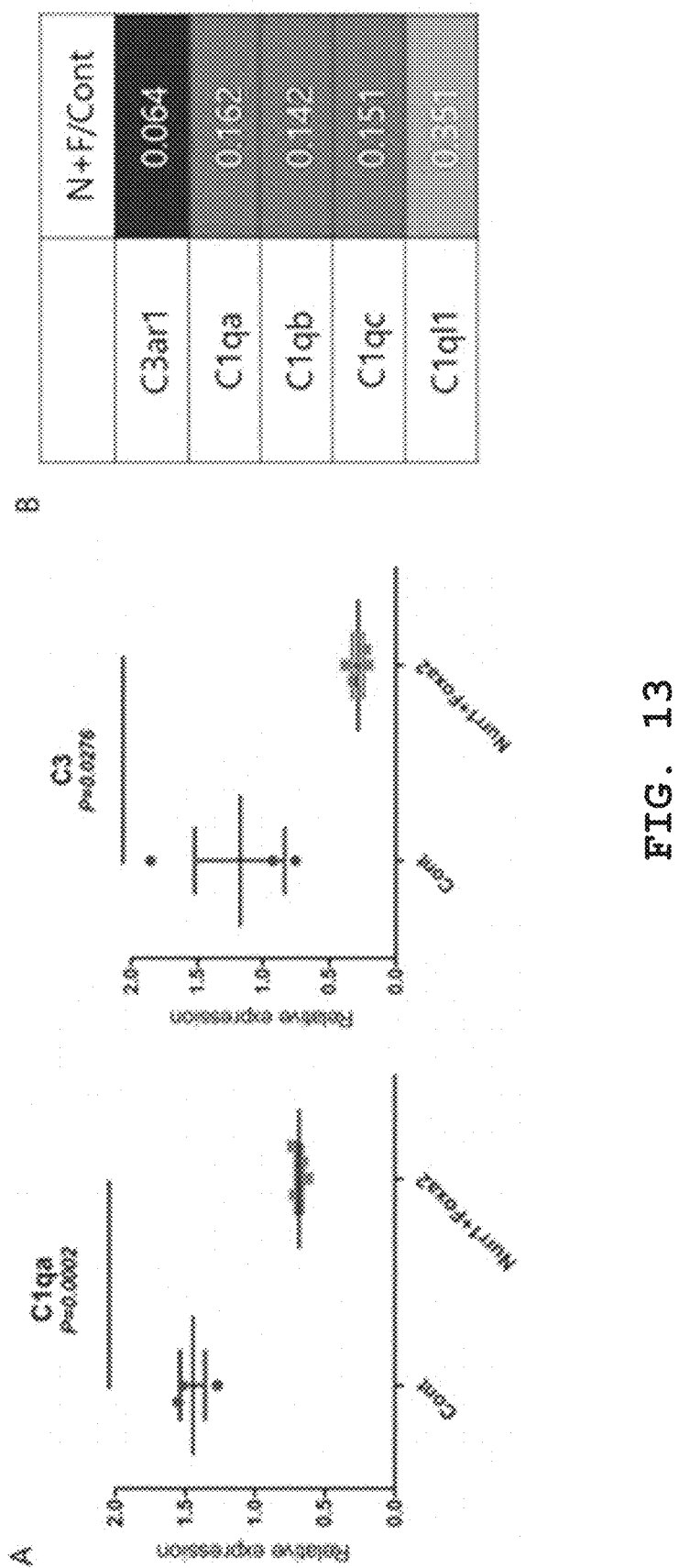
FIG. 13 shows levels of C1qa and C3 in glia after co-expression of Nurr1+Foxa2 genes therein, as analyzed by RT-PCR.

RT-PCR data thus obtained exhibited a significant reduction of C1qa and C3 mRNA levels in Nurr1+Foxa2-AAV9-introduced Alzheimer's disease model mice, compared to control-AAV9-introduced mice, which was consistent with RNA-Seq data. These results indicate that co-expression of Nurr1+Foxa2 prevents synapse loss and cognitive deficit in Alzheimer's disease (FIG. 13).

(9) Effect of Nurr1+Foxa2 Co-Expression on Expression of CCL3 and CCL4 Genes

The brain with Alzheimer's disease secretes the chemokines CCL3 and CCL4, which in turn induce an increase in the population of peripheral immune cells such as neutrophils, monocytes, and macrophages. The CCL3- and CCL4-mediated increase in the population of peripheral immune cells is known as one of main pathological symptoms of Alzheimer's disease (Kang, S. S., et al. (2018). "Microglial translational profiling reveals a convergent APOE pathway from aging, amyloid, and tau." J Exp Med 215(9): 2235-2245).

Figure 14:
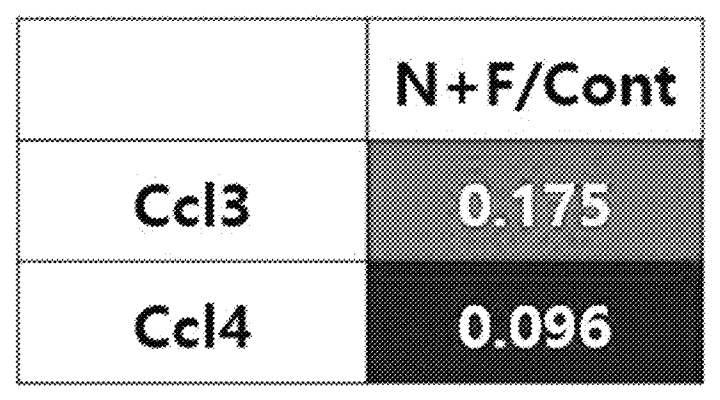

In order to examine the therapeutic effect of glial co-expression of Nurr1+Foxa2 on Alzheimer's disease, Nurr1+Foxa2 was co-expressed specifically in hippocampal and intracerebroventricular glia of 3xFAD mice at 15 and 18 months of age, which had been induced to undergo Alzheimer's disease by mutagenesis on the three genes APP, PS1, and tau. Two months later, the hippocampus regions were triturated before RNA-Seq. RNA-Seq data thus obtained exhibited a significant reduction of CCL3 and CCL4 gene expression levels in a culture of Nurr1+Foxa2-expressed glia, compared to a culture of control glia (FIG. 14). The result indicates that co-expression of Nurr1+Foxa2 is effective for palliating the pathological symptom of Alzheimer's disease.

(10) Downregulation of Inflammatory Factor and Inflammasome Level and Upregulation of Neurotrophic Factor Level by Synergistic Reaction of Nurr1 and Foxa2 in Amyloid β Alzheimer's Disease Model An important mechanism involved in the amyloid β deposition in Alzheimer's disease is accounted for by inflammasomes. An inflammasome is a multiprotein oligomer composed of ASC, NLRP3, and Caspase1 and activates an inflammatory response.

The deposition of amyloid β in the brain induces the activation of the innate immune system and the formation of inflammasome-dependent ASC specks in microglia. The ASC specks released from microglia seed amyloid β oligomers and aggregates. That is, the activation of inflammasomes is responsible for the seeding and spreading of amyloid β pathology. (Venegas, C., et al. (2017). Microglia-derived ASC specks cross-seed amyloid-beta in Alzheimer's disease. Nature, 552(7685), 355-361. doi: 10.1038/nature25158).

The inflammation mediated by NLRP3/Caspase1, which is an inflammasome component, plays a critical role in behavioral and cognitive dysfunction. For example, the amyloid β-induced activation of NLRP3 inflammasomes causes a chronic inflammatory tissue response, resulting in promoting the progression of Alzheimer's disease. Thus, blocking the activation of NLRP3 inflammasomes or inhibiting the activity of inflammasome-derived cytokines can be a therapeutic strategy to prevent the progression of Alzheimer's disease (Heneka, M. T., et al. (2013). NLRP3 is activated in Alzheimer's disease and contributes to pathology in APP/PS1 mice. Nature, 493(7434), 674-678. doi: 10.1038/nature11729).

In order to examine the therapeutic effect of glial Nurr1+Foxa2 coexpression on Alzheimer's disease, 10-week-old ICR mice were injected with an amyloid β aggregate at the intracerebroventricle thereof while Nurr1+Foxa2 genes were introduced into the hippocampus with the aid of AAV-9 (CMV or GFAP promoter for gene expression). The hippocampus was homogenized before RT-PCR.

Figure 15:
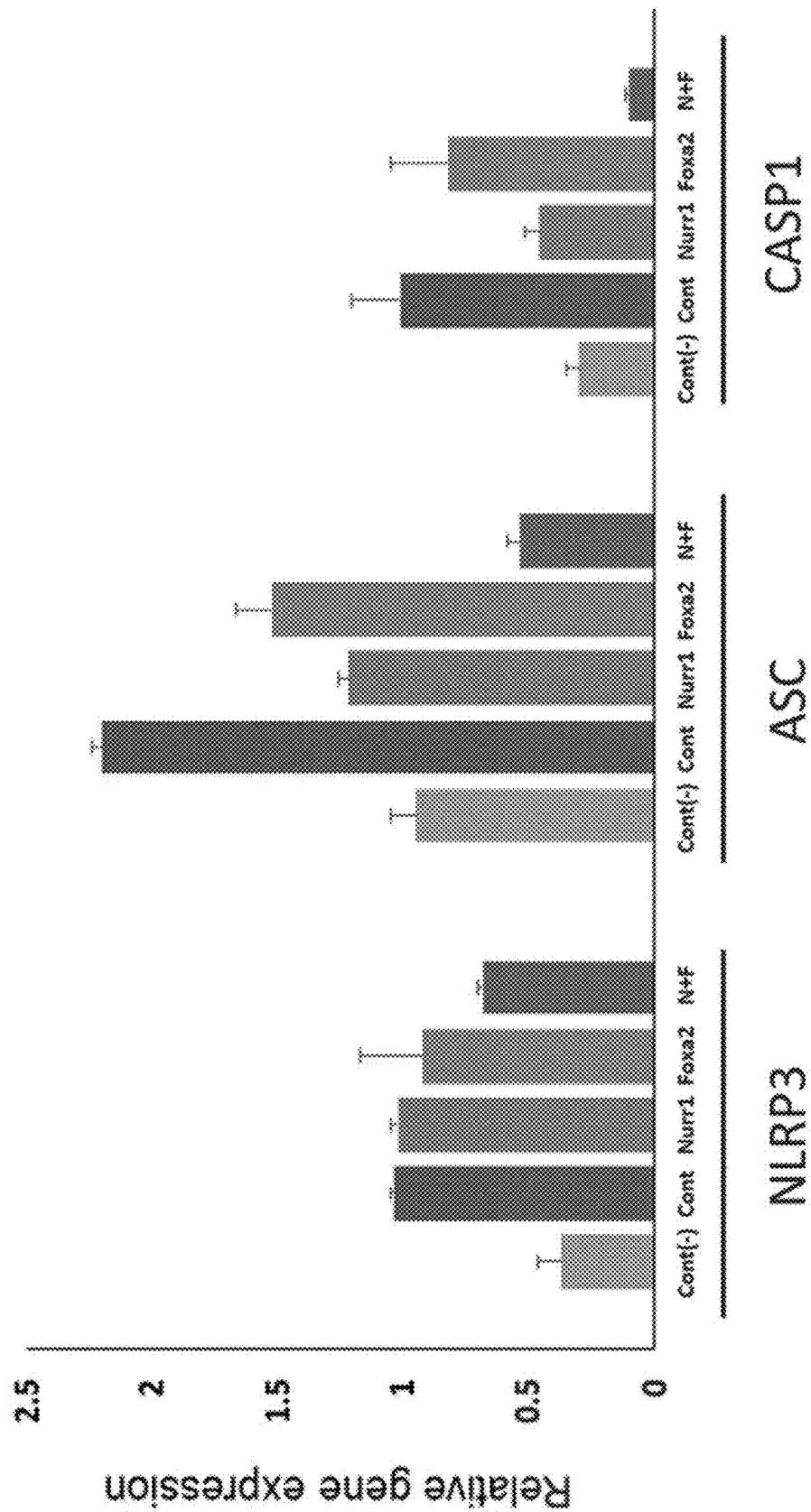
FIG. 15 shows levels of hippocampal inflammasome proteins (NLRP3, ASC, and CASP1) in amyloid β Alzheimer's disease model mice after transduction of Nurr1+Foxa2 genes into the hippocampus, as analyzed by RT-PCR.

FIG. 15 shows RT-PCR results in the hippocampus of amyloid β Alzheimer's disease model mice after introduction of Nurr1+Foxa2 genes into the hippocampus with the aid of AAV-9 (CMV or GFAP promoter). It was observed in the amyloid β Alzheimer's disease model that inflammation and inflammasome levels were reduced in a synergistic manner in the hippocampal region treated with Nurr1 and Foxa2 in combination, compared to the hippocampal region treated with Nurr1 or Foxa2 alone.

As stated above, inflammasome proteins that correlate with the onset of Alzheimer's disease were analyzed by electrophoresis to examine whether the co-expression of Nurr1 and Foxa2 in the hippocampus of Alzheimer's disease model mice induces a reduction in inflammasome.

Figure 16:
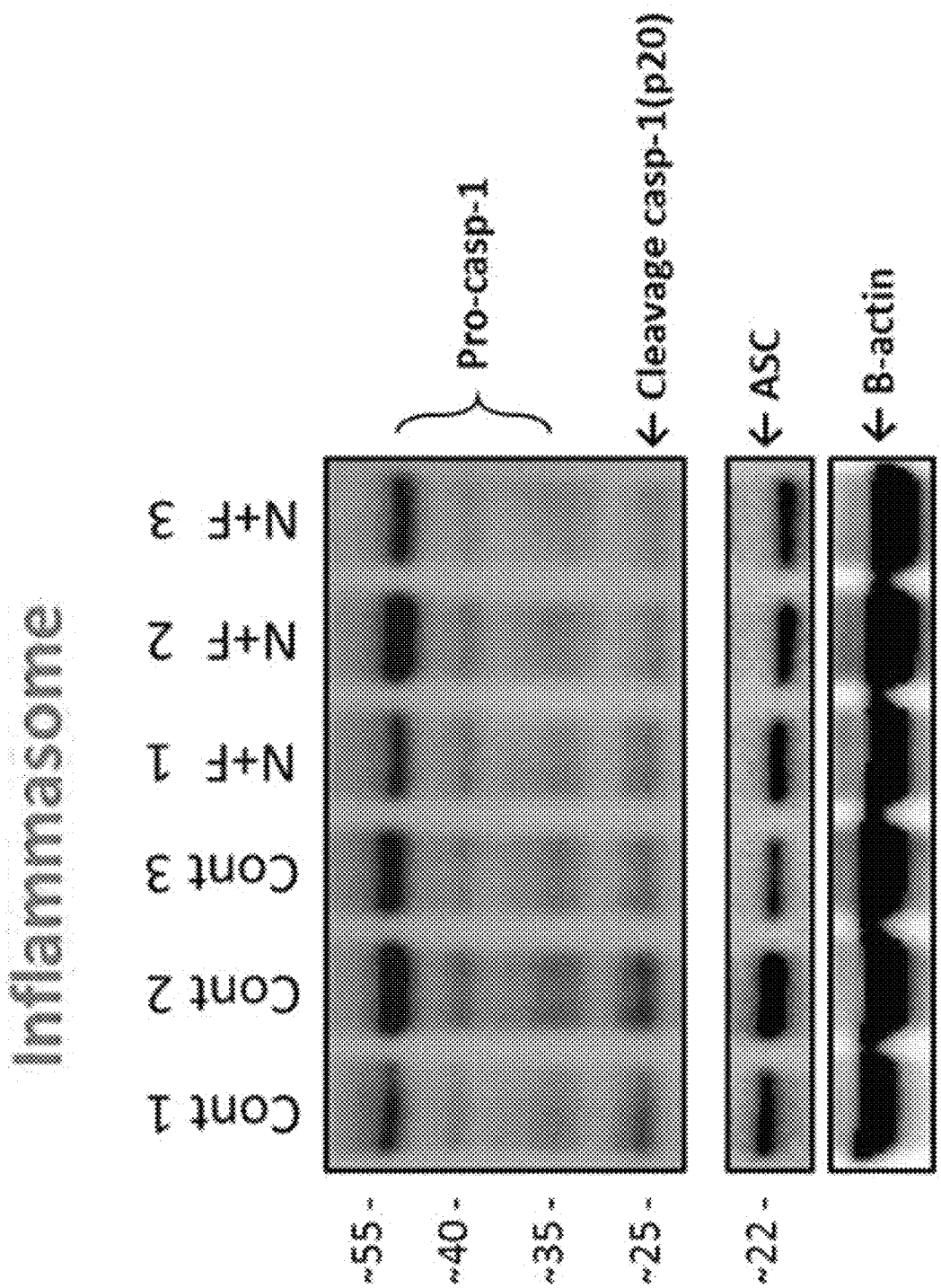
FIG. 16 shows protein levels of hippocampal inflammasome markers two months after specific transduction of Nurr1+Foxa2 genes into the murine hippocampus and intracerebroventricle, as measured by western blotting.

FIG. 16 shows protein levels of inflammasome markers in the hippocampus two months after specific transduction of Nurr1+Foxa2 genes into hippocampal and intracerebroventricular glial cells in 3xFAD mice at 15 months of age, as analyzed by Western blotting. As can be seen, levels of the inflammasome markers pro-caspase1 and cleavage caspase1 were reduced, and a general reduced level was also detected in the ASC protein.

Figure 17:
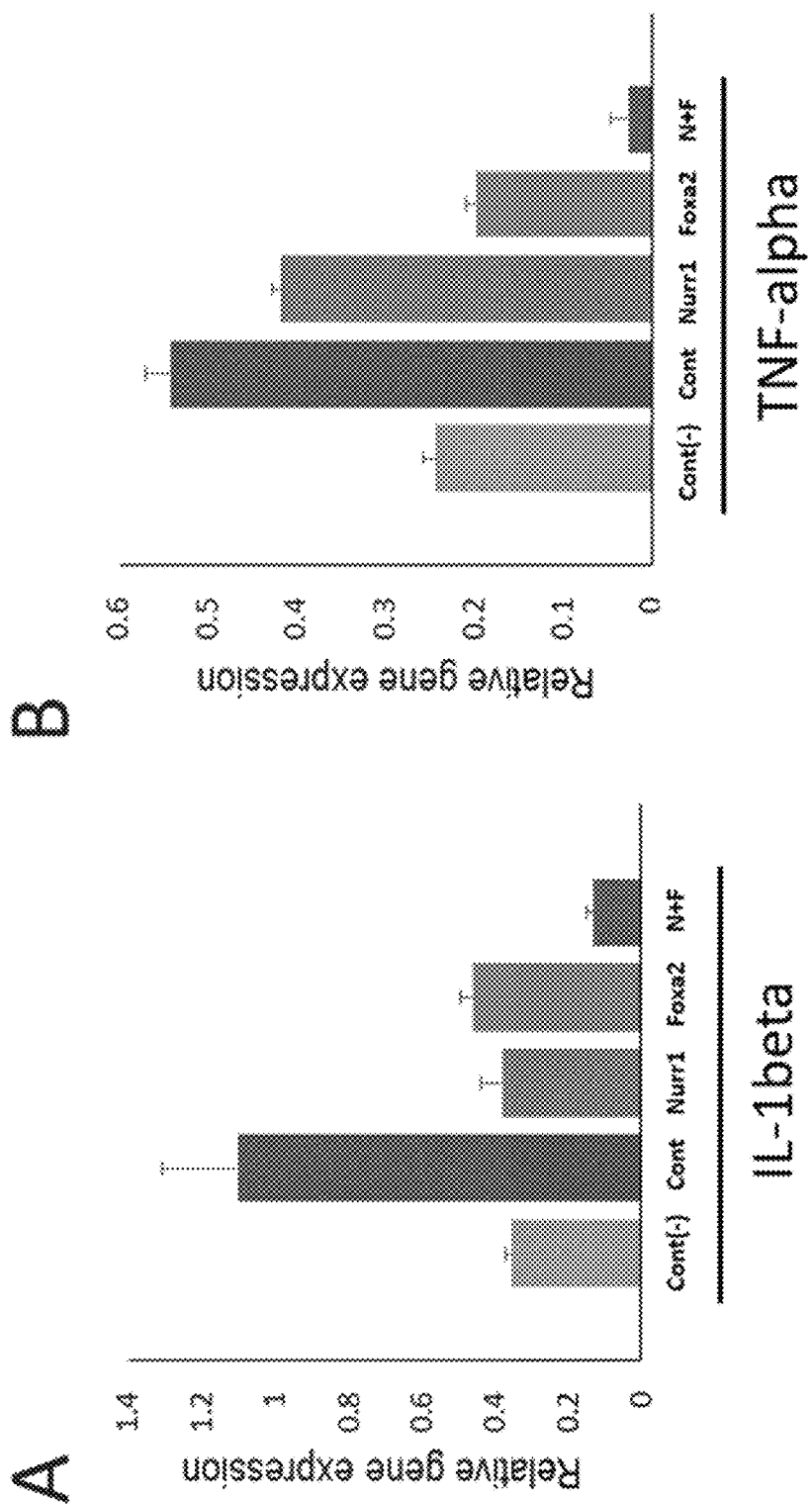
FIG. 17 shows levels of hippocampal inflammatory cytokines (IL-1β, TNF-α) in amyloid β Alzheimer's disease model mice after transduction of Nurr1+Foxa2 genes into the hippocampus, as measured by RT-PCR.

FIG. 17 shows mRNA levels of inflammatory cytokines (IL-1β and TNF-α) in the hippocampus after transduction of Nurr1+Foxa2 genes into the hippocampus of amyloid β Alzheimer's disease model mice, as analyzed by RT-PCR. As shown, the expression of Nurr1 and Foxa2 genes reduced transcriptional levels of inflammatory cytokines IL-1β and TNF-α. Particularly, co-expression of Nurr1 and Foxa2 genes resulted in a great reduction in the expression level of inflammatory cytokines.

Figure 18:
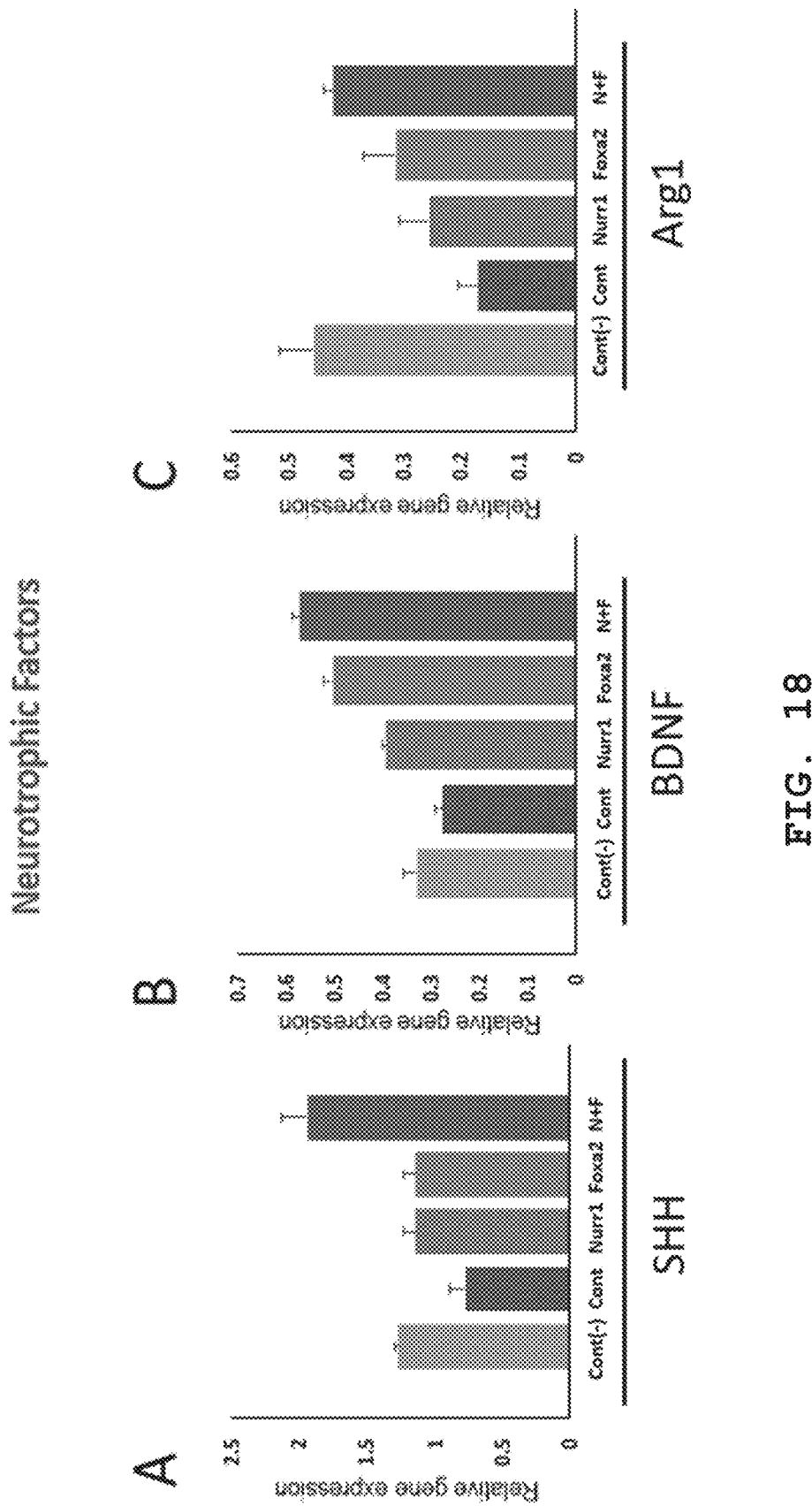
FIG. 18 shows levels of hippocampal neurotrophic factors (SHH, BDNF, Arg1) in amyloid β Alzheimer's disease model mice after transduction of Nurr1+Foxa2 genes into the hippocampus, as measured by RT-PCR.

FIG. 18 shows mRNA levels of neurotrophic factors (SHH, BDNF, and Arg1) in the hippocampus after transduction of Nurr1+Foxa2 genes into the hippocampus of amyloid β Alzheimer's disease model mice, as analyzed by RT-PCR. As shown, the expression of Nurr1 and Foxa2 genes increased transcriptional levels of the neurotrophic factors. Particularly, co-expression of Nurr1 and Foxa2 genes resulted in a synergistic increase in the levels of the neurotrophic factors.

Taken together, the data imply that co-expression of Nurr1 and Foxa2 has synergistic effects of reducing inflammation and inflammasome levels and increasing neurotrophic factor levels.

(11) Downregulation of Factors in NF-κB Signaling Pathway by Synergistic Reaction of Nurr1 and Foxa2 in Amyloid β Alzheimer's Disease Model NK (nuclear factor)-kB is a transcription factor involved in various biological activities and particularly plays a pivotal role in immunity and inflammatory reactions. NF-κB is a heterodimer consisting of p50 and p65 (RelA) proteins and binds mainly to DNA. In addition, NF-κB is known to act a critical role in the expression of pro-inflammatory genes. For this reason, intensive research into the therapy of chronic inflammation has been made to develop inhibitors against the pathway.

As described above, Nurr1 and Foxa2 were observed to act in synergy with each other to regulate inflammation. Accordingly, the following experiment was carried out to examine whether the regulation of inflammatory reactions is done through NF-κB.

Cerebral cortical astrocytes from mice on postnatal day 1 were primarily cultured and then allowed to express the genes with the aid of Lentivirus according to the four groups CMV promotor Control, Nurr1, Foxa2, and Nurr1+Foxa2. Thereafter, the cells were treated with amyloid aggregates before western blot analysis of NF-κB signaling factors.

Figure 19A:
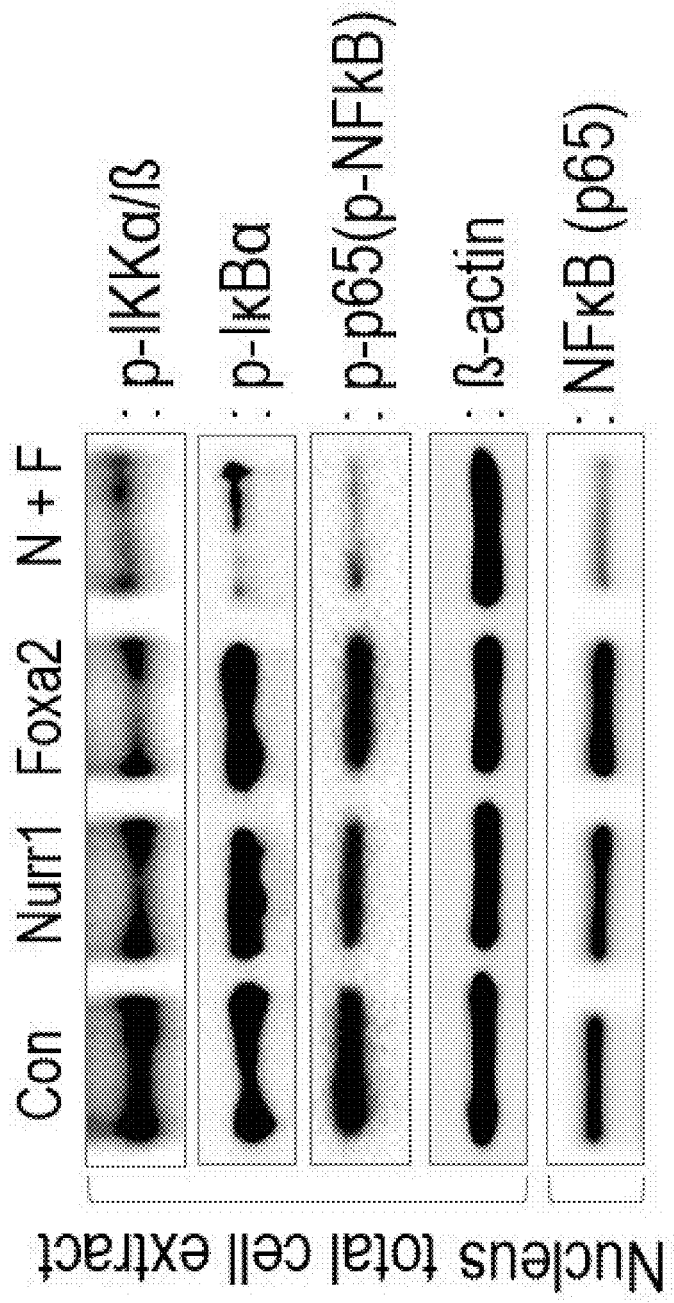
FIG. 19a shows expression levels of NF-κB signaling pathway factors in cerebral cortical astrocytes after application of a beta amyloid aggregating agent to the cells classified into the four groups CMV promotor control, Nurr1, Foxa2, and Nurr1+Foxa2 according to the genes expressed therein, as measured by western blotting.
Figure 19B:
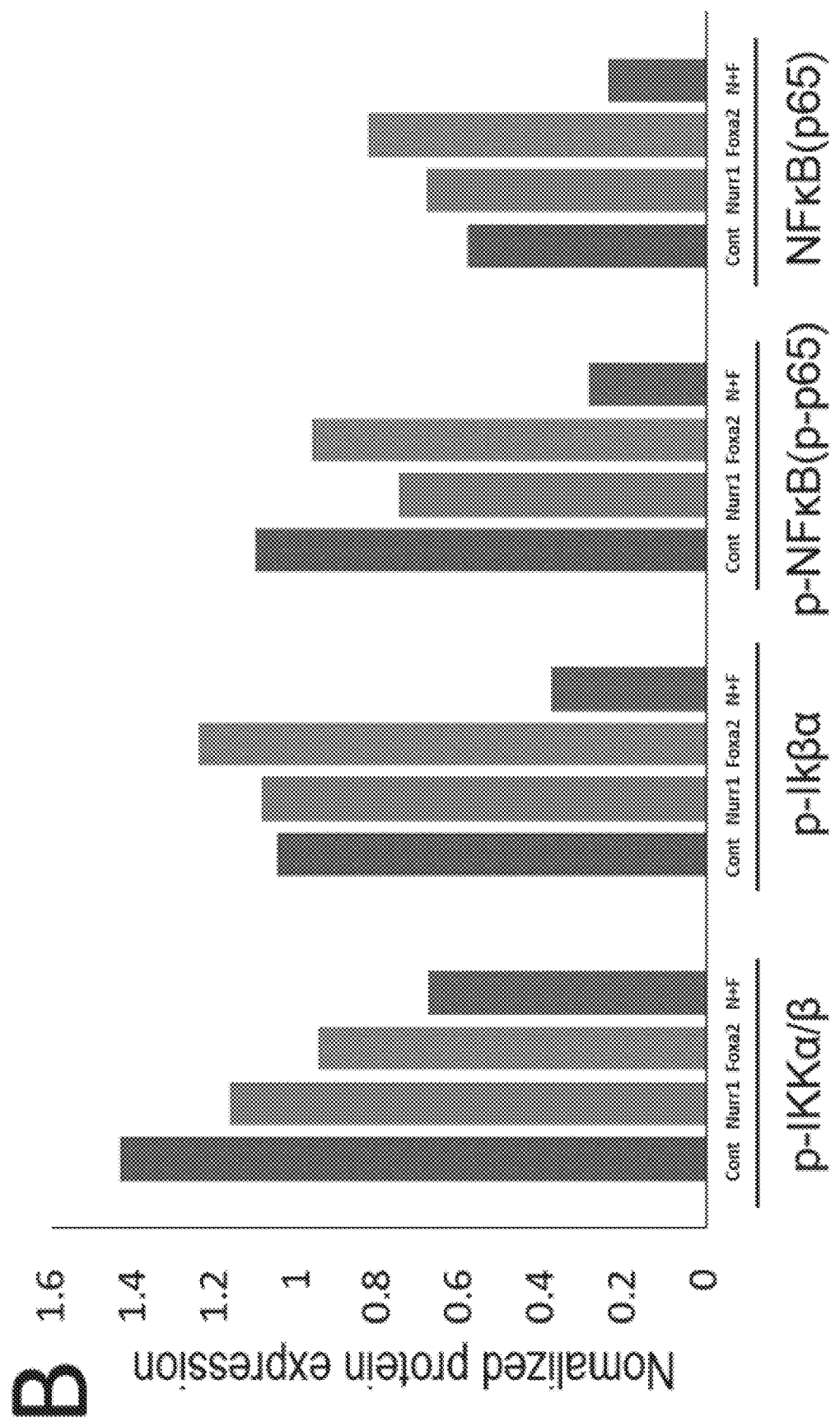
FIG. 19b shows expression levels of NF-κB signaling pathway factors in cerebral cortical astrocytes after application of a beta amyloid aggregating agent to the cells classified into the four groups CMV promotor control, Nurr1, Foxa2, and Nurr1+Foxa2 according to the genes expressed therein, as quantitatively measured by western blotting.

When Control, Nurr1, Foxa2, and Nurr1+Foxa2 were separately expressed in murine cerebral cortical astrocytes with the aid of Lentivirus, phosphorylated (activated) forms of IKKα/β, Ikβα, and NFκB, which are main factors in the NFκB signaling pathway, were observed to be present at reduced levels in the cytoplasm of the Nurr1+Foxa2 group while the protein level of NFκB in the nucleus was also decreased (FIGS. 19a and 19b). The reduction was proceeded to a higher degree in the Nurr1+Foxa2 group than the Nurr1 group or the Foxa2 group, implying that Nurr1 and foxa2 act in synergy with each other to regulate NFκB.

Hippocampal astrocytes from mice on postnatal day 1 were primarily cultured and treated with or without a beta amyloid aggregating agent. The beta amyloid aggregating agent-treated cells were classified into the three groups CMV promotor Control, Nurr1, and Nurr1+Foxa2. All of the astrocytes were allowed to express the corresponding genes with the aid of Lentivirus. Thereafter, factors involved in the NFκB signaling pathways were analyzed by western blotting.

Figure 19C:
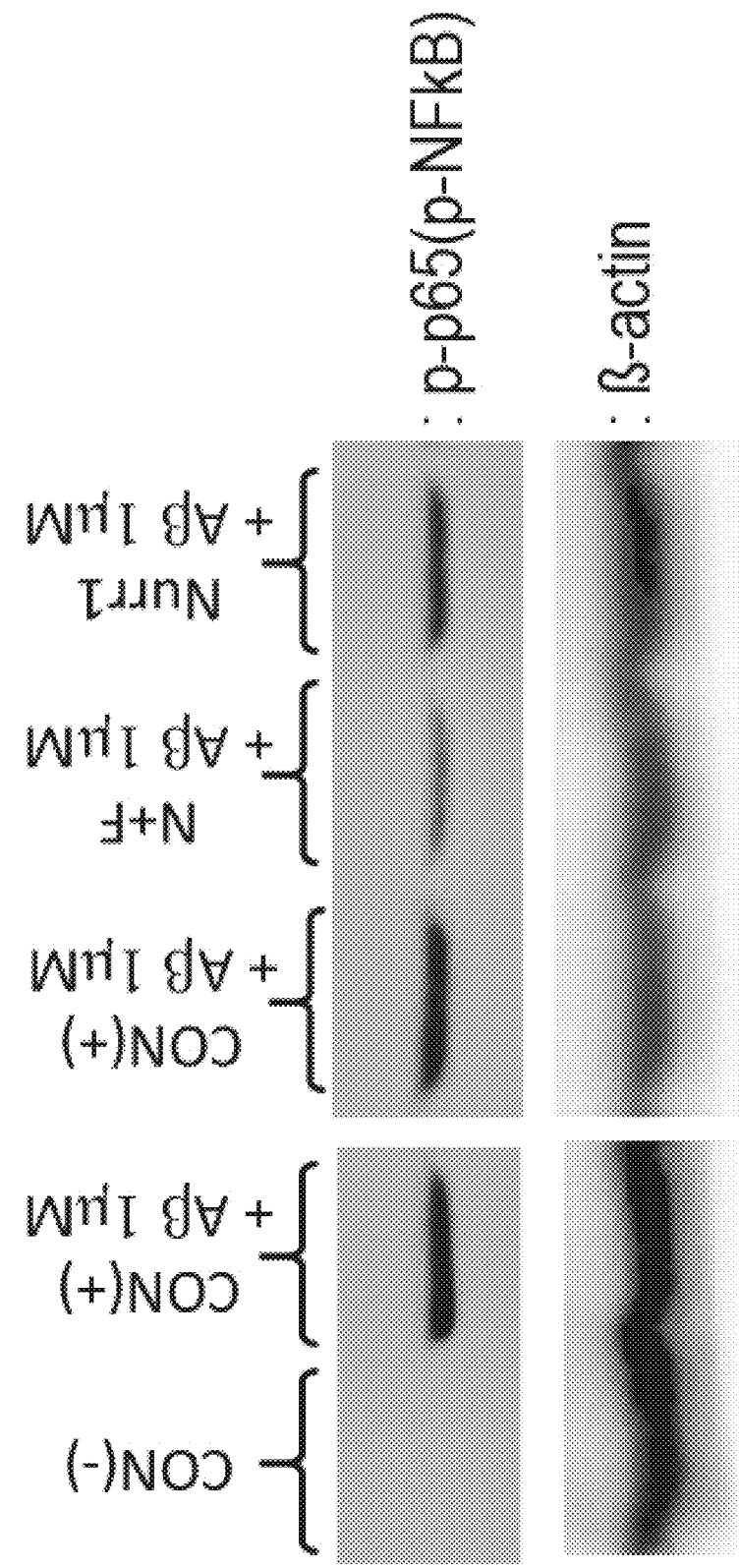
FIG. 19c shows expression levels of NF-κB signaling pathway factors in hippocampal astrocytes after treatment of the cells with or without a beta amyloid aggregating agent and classification of the beta amyloid aggregating agent-treated cells into the three groups CMV promotor control, Nurr1, and Nurr1+Foxa2 according to the genes expressed therein, as measured by western blotting.
Figure 19D:
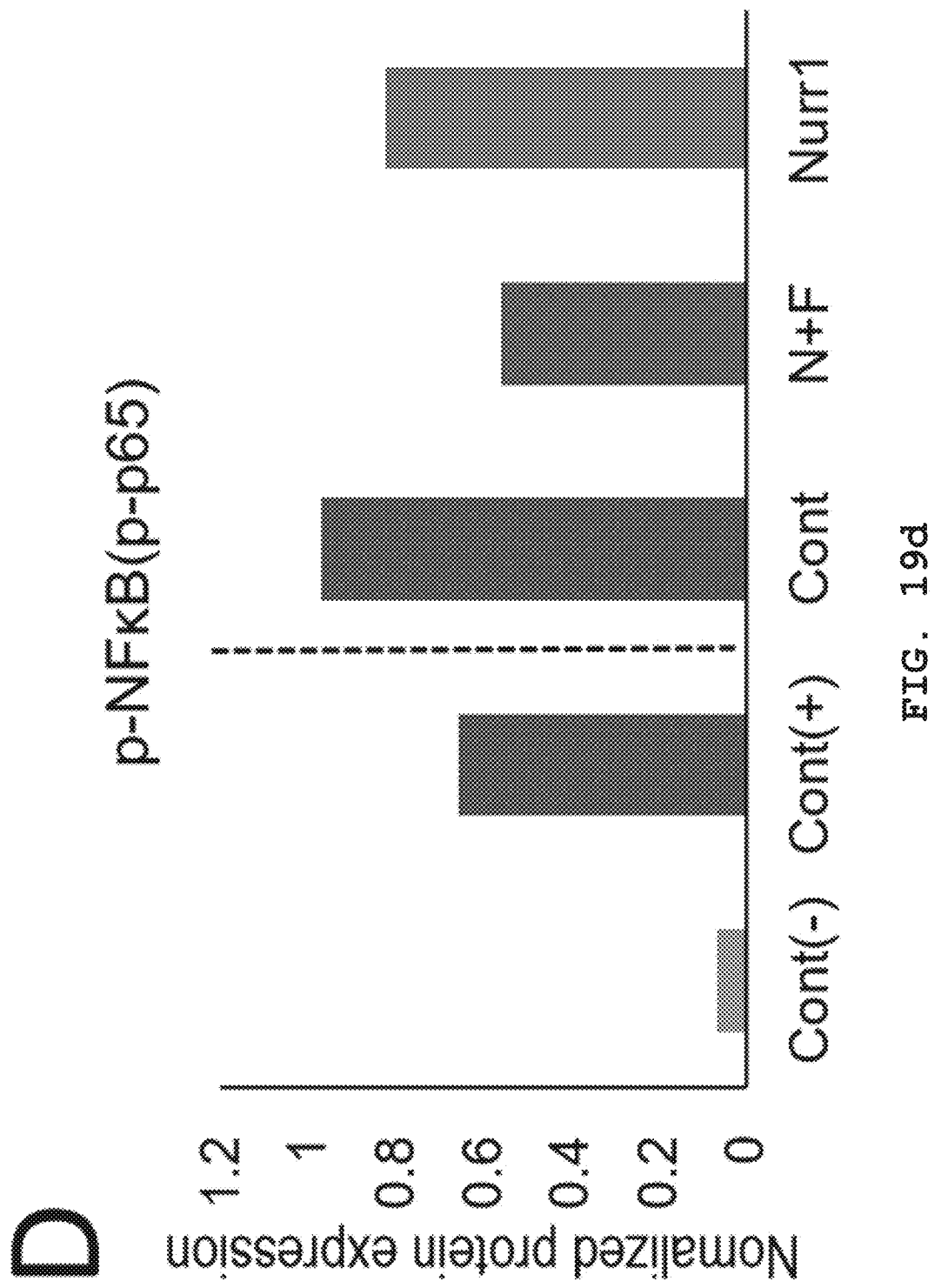
FIG. 19d shows expression levels of NF-κB signaling pathway factors in hippocampal astrocytes after treatment of the cells with or without a beta amyloid aggregating agent and classification of the beta amyloid aggregating agent-treated cells into the three groups CMV promotor control, Nurr1, and Nurr1+Foxa2 according to the genes overexpressed therein, as quantitatively measured by western blotting.

When Control, Nurr1, and Nurr1+Foxa2 were separately expressed in murine hippocampal astrocytes with the aid of Lentivirus, the phosphorylated (activated) form of NFκB, which is a main factor in the NFκB signaling pathway, was observed to be present at a reduced levels primarily in the cytoplasm of the Nurr1+Foxa2 group (FIGS. 19c and 19d). The reduction was proceeded to a higher degree in the Nurr1+Foxa2 group than the Nurr1 group, implying that Nurr1 and Foxa2 act in synergy with each other to regulate NFκB.

(12) Synergistic Protective Activity of Nurr1 and Foxa2 Against Synapse Loss in Amyloid Beta Alzheimer's Disease Model In Alzheimer's disease, synapse loss correlates with cognitive deficit. Involvement of microglia and complement in Alzheimer's disease is attributed to neuroinflammation, resulting in synapse loss (Hong, S., Beja-Glasser, V. F., Nfonoyim, B. M., Frouin, A., Li, S., Ramakrishnan, S., Merry K. M., Shi Q., Rosenthal A., Barres B. A., Lemere C. A., Selkoe D. J., Stevens, B. (2016). Complement and microglia mediate early synapse loss in Alzheimer mouse models. Science, 352(6286), 712-716. doi:10.1126/science.aad8373).

In this regard, the protective activity of Nurr1 and Foxa2 against synapse loss in the hippocampus of Alzheimer's disease model mice was examined by electrophoresis for synaptogenic proteins expressed in mature synapses.

Examination was made of the therapeutic effect of glial Nurr1+Foxa2 co-expression on Alzheimer's disease. To this end, Nurr1+Foxa2 were expressed with the aid of AAV9 serotype virus specifically in hippocampal and intracerebroventricular glial cells from 3xFAD mice at 15 months of age, in which Alzheimer's disease had been induced by mutagenesis on the three genes APP, PS1, and tau. About two months later, the hippocampus was excised and subjected to electrophoresis for synaptogenic proteins and inflammasomes.

Two months after specific transduction of Nurr1+Foxa2 genes into hippocampal and intracerebroventricular glial cells of 3xFAD mice at 15 months of age, the hippocampus was excised and subjected to western blot analysis for synaptogenic proteins and inflammasomes.

Figure 20A:
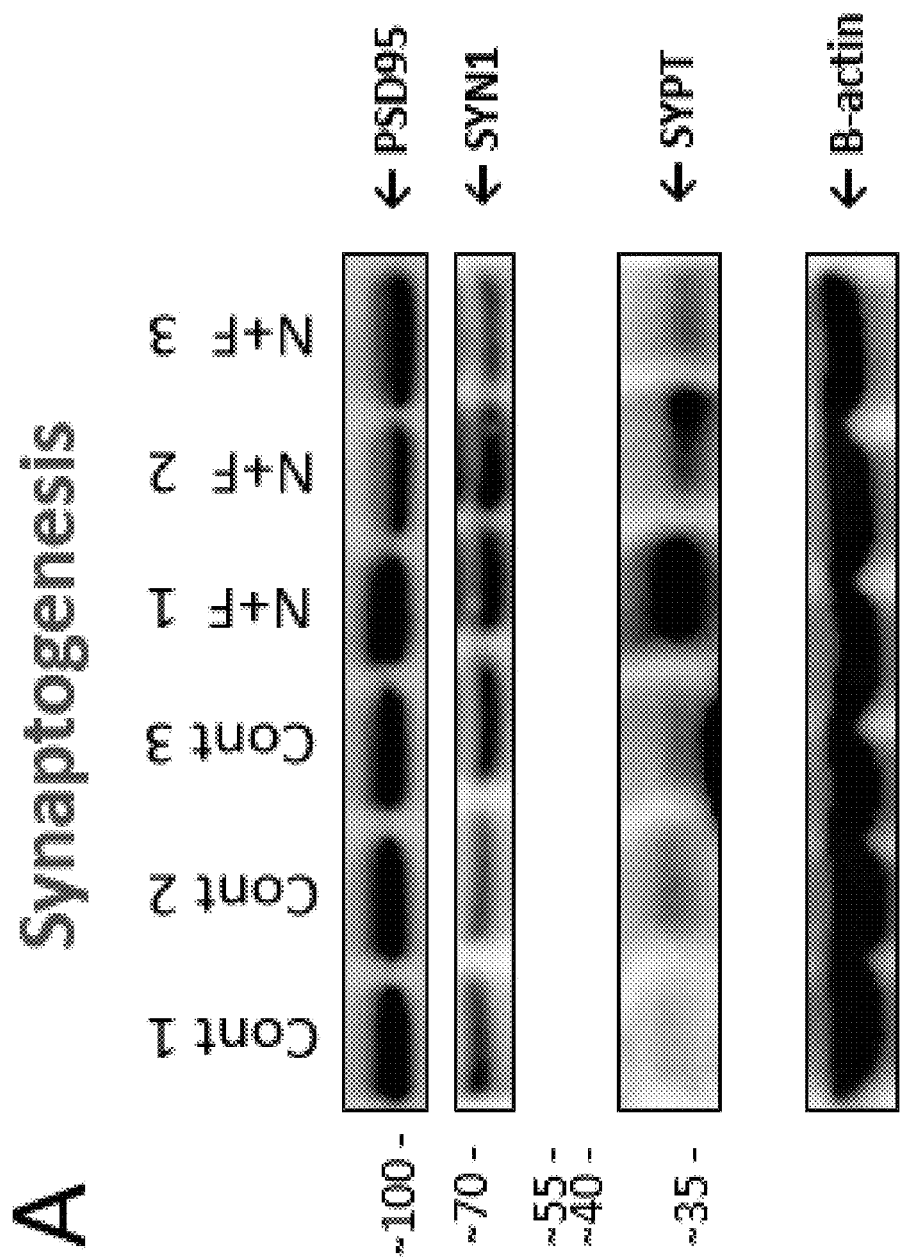
FIG. 20a shows protein levels of synaptogenic markers in the murine hippocampus two months after specific transduction of Nurr1+Foxa2 genes into hippocampal and intracerebroventricular glial cells of the mice, as analyzed by western blotting.
Figure 20B:
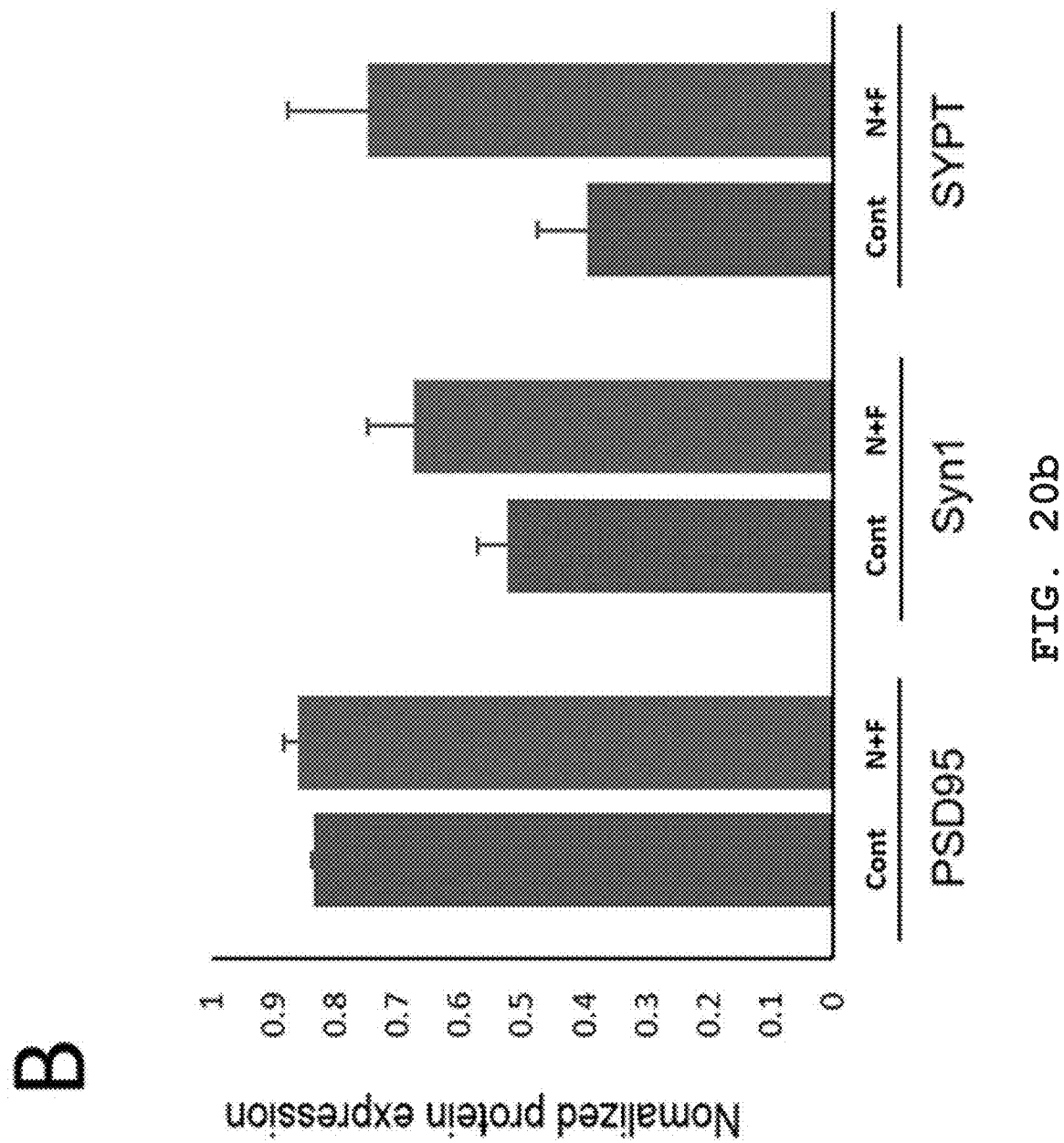
FIG. 20b shows protein levels of synaptogenic markers in the murine hippocampus two months after specific transduction of Nurr1+Foxa2 genes into hippocampal and intracerebroventricular glial cells of the mice, as quantitatively analyzed by western blotting.

FIG. 20 shows protein levels of synaptogenic markers in the hippocampus of 15-month-old 3xFAD mice two months after specific transduction of Nurr1+Foxa2 genes into hippocampal and intracerebroventricular glial cells of the mice, as quantitatively analyzed by western blotting. As can be seen, increased levels of the synaptogenic proteins synapsin1 and synaptophsin were detected in the Nurr1+Foxa2-treated group, compared to the control.

(13) Preventive Effect of Nurr1+Foxa2 Transduction on Glial Cell Senescence

Glial cell senescence is known as one of representative symptoms of Alzheimer's disease (Bussian, T. J., et al. (2018). "Clearance of senescent glia prevents tau-dependent pathology and cognitive decline." Nature 562(7728): 578-582) (Chinta, S. J., et al. (2018). "Cellular Senescence Is Induced by the Environmental Neurotoxin Paraquat and Contributes to Neuropathology Linked to Parkinson's Disease." Cell Rep 22(4): 930-940) (Bhat, R., et al. (2012). Astrocyte senescence as a component of Alzheimer's disease. PLoS One, 7 (9), e45069. doi:10.1371/journal.pone.0045). There is a mechanism known to cause Alzheimer's disease, in which amyloid β triggers senescence and senescent astrocytes produce inflammatory cytokines including interleukin-6 (IL-6) (Bhat et al., 2012). An experiment was carried out to investigate the effect of co-expression of Nurr1+Foxa2 genes in cultured glia on glial cell senescence.

Figure 21A:
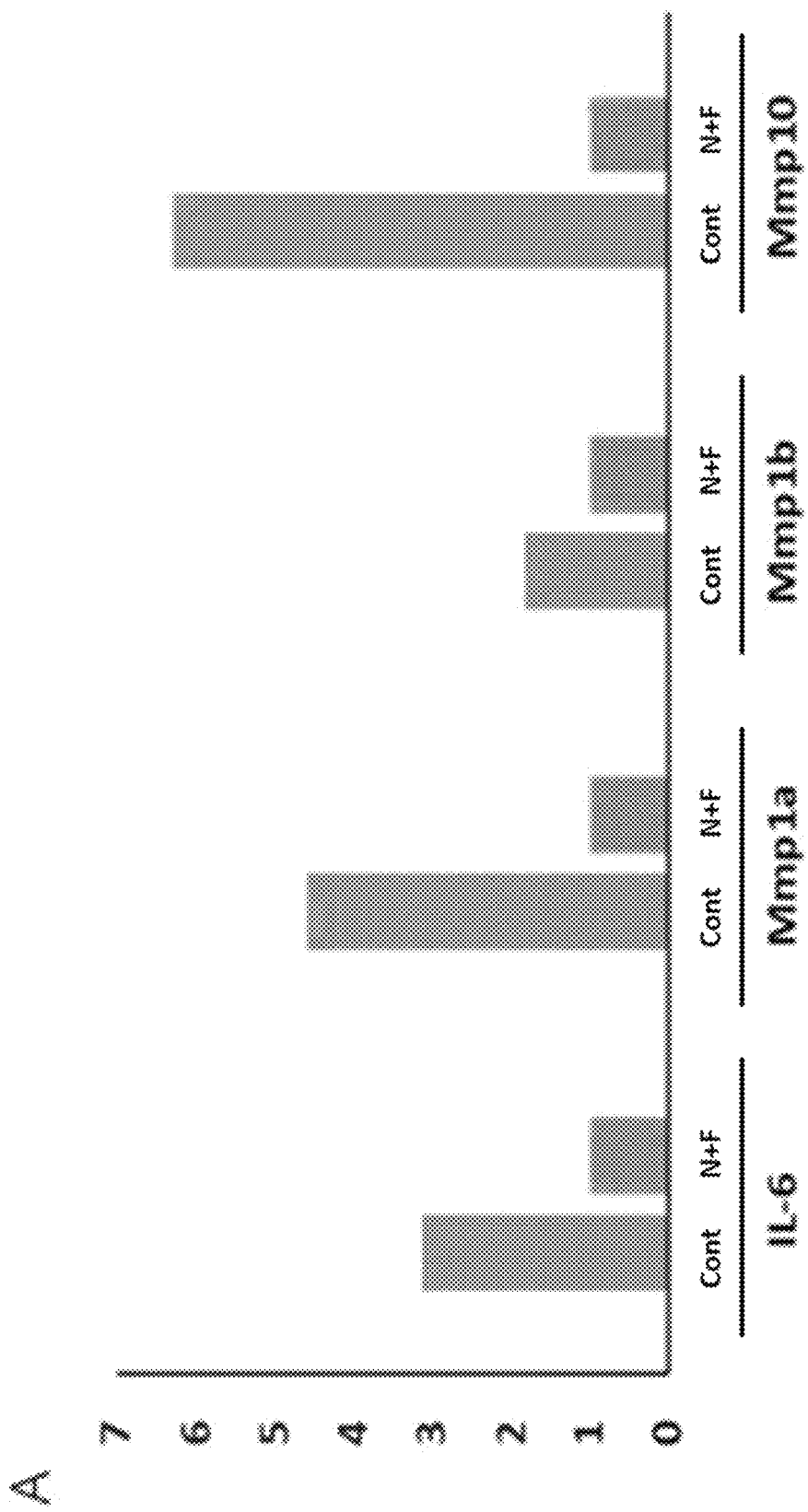
FIG. 21a shows RNA-Seq data for expression levels of the senescence-inducing genes IL6, MMP1a, MMP1b, and MMP10 in glia after co-expression of Nurr1+Foxa2 genes therein.

FIG. 21a shows real-time PCR data for expression levels of genes responsible for cellular senescence in the cultured glial cells into which virus carrying Nurr1+Foxa2 genes or control virus has been introduced. mRNA levels of the senescence-inducing factors IL6, MMP1, and MMP10 were reduced in the Nurr1+Foxa2-expressed glial cells, compared to the control glial cells, as analyzed by RNA-Seq (FIG. 21a).

In order to examine whether Nurr1+Foxa2 co-expression prevents glial cell senescence, senescence-associated beta-galactosidase staining (SA-β-gal staining) (Abcam) was carried out (Dimri et al., 1995). Glia were plated at a density of 4.0×10$^4$ cells/cm$^2$ (or 4.0×10$^4$ cells/12-mm diameter well). At least 4,000 cells were seeded 12-18 hours before measuring SA-β-gal activity. After lentiviral transduction of Nurr1+Foxa2 genes into murine hippocampal glia, the staining of the senescence marker beta-galactosidase was examined.

Figure 21B:
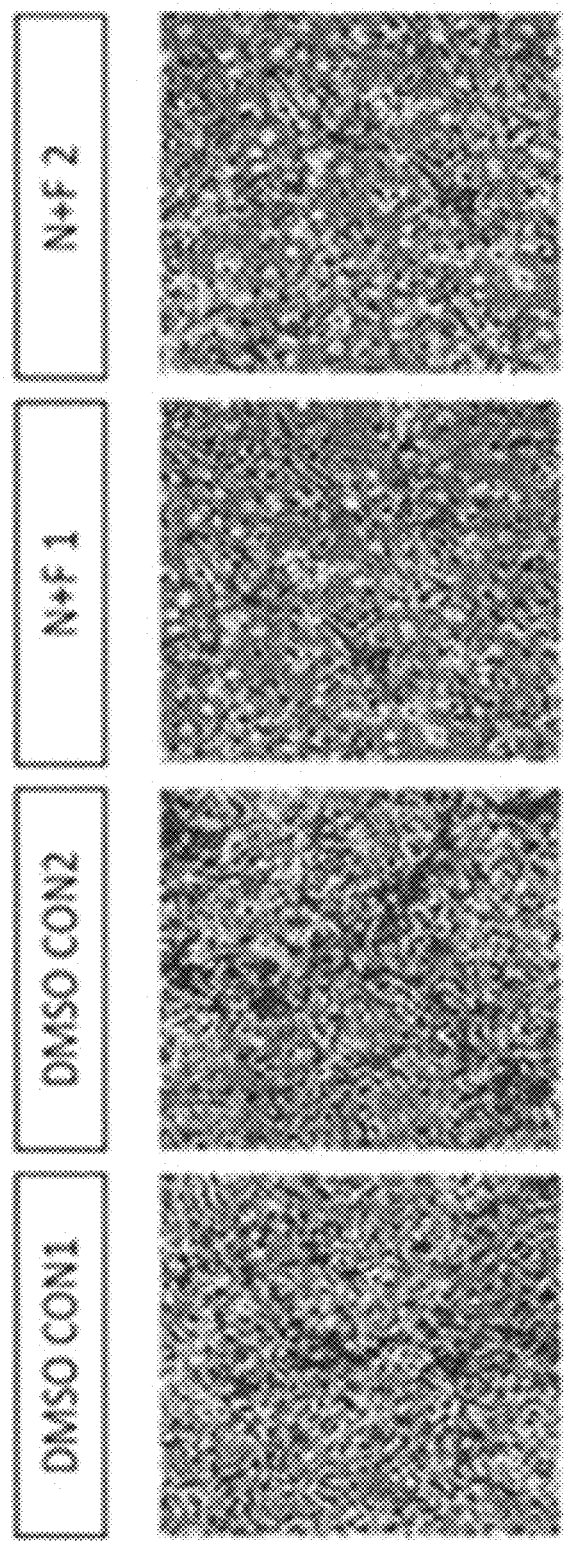
FIG. 21b shows staining results of beta-galactosidase (cellular senescence marker) in the control glial culture and the Nurr1+Foxa2-transduced glial culture.

FIG. 21b shows staining results of beta-galactosidase (cellular senescence marker) in the control glial culture and the Nurr1+Foxa2-transduced glial culture. In both the control glial culture and the Nurr1+Foxa2-expressed glial culture, the marker beta-galactosidase was found to be stained. A reduced number of stained cells was measured in the Nurr1+Foxa2-treated group, compared to the control.

Figure 21C:
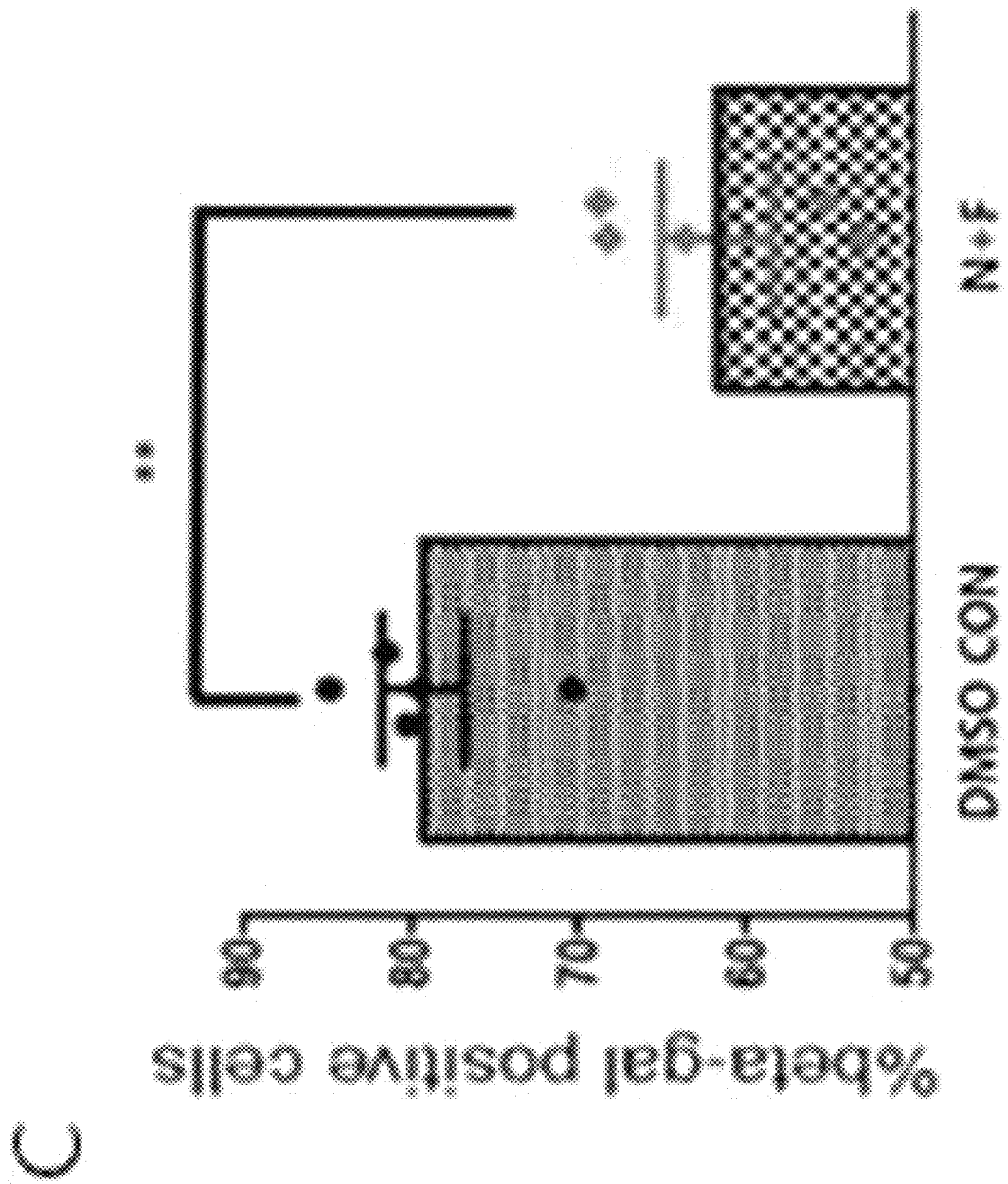
FIG. 21c is a bar graph depicting β-galactosidase-positive cell counts (glial cells) as measured by immunostaining for beta-galactosidase (cellular senescence marker) in a culture of control glia and a culture of Nurr1+Foxa2-transduced glia.
Figure 22:
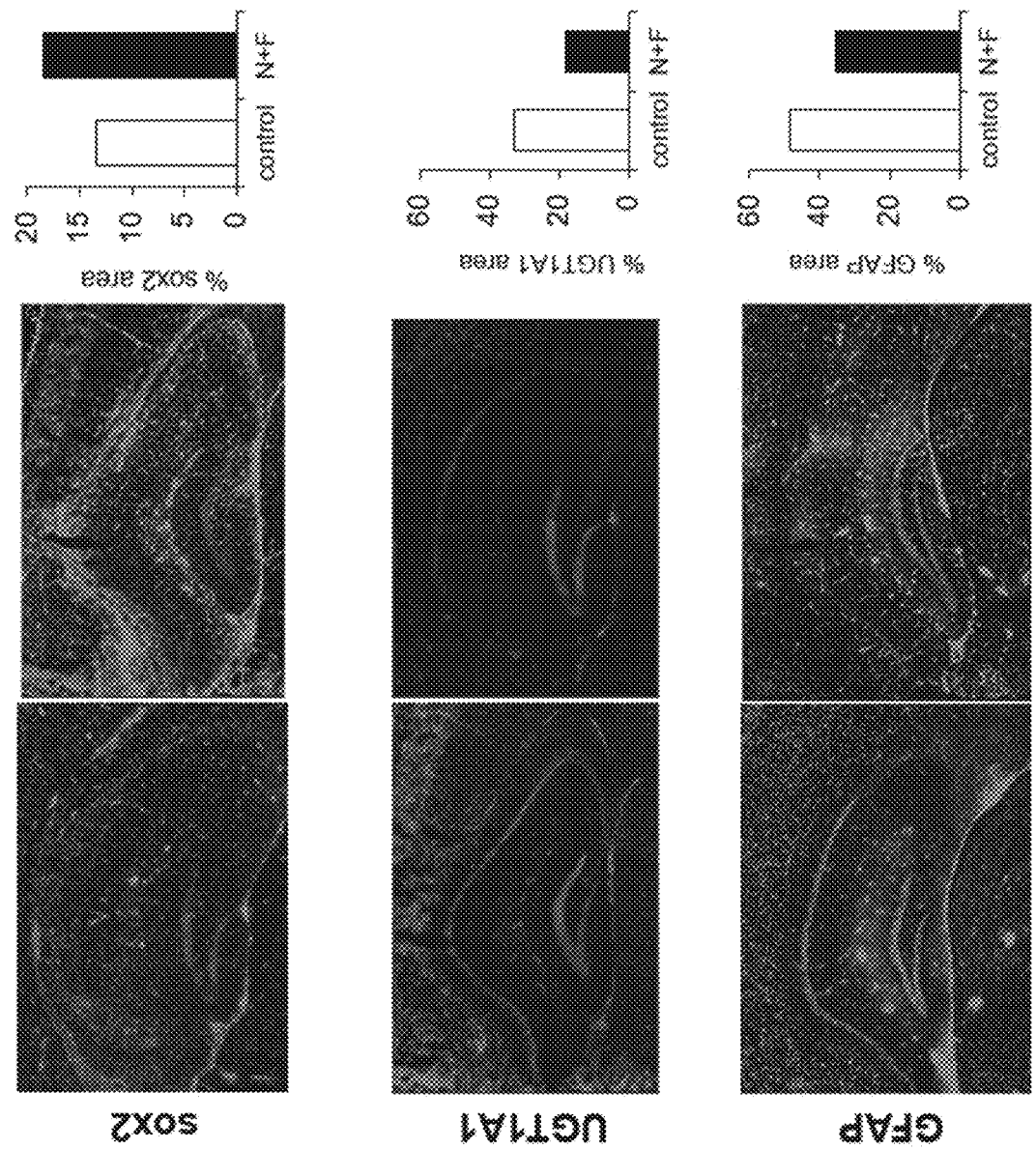
FIG. 22 shows fluorescence of Sox2, UGT1A1, and GFAP in the hippocampus of Alzheimer's disease model mice having Nurr1+Foxa2 genes introduced the glia thereof, as analyzed by immunostaining.

FIG. 21c is a graph depicting percentages of blue-stained positive cell counts (β-galactosidase+ glial cells) to total cell counts. Compared to control, the number of blue-stained positive cells was significantly reduced in the glia having Nurr1+Foxa2 genes introduced thereinto. Collectively, the data demonstrate that the co-expression of Nurr1+Foxa2 reduces the progression of senescence in senescent astrocytes, suggesting a correlation between an inflammation reducing mechanism and an anti-senescent action.

(14) Synergistic Effect of Nurr1 and Foxa2 on Sox2, UGT1A1, and GFAP in Amyloid Beta Alzheimer's Disease Model Sox2 is a transcription factor that is essential for maintaining self-renewal or pluripotency of stem cells and colocalizes with beta amyloid precursor protein (βAPP) in stem cells. In addition, a level of Sox2 tends to decline in the brain of Alzheimer's disease patients.

GFAP is a marker for astrocytes. Neuronal GFAP is observed mainly in the pyramidal neurons of the hippocampus of Alzheimer and Down syndrome patients and aged persons.

Nurr1+Foxa2 genes were transduced specifically into hippocampal and intracerebroventricular glia in 5xFAD mice at 15 months of age, with the aid of Nurr1-AAV9+ Foxa2-AAV9 virus. Two months after transduction of Nurr1+Foxa2 genes, fluorescence of Sox2, UGT1A1, and GFAP was detected by immunostaining in the hippocampus.

As a result, the Nurr1+Foxa2-treated group was found to increase in the level of Sox2, but to decrease in the levels of UGT1A1 and GFAP about two months later, as measured by immunostaining in the hippocampus (FIG. 23).

The result indicates that Nurr1+Foxa2 treatment has an influence on the expression of factors associated with Alzheimer's disease.

What is claimed is:

1. A method for inhibiting amyloid β accumulation and/or aggregation in a subject, comprising the steps of:
   identifying a subject in need of treatment for inhibiting amyloid β accumulation; and
   administering to the subject a therapeutically effective amount of a composition comprising Nurr1 and Foxa2 genes, wherein the administration inhibits amyloid β accumulation.

2. The method of claim 1, wherein the Nurr1 and Foxa2 genes are carried by a vector.

3. The method of claim 2, wherein the vector is viral vector.

4. The method of claim 3, wherein the viral vector comprises an adeno-associated virus, lentivirus, adenovirus, herpes virus, retrovirus, vaccinia virus, or poxvirus vector.

5. The method of claim 2, wherein the vector is a non-viral vector.

6. The method of claim 4, wherein the non-viral vector comprises a plasmid, RNA molecule, or lipofection vector.

7. The method of claim 1, wherein the composition comprises neurons, neuronal stem cells, or glia,
   and wherein the Nurr1 and Foxa2 genes have been introduced into the neurons, neuronal stem cells, or glia.

8. The method of claim 4, wherein the glia are astrocytes or microglia.

9. The method of claim 1, wherein the subject is a mammalian subject.

10. The method of claim 1, wherein the effective amount of the composition comprises from $5 \times 10^4$ to $5 \times 10^{15}$ viral genomes each of Nurr1 and Foxa2 per dose administered to the subject.

11. The method of claim 1, wherein the administration of the effective amount is directly to the brain, or by intravenous injection, to the subject.

12. A method for treatment of a disease in a subject caused by amyloid β accumulation and/or aggregation, comprising the steps of:
   identifying a subject in need of treatment for a disease caused by amyloid β accumulation; and
   administering to the subject a therapeutically effective amount of a composition comprising Nurr1 and Foxa2 genes, wherein the administration treats a disease caused by amyloid β accumulation and/or aggregation in the subject.

13. The method of claim 12, and wherein the Nurr1 and Foxa2 genes are carried by a vector.

14. The method of claim 13, wherein the vector is a viral vector.

15. The method of claim 13, wherein the vector is a non-viral vector.

16. The method of claim 12, wherein the composition comprises neurons, neuronal stem cells, or glia, and wherein the Nurr1 and Foxa2 genes have been introduced into the neurons, neuronal stem cells, or glia.

17. The method of claim 16, wherein the glia are astrocytes or microglia.

18. A method for inhibiting cellular senescence caused by amyloid β accumulation and/or aggregation in a subject, comprising the steps of:
   identifying a subject in need of treatment for inhibiting cellular senescence caused by amyloid β accumulation and/or aggregation; and
   administering to the subject a therapeutically effective amount of a composition comprising a vector carrying Nurr1 and Foxa2 genes, wherein the administration inhibits cellular senescence in the subject.

19. The method of claim 18, wherein the cellular senescence occurs in glia.

20. The method of claim 19, wherein the glia are astrocytes or microglia.

21. A method for inhibiting expression of inflammasomes, complements (C1 and C3), chemokines (CCL3 and CCL4), apolipoprotein E (ApoE), nuclear factor kappa-light-chain-enhancer of activated B cells (NFκB), or asparaginyl endopeptidase (AEP) in a subject, comprising the steps of:
   identifying a subject in need of treatment for inhibiting expression of inflammasomes, complements (C1 and C3), chemokines (CCL3 and CCL4), apolipoprotein E (ApoE), nuclear factor kappa-light-chain-enhancer of activated B cells (NFκB), or asparaginyl endopeptidase (AEP); and
   administering to the subject a therapeutically effective amount of a composition comprising Nurr1 and Foxa2 genes, wherein the administration inhibits expression of inflammasomes, complements (C1 and C3), chemokines (CCL3 and CCL4), apolipoprotein E (ApoE), nuclear factor kappa-light-chain-enhancer of activated B cells (NFκB), or asparaginyl endopeptidase (AEP) in the subject.

22. The method of claim 21, wherein the Nurr1 and Foxa2 genes are carried by a vector.

23. The method of claim 22, wherein the vector is a viral vector.

24. The method of claim 22, wherein the vector is a non-viral vector.

25. The method of claim 21, wherein the composition comprises neurons, neuronal stem cells, or glia, and wherein the Nurr1 and Foxa2 genes have been introduced into the neurons, neuronal stem cells, or glia.

26. The method of claim 25, wherein the glia are astrocytes or microglia.

27. A method for increasing expression of synaptogenic proteins (synapsin1 and synaptophsin) in a subject, comprising the steps of:
   identifying a subject in need of a treatment which increases expression of synaptogenic proteins (synapsin1 and synaptophsin); and
   administering to the subject a therapeutically effective amount of a composition comprising Nurr1 and Foxa2 genes, wherein the administration increases expression of synaptogenic proteins (synapsin1 and synaptophsin) in the subject.

28. The method of claim 27, wherein the Nurr1 and Foxa2 genes are carried by a vector.

29. The method of claim 28, wherein the vector is a viral vector.

30. The method of claim 28, wherein the vector is a non-viral vector.

31. The method of claim 27, wherein the composition comprises neurons, neuronal stem cells, or glia, and wherein the Nurr1 and Foxa2 genes have been introduced into the neurons, neuronal stem cells, or glia.

32. The method of claim 31, wherein the glia are astrocytes or microglia.

* * * * *